US008679845B2

(12) United States Patent
Maizels et al.

(10) Patent No.: US 8,679,845 B2
(45) Date of Patent: Mar. 25, 2014

(54) B CELLS MODIFIED TO REVERSIBLY INDUCE ACCELERATED MUTAGENESIS OF TARGET GENES

(75) Inventors: Nancy Maizels, Seattle, WA (US); W. Jason Cummings, Bellevue, WA (US); Munehisa Yabuki, Seattle, WA (US)

(73) Assignee: University of Washington, Seattle, WA (US)

( * ) Notice: Subject to any disclaimer, the term of this patent is extended or adjusted under 35 U.S.C. 154(b) by 765 days.

(21) Appl. No.: 12/598,031

(22) PCT Filed: Jun. 2, 2008

(86) PCT No.: PCT/US2008/065528
§ 371 (c)(1),
(2), (4) Date: Oct. 28, 2009

(87) PCT Pub. No.: WO2009/029315
PCT Pub. Date: Mar. 5, 2009

(65) Prior Publication Data
US 2010/0093033 A1    Apr. 15, 2010

Related U.S. Application Data

(60) Provisional application No. 60/932,672, filed on May 31, 2007.

(51) Int. Cl.
*C12N 15/63* (2006.01)
*C12N 5/06* (2006.01)

(52) U.S. Cl.
USPC .......................................... 435/455; 435/326

(58) Field of Classification Search
None
See application file for complete search history.

(56) References Cited

U.S. PATENT DOCUMENTS

| | | | |
|---|---|---|---|
| 6,909,031 B2 * | 6/2005 | Allen et al. ................. | 800/18 |
| 7,122,339 B2 | 10/2006 | Sale et al. | |
| 7,368,259 B2 | 5/2008 | Sale et al. | |
| 7,776,599 B2 | 8/2010 | Ohta et al. | |
| 2002/0028488 A1* | 3/2002 | Singh et al. ................ | 435/70.21 |
| 2005/0216976 A1* | 9/2005 | Meagher et al. ............ | 800/286 |
| 2006/0052585 A1 | 3/2006 | Grawunder et al. | |
| 2006/0099679 A1 | 5/2006 | Tsien et al. | |
| 2007/0186292 A1 | 8/2007 | Buerstedde et al. | |
| 2008/0193979 A1 | 8/2008 | Sale et al. | |

FOREIGN PATENT DOCUMENTS

| | | |
|---|---|---|
| AU | 77606049 | 8/2004 |
| EP | 1536004 | 6/2005 |
| EP | 1568765 | 8/2005 |
| EP | 1718734 | 10/2007 |
| EP | 1930430 | 6/2008 |
| WO | WO 01/59092 | 8/2001 |
| WO | WO 02/100998 | 12/2002 |
| WO | WO 03/061363 | 7/2003 |
| WO | WO2004/011644 | 2/2004 |
| WO | WO 2006/117699 | 11/2006 |
| WO | WO 2008/035463 | 3/2008 |
| WO | WO 2008/047480 | 4/2008 |

OTHER PUBLICATIONS

Sale et al., 2004, DNA Repair, vol. 3, pp. 693-702.*
Gallia et al. (1998, Oncogene, vol. 16, pp. 1879-1884.*
Sung et al. (1994, Science, vol. 265, pp. 1241-1243).*
Verschure et al. (2005, Molecular and Cellular Biology, vol. 25(11), pp. 4552-4564.*
Tagami et al. (2004, Cell, vol. 116, pp. 51-61).*
Schwager et al. (1991, The EMBO J., vol. 10(3), pp. 505-511.*
Almagro, J. et al., "Humanization of antibodies", Frontiers in bioscience (2008) 13: 1619-1633.
Arakawa, H., et al., "Immunoglobulin gene conversion: Insights from bursal B cells and the DT40 cell line", Dev. Dyn., (2004) 229: 458-464.
Cummings, W., "Chromatin structure regulates gene conversion", PLoS Biol., (Oct. 2007) 5: 2145-2155.
Maizels, N., "Immunoglobulin gene diversification", Annu. Rev. Genet, (2005) 39: 23-46.
Rada, C. et al., "AID-GFP chimeric protein increases hypermutation of Ig genes with no evidence of nuclear localization", Proc Natl Acad Sci, (2002) 99: 7003-7008.
Sale, J.E., "Immunoglobulin diversification in DT40: A model for vertebrate DNA damage tolerance", DNA Repair (Amst), (2004) 3: 693-702.
Sale, J.E., "Ablation of XRCC2/3 transforms immunoglobulin V gene conversion into somatic hypermutation", Nature (2001) 412: 921-926.
Takata, M., "The Rad51 paralog Rad51B promotes homologous recombinational repair", Mol Cell Biol (2000) 20: 6476-6482.

(Continued)

*Primary Examiner* — Michail Belyavskyi
(74) *Attorney, Agent, or Firm* — Karen S. Canady; canady + lortz LLP

(57) ABSTRACT

The present invention relates generally to mutagenesis of target genes that takes advantage of the natural mutagenic capabilities of B cells, and enhances those capabilities by bringing the process of diversification under control. The invention provides a method for rapidly and inducibly generating point mutations and other types of diversification in expressed genes, such as antibody genes. This method can be coupled with selection to identify B cell clones that produce, for example, antibodies of high affinity or specificity. The diversification process can be modulated, accelerated, halted, switched between methods of mutagenesis and the like. The modulation of diversification in accordance with the invention is both inducible and reversible. The invention provides a means of rapid and feasible development of a repertoire of variant immunoglobulins and other polypeptides.

31 Claims, 22 Drawing Sheets

(56) References Cited

OTHER PUBLICATIONS

Thompson, C.B. et al., "Somatic diversification of the chicken immunoglobulin light chain gene is limited to the rearranged variable gene segment", Cell (1987) 48: 369-378.
Yabuki, M. et al., "the MRE11-RAD50-NBSI complex accelerates somatic hypermutation and gene conversion of immunoglobulin variable regions", Nat Immunol (2005) 6: 730-736.
Yamamoto, K., et al., "Fanconi anemia protein FANCD2 promotes immunoglobulin gene conversion and DNA repair through a mechanism related to homologous recombination", Mol Cell Biol (2005) 25: 34-43.
Faili, A. et al., "AID-dependent somatic hypermutation occurs as a DNA single-strand event in the BL2 cell line", Nature Immunology, (2002) 3(9): 815-821.
Martin, A. et al., "Activation-induced cytidine deaminase turns on somatic hypermutation in hybridomas", Letters to Nature, (2002) 415(14): 802-806.
Martin, A. et al., "AID and Mismatch Repair in Antibody Diversification", Nature Reviews: Immunology, (2002) 2(8):605-614.
European Extended Search Report dated Nov. 7, 2011 related to corresponding European patent application No. 08828508.5.
Arakawa, H., et al., "Activation-Induced Cytidine Deaminase Initiates Immunoglobulin Gene Conversion and Hypermutation by a Common Intermediate",PLoS Biol, (2004) 2(7): 967-974.
Kitao, H., et al., "Regulation of histone H4 acetylation by transcription factor E2A in Ig gene conversion", Int'l Immunology, (2008) 20(2): 277-284.
Li, Y., et al., "Effects of tethering HP1 to Euchromatic Regions of the *Drosophila* genome", Development, (2003), 130: 1817-1824.
Tumbar, T., et al., "Large-Scale Chromatin Unfolding and Remodeling Induced by VP16 Acidic Activation Domain", The Journal of Cell Biology, (Jun. 28, 1999), 145(7): 1341-1354.

Official Notice and Third-party Submission of Information dated Oct. 5, 2011 (in Japanese + English translation) related to corresponding Japanese patent application No. 2010-510553.
ADlib, Techno Trend, Biotechnology Journal, 2006, 6(1): 77-80.
Seo, Hidetaka, "Enhancement of Homologous Recombination . . . Application", 27th Japan Molecular Biology Association Annual Meeting, Program and Lecture Abstract, 2004, pp. 365 W2O-7.
Seo, Hidetaka, "Rapid Generation of Specific Antibodies by Enhanced Homologus Recombination", Nature Biotechnology, 2005, 23(6):731-735.
Seo, Hidetaka, "HotPress", Cell Engineering, 2005, 24(8): 834-835.
Arakawa, Hiroshi et al., "Requirement of the Activation-Induced Deaminase (AID) Gene for Immunoglobulin Gene Conversion," Science, 2002, 295: 1301-1306.
Ohmori, Hitoshi et al., "A system for Generation of Antibodies and Mutant Proteins Using a B Cell . . . Machinery," Experimental Medicine, 2006, 24(9):1331-1335.
Todo, Kagefumi et al., "Novel In Vitro Screening System for Monoclonal . . . Library," J. Biosci. Bioengineering, 2006, 102(5):478-481.
Vaysse, Laurence et al., "Development of a Self-Assembling Nuclear Targeting . . . Protein", The Journal of Biological Chemistry, 2004, 279(7):5555-5564.
Bushman, Frederic, "Tethering Human Immunodeficiency Virus 1 Integrase . . . Sequences", Proc. Natl. Acad. Sci., 1994, 91: 9233-9237.
Graumann, Peter et al., "Coupling of Asymmetric Division to Polar . . . *Bacillus subtilis*", J. of Bacteriology, 2001, 183(13):4052-4060.
Sonoda, E., "Chicken B Lymphocytes Diversity Immunoglobulin Genes . . . Lymphocytes", Molecular Medicine, 2000, 37: 160-171.
Japanese Notice of Reasons for Rejection dated Jan. 30, 2013 (Japanese + English translation) related to Japanese patent application No. 2010-510553.

\* cited by examiner

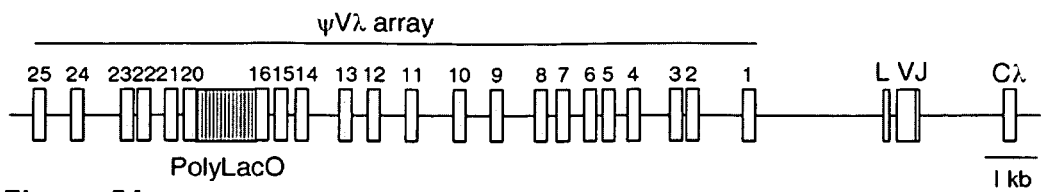
Figure 5A
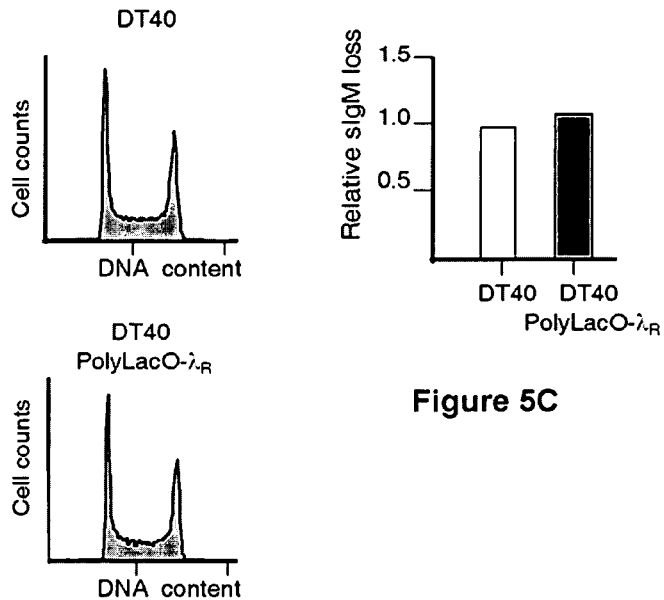
Figure 5B
Figure 5C
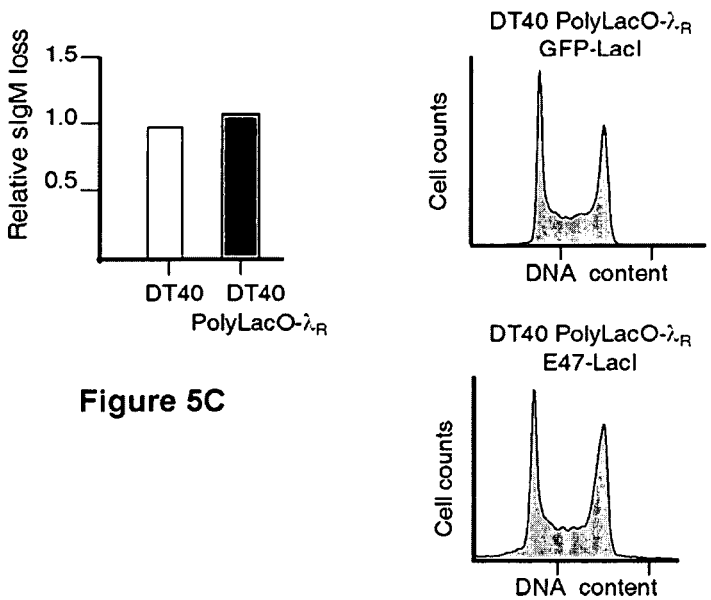
Figure 5D
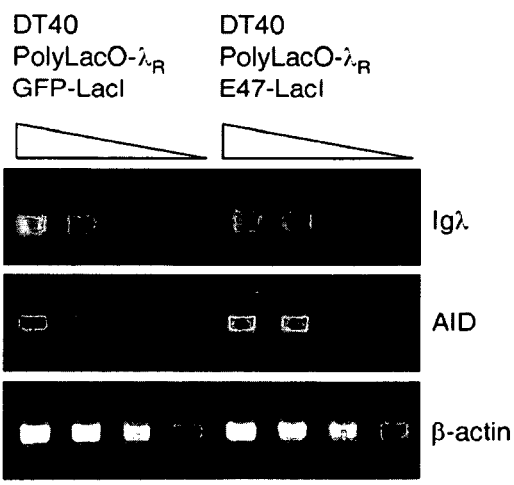
Figure 5E
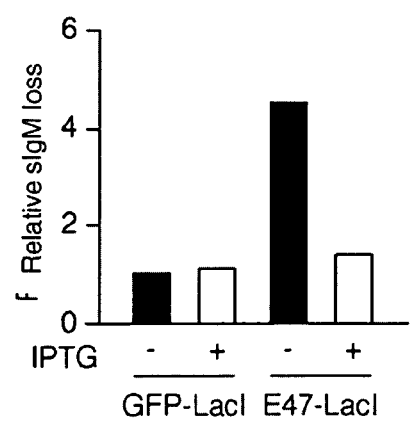
Figure 5F

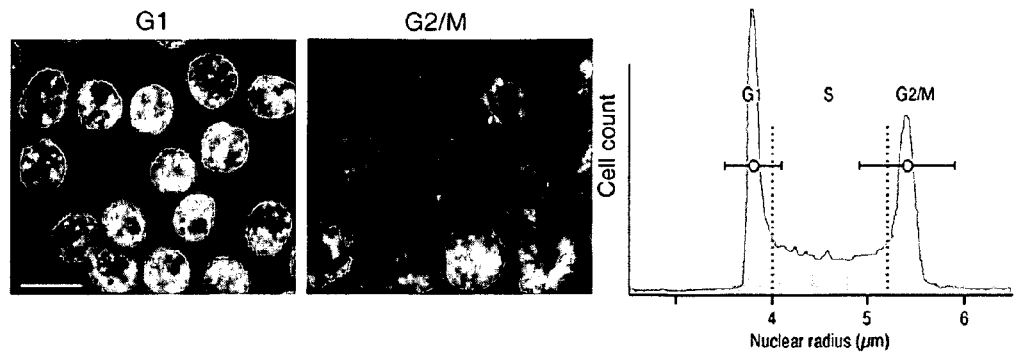
Figure 6A
Figure 6B
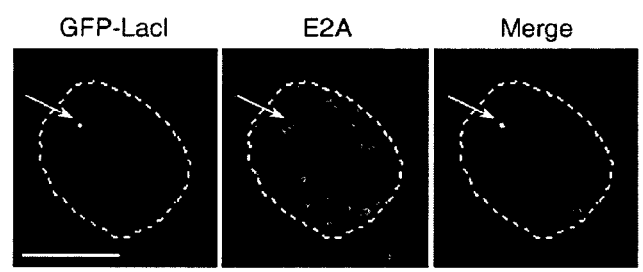
Figure 7A
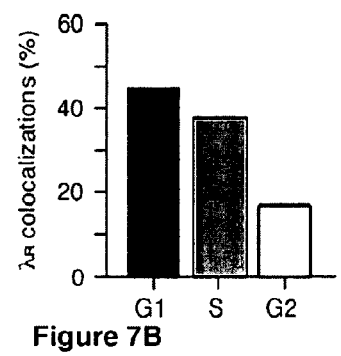
Figure 7B
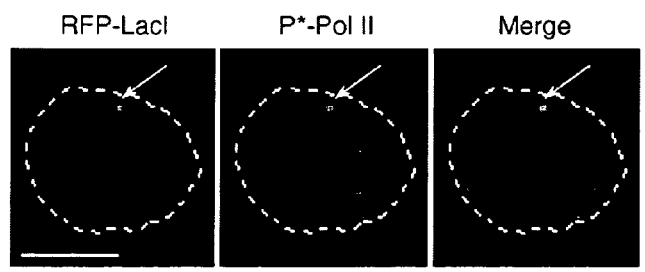
Figure 7C
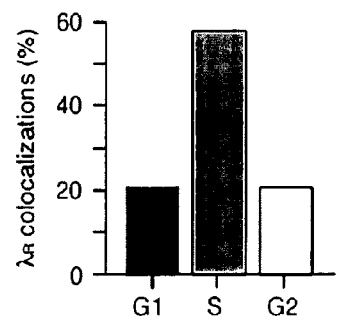
Figure 7D

FIGURE 15

```
DT40    GAC ATC CCT TCA CGA TTC TCC GGT TCC CTA TCC GGC TCC ACA AAC ACA TTA ACC ATC ACT GGG GTC
GFP-1   --- --- --- --- --- --- --- --- --- --- --- --- --- --- --- --- --- --- --- --- ---
GFP-2   --- --- --- --- --- --- --- --- --- --- --- --- --- --- --- --- --- --- --- --- ---
GFP-3   --- --- --- --- --- -Ⓐ- --- --- --- --- --- --- --- --- --- --- --- --- --- --- ---
GFP-4   --- --- --- --- --- --- --- --- --- -Ⓐ- --- --- --- --- --- --- --- --- --- --- ---
GFP-5   --- --- --- --- --- --- --- --- --- --- --- --- --- --- --- --- --- --- --- --- ---
GFP-6   --- --- --- --- --- --- --- --- --- --- --- --- --- --- --- --- --- --- --- --- ---
GFP-7   --- --- --- --- --- --- --- --- --- --- --- --- --- --- --- --- --- --- --- --- ---
GFP-8   --- --- --- --- --- --- --- --- --- --- --- --- --- --- --- --- --- --- --- --- ---
GFP-9   --- --- --- --- --- --- --- --- --- --- --- --- --- --- --- --- --- --- --- --- ---
GFP-10  --- --- --- --- --- --- --- --- --- --- --- --- --- --- --- --- --- --- --- --- ---
GFP-11  --- --- --- --- --- --- --- --- --- --- --- --- --- --- --- --- --- --- --- --- ---
GFP-12  --- --- --- --- --- --- --- --- --- --- --- --- --- --- --- --- --- --- --- --- ---
GFP-13  --- --- --- --- --- --- --- --- --- --- --- --- --- --- --- --- --- --- --- --- ---
GFP-14  --- --- --- --- --- --- --- --- --- --- --- --- --- --- --- --- --- --- --- --- ---
GFP-15  --- --- --- --- --- --- --- --- --- --- --- --- --- --- --- --- --- --- --- --- ---
GFP-16  --- --- --- --- --- --- --- --- --- --- --- --- --- --- --- --- --- --- --- --- ---
GFP-17  --- --- --- --- --- --- --- --- --- --- --- --- --- --- --- --- --- --- --- --- ---
GFP-18  --- --- --- --- --- --- --- --- --- --- --- --- --- --- --- --- --- --- --- --- ---
GFP-19  A-- --- --- --- --- --- --- --- --- --- --- --- --- --- --- --- --- --- --- --- ---

DT40    CGA GCC GAT GAC GAG GCT GTC TAT TTC TGT GGG AGT GCA GAC AAC AGT GGT GCT GCA TTT GGG GCC
GFP-1   --- --- --- --- --- --- --- --- --- --- --- --- --- --- --- --- --- --- --- --- --- ---
GFP-2   --- --- --- --- --- --- --- --- --- --- --- --- --- --- --- --- --- --- --- --- --- ---
GFP-3   --- --- --- --- --- --- --- --- --- --- --- --- --- --- --- --- --- --- --- --- --- ---
GFP-4   --- --- --- --- --- --- --- --- --- --- --- --- --- --- --- --- --- --- --- --- --- ---
GFP-5   --- --- --- --- --- --- --- --- --- --- -Ⓣ- --- --- --- --- --- --- --- --- --- --- ---
GFP-6   --- --- --- --- --- --- --- --- --- --- --- --- --- --- --- --- --- --- --- --- --- ---
GFP-7   --- --- --- --- --- --- --- --- --- --- --- --- --- --- --- --- --- --- --- --- --- ---
GFP-8   --- --- --- --- --- --- --- --- --- --- --- --- --- --- --- --- --- -Ⓐ-Ⓐ- --- --- --- ---
GFP-9   --- --- --- --- --- --- --- --- --- --- --- --- --- --- --- --- --- --- --- --- --- ---
GFP-10  --- --- --- --- --- --- -Ⓐ- --- --- --- --- --- --- Ⓒ --- --- --- --- --- --- ---
GFP-11  --- --- --- --- --- --- --- --- --- --- --- --- --- --- --- --- --- --- --- --- --- ---
GFP-12  --- --- --- --- --- --- --- --- --- --- --- --- --- --- --- --- --- --- --- --- --- ---
GFP-13  --- --- --- --- --- --- --- --- --- --- --- --- --- --- --- --- --- --- --- --- --- ---
GFP-14  --- --- --- --- --- --- --- --- --- --- --- --- --- --- --- --- --- --- --- --- --- ---
GFP-15  --- --- --- --- --- --- --- --- --- Ⓒ --- --- --- --- --- --- --- --- --- --- --- ---
GFP-16  --- --- --- --- --- --- --- --- --- --- --- --- --- --- --- --- --- --- --- --- --- ---
GFP-17  --- --- --- --- --- --- --- --- --- --- --- --- --- --- --- --- --- --- --- --- --- ---
GFP-18  --- --- --- --- --- --- --- --- --- --- --- --- --- --- --- --- --- --- --- --- --- ---
GFP-19  --- --- --- --- --- --- --- --- --- --- --- --- --- --- --- --- --- --- --- --- --- ---

DT40    GGG ACA ACC CTG ACC GTC CTA GGT GAG TCG CTG ACC TCG TCT CGG TCT
GFP-1   --- --- --- --- --- --- --- --- --- --- --- --- --- --- --- ---
GFP-2   --- --- --- --- --- --- --- --- --- --- --- --- --- --- --- ---
GFP-3   --- --- --- --- --- --- --- --- --- --- --- --- --- --- --- ---
GFP-4   --- --- --- --- --- --- --- --- --- --- --- --- --- --- --- ---
GFP-5   --- --- --- --- --- --- --- --- --- --- --- --- --- --- --- ---
GFP-6   --- --- --- --- --- --- --- --- --- --- --- --- --- --- --- ---
GFP-7   --- --- --- --- --- --- --- --- --- --- --- --- --- --- --- ---
GFP-8   --- --- --- --- --- --- --- --- --- --- --- --- --- --- --- ---
GFP-9   --- --- --- --- --- --- --- --- --- --- --- --- --- --- --- ---
GFP-10  --- --- --- --- --- --- --- --- --- --- --- --- --- --- --- ---
GFP-11  --- --- --- --- --- --- --- --- --- --- --- --- --- --- --- ---
GFP-12  --- --- --- --- --- --- --- --- --- --- --- --- --- --- --- ---
GFP-13  --- --- --- --- --- --- --- --- --- --- --- --- --- --- --- ---
GFP-14  --- --- --- --- --- --- --- --- --- --- --- --- --- --- --- ---
GFP-15  --- --- --- --- --- --- --- --- --- --- --- --- --- --- --- ---
GFP-16  --- --- --- --- --- --- --- --- --- --- --- --- --- --- --- ---
GFP-17  --- --- --- --- --- --- --- --- --- --- --- --- --- --- --- ---
GFP-18  --- --- --- --- --- --- --- --- --- --- --- --- --- --- --- ---
GFP-19  --- --- --- --- --- --- --- --- --- --- --- --- --- --- --- ---
```

FIGURE 15 (CONT'D)

LacI-GFP-HP1
```
DT40    TCT CCC TCT CCA GGT TCC CTG GTG CAG GCA GCG CTG ACT CAG CCG GCC TCG GTG TCA GCA AAC CTA
HP1-1   --- --- --- --- --- --- --- --- --- --- --- --- --- --- --- --- --- --- --- --- ---
HP1-2   --- --- --- --- --- --- --- --- --- --- --- --- --- --- --- --- --- --- --- --- ---
HP1-3   --- --- --- --- --- --- --- --- --- --- --- --- --- --- --- --- --- --- --- --- ---
HP1-4   --- --- --- --- --- --- --- --- --- --- --- --- --- --- --- --- --- --- --- --- ---
HP1-5   --- --- --- --- --- --- --- --- --- --- --- --- --- --- --- --- --- --- --- --- ---
HP1-6   --- --- --- --- --- --- --- --- --- --- --- --- --- --- --- --- --- --- --- --- ---
HP1-7   --- --- --- --- --- --- --- --- --- --- --- --- --- --- --- --- --- --- --- --- ---
HP1-8   --- --- --- --- --- --- --- --- --- --- --- --- --- --- --- --- --- --- --- --- ---
HP1-9   --- --- --- --- --- --- --- --- --- --- --- --- --- --- --- --- --- --- --- --- ---
HP1-10  --- --- --- --- --- --- --- --- --- --- --- --- --- --- --- --- --- --- --- --- ---
HP1-11  --- --- --- --- --- --- --- --- --- --- --- --- --- --- --- --- --- --- --- --- ---
HP1-12  --- --- --- --- --- --- --- --- --- --- --- --- --- --- --- --- --- -C- -T- -G-
HP1-13  --- --- -T- --- --- --- (CA)-T- --- --- --- -A- --- --- --- -A- -T- --- --- --- ---
HP1-14  --- --- --- --- --- --- --- --- --- --- --- --- --- --- --- --- --- --- --- --- ---

DT40    GGA GGA ACC GTC AAG ATC ACC TGC TCC GGG GGT GGC AGC TAT GCT GGA AGT TAC TAT TAT GGC TGG
HP1-1   --- --- --- --- --- --- --- --- --- --- --- --- --- --- --- --- --- --- --- --- --- ---
HP1-2   --- --- --- --- --- --- --- --- --- --- --- --- --- --- --- --- --- --- --- --- --- ---
HP1-3   --- --- --- --- --- --- --- --- --- --- --- --- --- --- --- --- --- --- --- --- --- ---
HP1-4   --- --- --- --- --- --- --- --- --- --- --- --- --- --- --- --- --- --- --- --- --- ---
HP1-5   --- --- --- --- --- --- --- --- --- --- --- --- --- --- --- --- --- --- --- --- --- ---
HP1-6   --- --- --- --- --- --- --- --- --- --- --- --- --- --- --- --- --- --- --- --- --- ---
HP1-7   --- --- --- --- --- --- --- --- --- --- --- --- --- --- --- G-- --- --- --- --- --- ---
HP1-8   --- --- --- --- --- --- --- -A- --- --- --- --- --- --- --- --- --- --- --- --- --- ---
HP1-9   --- --- --- --- --- --- --- --- --- --- --- --- --- --- --- --- --- --- --- --- --- ---
HP1-10  --- --- --- --- --- --- --- --- --- --- --- --- --- --- --- --- --- --- --- --- --- ---
HP1-11  --- --- --- --- --- --- --- --- --- --- --- --- --- --- --- G-- --- --- --- --- --- ---
HP1-12  -C-C --- --- --- --- --- --- --- --- --- --- --- --- --- --- --- --- --- --- --- --- ---
HP1-13  --- --- -A- --- --- --- -A- --- --- -A- --- --- --- --- --- --- --- --- --- --- --- ---
HP1-14  --- --- --- --- --- --- --- --- --- --- --- --- --- --- --- G-- --- --- --- --- --- ---

DT40    TAC CAG CAG AAG TCT CCT GGC AGT GCC CCT GTC ACT GTG ATC TAT GAC AAC GAC AAG AGA CCC TCG
HP1-1   --- --- --- --- --- --- --- --- --- --- --- --- --- --- --- --- --- --- --- --- --- ---
HP1-2   --- --- --- --- --- --- --- --- --- --- --- --- --- --- --- --- --- --- --- --- --- ---
HP1-3   T-- --- --- --- --- --- --- --- --- --- --- --- --- --- --- --- --- --- --- --- --- ---
HP1-4   --- --- --- --- --- --- --- --- --- --- --- --- -C- --- --- --- --- --- --- --- --- ---
HP1-5   --- --- --- --- --- --- --- --- --- --- --- --- --- --- --- --- --- --- --- --- --- ---
HP1-6   --- --- --- --- --- --- --- --- --- --- --- --- --- --- --- --- --- --- --- --- --- ---
HP1-7   --- --- --- --- --- --- --- --- --- --- --- --- --- --- --- --- --- --- --- --- --- ---
HP1-8   --- --- --- --- --- --- --- --- --- --- --- --- --- --- --- --- --- --- --- --- --- ---
HP1-9   --- --- --- --- --- -A- --- --- --- --- --- --- --- --- --- --- --- --- --- --- --- ---
HP1-10  --- --- --- --- --- --- --- --- --- --- --- --- --- C-- --- --- -C- --- --- --- --- ---
HP1-11  --- --- --- --- --- --- --- --- --- --- --- --- --- --- --- --- --- --- --- --- --- ---
HP1-12  --- --- --- --- --- --- --- --- --- --- --- --- --- --- --- -C- --- --- --- --- --- ---
HP1-13  --- --- --- --- --- --- --- --- --- --- --- --- --- --- --- --- --- --- --- --- --- ---
HP1-14  --- --- --- --- --- --- --- --- --- --- --- --- --- --- --- --- --- --- --- --- --- ---

DT40    GAC ATC CCT TCA CGA TTC TCC GGT TCC CTA TCC GGC TCC ACA AAC ACA TTA ACC ATC ACT GGG GTC
HP1-1   --- --- --- --- --- --- --- --- --- --- --- --- --- --- --- --- --- --- --- --- --- ---
HP1-2   --- --- --- --- --- --- --- --- --- --- --- --- --- --- --- --- --- --- --- --- --- ---
HP1-3   --- --- --- --- --- --- --- --- --- --- --- --- --- --- --- --- --- --- --- --- --- ---
HP1-4   --- --- --- --- --- --- --- --- --- --- --- --- --- --- --- --- --- --- --- --- --- ---
HP1-5   --- --- --- --- --- --- --- --- --- --- --- --- --- --- --- --- --- --- --- --- --- ---
HP1-6   --- --- --- --- --- --- --- --- --- --- --- --- --- --- --- --- --- --- --- --- --- ---
HP1-7   --- --- --- --- --- --- --- --- --- --- --- --- --- --- --- --- --- --- --- --- --- ---
HP1-8   --- --- --- --- --- --- --- --- --- --- --- --- --- --- --- --- --- --- --- --- --- ---
HP1-9   --- --- --- --- --- --- --- --- --- --- --- --- --- --- --- --- --- --- --- --- --- ---
HP1-10  --- --- --- --- --- --- --- --- --- --- --- --- --- --- --- --- --- --- --- --- --- ---
HP1-11  --- --- --- --- --- --- --- --- --- --- --- --- --- --- --- --- --- --- --- --- --- ---
HP1-12  --- --- --- --- --- --- --- --- --- --- --- --- --- --- --- --- --- --- --- --- --- ---
HP1-13  --- --- --- --- --- --- --- --- --- --- --- --- --- --- --- --- --- --- --- --- --- ---
HP1-14  --- --- --- --- --- --- --- --- --- --- -T- --- --- --- --- --- --- --- --- --- --- ---
```

FIGURE 15 (CONTINUES)

| DT40 | CGA | GCC | GAT | GAC | GAG | GCT | GTC | TAT | TTC | TGT | GGG | AGT | GCA | GAC | AAC | AGT | GGT | GCT | GCA | TTT | GGG | GCC |
|---|---|---|---|---|---|---|---|---|---|---|---|---|---|---|---|---|---|---|---|---|---|---|
| HP1-1 | --- | --- | --- | --- | --- | --- | --- | --- | --- | --- | --- | --- | --- | --- | --- | --- | --- | --- | --- | --- | --- | --- |
| HP1-2 | --- | --- | --- | --- | --- | --- | --- | --- | --- | --- | --- | --- | --- | --- | --- | --- | --- | --- | --- | --- | --- | --- |
| HP1-3 | --- | --- | --- | --- | --- | --- | --- | --- | --- | --- | --- | --- | --- | --- | --- | --- | --- | --- | --- | --- | --- | --- |
| HP1-4 | --- | --- | --- | --- | --- | --- | --- | --- | --- | --- | --- | --- | --- | --- | --- | --- | --- | --- | --- | --- | --- | --- |
| HP1-5 | --- | --- | --- | --- | --- | --- | --- | --- | --- | --- | --- | --- | --- | --- | --- | --- | --- | --- | --- | --- | --- | --- |
| HP1-6 | --- | --- | --- | --- | --- | --- | --- | --- | (C) | --- | --- | --- | --- | --- | --- | --- | --- | --- | --- | --- | --- | --- |
| HP1-7 | --- | --- | --- | --- | --- | --- | --- | --- | --- | --- | --- | --- | --- | --- | --- | --- | --- | --- | --- | --- | --- | --- |
| HP1-8 | --- | --- | --- | --- | --- | --- | --- | --- | --- | --- | --- | --- | --- | --- | --- | --- | --- | --- | --- | --- | --- | --- |
| HP1-9 | --- | --- | --- | --- | --- | --- | --- | --- | --- | --- | --- | --- | --- | --- | --- | --- | --- | --- | --- | --- | --- | --- |
| HP1-10 | --- | --- | --- | --- | --- | --- | --- | --- | --- | --- | --- | --- | --- | --- | --- | --- | --- | --- | --- | --- | --- | --- |
| HP1-11 | --- | --- | --- | --- | --- | --- | --- | --- | --- | --- | --- | --- | --- | --- | --- | --- | --- | --- | --- | --- | --- | --- |
| HP1-12 | --- | --- | --- | --- | --- | --- | --- | --- | --- | --- | --- | --- | --- | --- | --- | --- | --- | --- | --- | --- | --- | --- |
| HP1-13 | --- | --- | --- | --- | --- | --- | --- | --- | --- | --- | --- | --- | --- | --- | --- | --- | --- | --- | --- | --- | --- | --- |
| HP1-14 | --- | --- | --- | --- | --- | --- | --- | --- | --- | --- | --- | --- | --- | --- | --- | --- | --- | --- | --- | --- | --- | --- |

| DT40 | GGG | ACA | ACC | CTG | ACC | GTC | CTA | GGT | GAG | TCG | CTG | ACC | TCG | TCT | CGG | TCT |
|---|---|---|---|---|---|---|---|---|---|---|---|---|---|---|---|---|
| HP1-1 | --- | --- | --- | --- | --- | --- | --- | --- | --- | (A) | --- | --- | --- | --- | --- | --- |
| HP1-2 | --- | --- | --- | --- | --- | --- | --- | --- | --- | (G) | --- | --- | --- | --- | --- | --- |
| HP1-3 | --- | --- | --- | --- | --- | --- | --- | --- | --- | --- | --- | --- | --- | --- | --- | --- |
| HP1-4 | --- | --- | --- | --- | --- | --- | --- | --- | --- | --- | --- | --- | --- | --- | --- | --- |
| HP1-5 | --- | --- | --- | --- | --- | --- | --- | --- | --- | --- | --- | --- | --- | (A) | --- | --- |
| HP1-6 | --- | --- | --- | --- | --- | --- | --- | --- | --- | --- | --- | --- | --- | --- | --- | --- |
| HP1-7 | --- | --- | --- | --- | --- | --- | --- | --- | --- | --- | --- | --- | --- | --- | --- | --- |
| HP1-8 | --- | --- | --- | --- | --- | --- | --- | --- | --- | --- | --- | --- | --- | --- | --- | --- |
| HP1-9 | --- | --- | --- | --- | --- | --- | --- | --- | --- | --- | --- | --- | --- | --- | --- | --- |
| HP1-10 | --- | --- | --- | --- | --- | --- | --- | --- | --- | -A | (T) | --- | --- | --- | --- | --- |
| HP1-11 | --- | --- | (C/Y) | --- | --- | --- | --- | --- | --- | --- | --- | --- | --- | --- | --- | --- |
| HP1-12 | --- | --- | --- | --- | --- | --- | --- | --- | --- | --- | --- | --- | --- | --- | --- | --- |
| HP1-13 | --- | --- | --- | --- | --- | --- | --- | --- | --- | --- | --- | --- | --- | --- | --- | --- |
| HP1-14 | --- | --- | --- | --- | --- | --- | --- | --- | --- | --- | --- | --- | --- | --- | --- | --- |

```
DT40      GAC ATC CCT TCA CGA TTC TCC GGT TCC CTA TCC GGC TCC ACA AAC ACA TTA ACC ATC ACT GGG GTC
HIRA-1    --- --- --- --- --- --- --- --- AA- --- --- --- -G GG- --- --- --- --- --- --- ---
HIRA-2    A-- --- --- --- --- --- --- --- --- --- --- --- --- --- --- --- --- --- --- --- ---
HIRA-3    --- --- --- --- --- --- --- --- --- --- --- --- --- --- --- --- --- --- --- --- ---
HIRA-4    --- --- --- --- --- --- --- --- --- --- --- --- --- --- --- --- --- --- --- --- ---
HIRA-5    --- --- --- --- --- --- --- --- --- --- --- --- --- --- --- --- --- --- --- --- ---
HIRA-6    --- --- --- --- --- --- --- --- --- --- --- --- --- --- --- --- --- --- --- --- ---
HIRA-7    --- --- --- --- --- --- --- --- --- --- --- --- --- --- --- --- --- --- --- --- ---
HIRA-8    --- --- --- --- --- --- --- --- --- --- --- --- --- --- --- --- --- --- --- --- ---
HIRA-9    --- --- --- --- --- --- --- --- --- --- --- --- --- --- --- --- --- --- --- --- ---
HIRA-10   --- --- --- --- --- --- --- --- --- --- --- --- --- --- --- --- --- --- --- --- ---
HIRA-11   --- --- --- --- --- --- --- --- --- --- --- --- --- --- --- --- --- --- --- --- ---
HIRA-12   --- --- --- --- --- --- --- --- --- --- --- --- --- --- --- --- --- --- --- --- ---
HIRA-13   --- --- --- --- --- --- --- --- --- --- --- --- --- --- --- --- --- --- --- --- ---
HIRA-14   --- --- --- --- --- --- --- --- --- --- --- --- --- --- --- --- --- --- --- --- ---

DT40      CGA GCC GAT GAC GAG GCT GTC TAT TTC TGT GGG AGT GCA GAC AAC AGT GGT GCT GCA TTT GGG GCC
HIRA-1    --- --- --- --- --- --- --- --- --- --- --- --- --- --- --- --- --- --- --- --- --- ---
HIRA-2    --- --- --- --- --- --- --- --- --- --- --- --- --- --- --- --- --- --- --- --- --- ---
HIRA-3    --- --- --- --- --- --- --- --- T --- --- --- --- --- --- --- --- --- --- --- --- ---
HIRA-4    --- --- --- --- --- --- --- --- --- --- --- --- --- --- --- --- --- --- --- --- --- ---
HIRA-5    --- --- --- --- --- --- --- --- --- --- --- --- --- --- --- --- --- --- --- --- --- ---
HIRA-6    --- --- --- --- --- --- --- --- --- --- --- --- --- --- --- --- --- --- --- --- --- ---
HIRA-7    --- --- --- --- --- --- --- --- C --- --- --- --- --- --- --- --- --- --- --- --- ---
HIRA-8    --- --- --- --- --- --- --- --- --- --- --- --- --- --- --- --- --- --- --- --- --- ---
HIRA-9    --- --- --- --- --- --- --- --- --- --- --- --- --- --- --- --- --- --- --- --- --- ---
HIRA-10   --- --- --- --- --- --- --- --- --- --- --- --- --- --- --- --- --- --- --- --- --- ---
HIRA-11   --- --- --- --- --- --- --- --- --- --- --- --- --- --- --- --- --- --- --- --- --- ---
HIRA-12   --- --- --- --- --- --- --- --- --- --- --- --- --- --- --- --- --- --- --- --- --- ---
                                              CAGGGAG
HIRA-13   --- --- --- --- --- --- --- --- C --- --- ▼ --- --- --- --- --- A --- --- --- ---
                                   AACCATCACTGGGGTCCGAGCCGATGACGAGGCTGTCTATT
HIRA-14   --- --- --- --- --- --- --- --- ▼ --- --- --- --- --- --- --- --- --- --- --- --- ---

DT40      GGG ACA ACC CTG ACC GTC CTA GGT GAG TCG CTG ACC TCG TCT CGG TCT
HIRA-1    --- --- --- --- --- --- --- --- --- --- --- --- --- --- --- ---
HIRA-2    --- --- --- --- --- --- --- --- --- --- --- --- --- --- --- ---
HIRA-3    --- --- --- --- --- --- --- --- --- --- --- --- --- --- --- ---
HIRA-4    --- --- --- --- --- --- --- --- --- --- --- --- --- --- --- ---
HIRA-5    --- --- --- --- --- --- --- --- --- --- --- --- --- --- --- ---
HIRA-6    --- --- --- --- --- --- --- --- --- --- --- --- --- --- --- ---
HIRA-7    --- --- --- --- --- --- --- --- --- --- --- --- --- --- --- ---
HIRA-8    --- --- --- --- --- --- --- --- --- --- --- --- --- --- --- ---
HIRA-9    --- --- --- --- --- --- --- --- --- --- --- --- --- --- --- ---
HIRA-10   --- --- --- --- --- --- --- --- --- --- --- --- --- --- --- ---
HIRA-11   --- --- --- --- --- --- --- --- --- --- --- --- --- --- --- ---
HIRA-12   --- --- --- --- --- --- --- --- --- --- --- --- --- --- --- ---
HIRA-13   --- --- --- --- --- --- --- --- --- --- --- --- --- --- --- ---
HIRA-14   --- --- --- --- --- --- --- --- --- --- --- --- --- --- --- ---
```

FIGURE 23 (CONT'D)

SEQUENCE LISTING

<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
attgcgcatt gttatccaca                                          20

<210> SEQ ID NO 2
<211> LENGTH: 20
<212> TYPE: DNA

```
<213> ORGANISM: Artificial Sequence
<220> FEATURE:
<223> OTHER INFORMATION: Synthetic Primer

<400> SEQUENCE: 2
taagccctgc cagttctcat                                                20

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
gtcagcaaac ccaggagaaa c                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
aatccacagt cactgggctg                                                20

<210> SEQ ID NO 5
<211> LENGTH: 29
<212> TYPE: DNA
<213> ORGANISM: Artificial Sequence
<220> FEATURE:
<223> OTHER INFORMATION: Synthetic Primer

<400> SEQUENCE: 5
gccgtcactg attgccgttt tctcccctc                                      29

<210> SEQ ID NO 6
<211> LENGTH: 29
<212> TYPE: DNA
<213> ORGANISM: Artificial Sequence
<220> FEATURE:
<223> OTHER INFORMATION: Synthetic Primer

<400> SEQUENCE: 6
cgagacgagg tcagcgactc acctaggac                                      29

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
ctgtggcctg tcagtgctta                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
gcagggaacc acaagaacat                                                20
```

```
<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
gggacttgtg tcaccaggat                                                    20

<210> SEQ ID NO 10
<211> LENGTH: 21
<212> TYPE: DNA
<213> ORGANISM: Artificial Sequence
<220> FEATURE:
<223> OTHER INFORMATION: Synthetic Primer

<400> SEQUENCE: 10
cgcagtcaca tgtggaatat c                                                  21

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
gagccccatt ttctctcctc                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
gagatgtgca gcaacaagga                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
ccctctccct atgcaggttc                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
cccctatcac cataccagga                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer
```

-continued

```
<400> SEQUENCE: 15
ccattttctc ccctctctcc                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
tcaccctaca gcttcagtgc                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
ccattttctc ccctctctcc                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
cagcccatca ctccctctta                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19
tctgttggtt tcagcacagc                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
gcagttctgt gggatgaggt                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic Primer

<400> SEQUENCE: 21
ggctcctgta gctgatcctg                                                  20

<210> SEQ ID NO 22
<211> LENGTH: 20
<212> TYPE: DNA
```

```
<213> ORGANISM: Artificial Sequence
<220> FEATURE:
<223> OTHER INFORMATION: Synthetic Primer

<400> SEQUENCE: 22
gttctttgct cttcggttgc                                               20

<210> SEQ ID NO 23
<211> LENGTH: 25
<212> TYPE: DNA
<213> ORGANISM: Artificial Sequence
<220> FEATURE:
<223> OTHER INFORMATION: Synthetic Primer

<400> SEQUENCE: 23
tagataggga taacagggta atagc                                         25

<210> SEQ ID NO 24
<211> LENGTH: 21
<212> TYPE: DNA
<213> ORGANISM: Artificial Sequence
<220> FEATURE:
<223> OTHER INFORMATION: Synthetic Primer

<400> SEQUENCE: 24
agggctgtac ctcagtttca c                                             21

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
attgcgcatt gttatccaca                                               20

<210> SEQ ID NO 26
<211> LENGTH: 20
<212> TYPE: DNA
<213> ORGANISM: Artificial Sequence
<220> FEATURE:
<223> OTHER INFORMATION: Synthetic Primer

<400> SEQUENCE: 26
taagccctgc cagttctcat                                               20

<210> SEQ ID NO 27
<211> LENGTH: 18
<212> TYPE: DNA
<213> ORGANISM: Artificial Sequence
<220> FEATURE:
<223> OTHER INFORMATION: Synthetic Primer

<400> SEQUENCE: 27
gggctggctc atcaacat                                                 18

<210> SEQ ID NO 28
<211> LENGTH: 20
<212> TYPE: DNA
<213> ORGANISM: Artificial Sequence
<220> FEATURE:
<223> OTHER INFORMATION: Synthetic Primer

<400> SEQUENCE: 28
ctgggtggcc acatagaagt                                               20
```

```
<210> SEQ ID NO 29
<211> LENGTH: 21
<212> TYPE: DNA
<213> ORGANISM: Artificial Sequence
<220> FEATURE:
<223> OTHER INFORMATION: Synthetic Primer

<400> SEQUENCE: 29
gtcagcaaac ccaggagaaa c                                                 21

<210> SEQ ID NO 30
<211> LENGTH: 20
<212> TYPE: DNA
<213> ORGANISM: Artificial Sequence
<220> FEATURE:
<223> OTHER INFORMATION: Synthetic Primer

<400> SEQUENCE: 30
aatccacagt cactgggctg                                                   20

<210> SEQ ID NO 31
<211> LENGTH: 378
<212> TYPE: DNA
<213> ORGANISM: Chicken

<400> SEQUENCE: 31
tctccctctc caggttccct ggtgcaggca gcgctgactc agccggcctc ggtgtcagca       60
aacctgggag gaaccgtcaa gatcacctgc tccgggggtg gcagctatgc tggaagttac      120
tattatggct ggtaccagca gaagtctcct ggcagtgccc ctgtcactgt gatctatgac      180
aacgacaaga gaccctcgga catcccttca cgattctccg gttccctatc cggctccaca      240
aacacattaa ccatcactgg ggtccgagcc gatgacgagg ctgtctattt ctgtgggagt      300
gcagacaaca gtggtgctgc atttggggcc gggacaaccc tgaccgtcct aggtgagtcg      360
ctgacctcgt ctcggtct                                                    378
```

B CELLS MODIFIED TO REVERSIBLY INDUCE ACCELERATED MUTAGENESIS OF TARGET GENES

This application claims benefit of U.S. provisional patent application No. 60/932,672, filed May 31, 2007, the entire contents of which are incorporated by reference into this application.

STATEMENT REGARDING FEDERALLY SPONSORED RESEARCH

This invention was made with U.S. government support under R01 GM041712, awarded by the National Institutes of Health. The U.S. government has certain rights in the invention.

TECHNICAL FIELD OF THE INVENTION

The present invention relates generally to mutagenesis of target genes that takes advantage of the natural mutagenic capabilities of B cells, and enhances those capabilities by bringing the process of diversification under control. The invention provides a method for rapidly and inducibly generating point mutations and other types of diversification in expressed genes, such as antibody genes. This method can be coupled with selection to identify B cell clones that produce, for example, antibodies of high affinity or specificity. The diversification process can be modulated, accelerated, halted, switched between methods of mutagenesis and the like. The modulation of diversification in accordance with the invention is both inducible and reversible. The invention provides a means of rapid and feasible development of a repertoire of variant immunoglobulins and other polypeptides.

BACKGROUND OF THE INVENTION

Antibodies are molecules that provide a key defense against infection in humans. They are used as therapeutics in treatment of a variety of diseases, from infectious disease to cancer. They are also used as diagnostic reagents in a huge variety of tests carried out daily in clinical and research laboratories.

Antibody specificity and affinity are modified in vivo by processes of mutation, targeted to specific regions within the genes that encode antibodies. Antibodies are encoded by two genes, referred to as the immunoglobulin (Ig) heavy and light chain genes. The heavy and light chains of polypeptides encoded by the Ig genes interact to form a tetrameric molecule which is expressed on the cell surface as a receptor. Antibody molecules are bifunctional: one domain recognizes antigen, the other promotes removal of antigen from the body. The recognition domain, referred to as the variable (V) region, is created upon interaction of the heavy and light chain polypeptides in natural antibodies. It is in fact variable in sequence from one antibody to another. Variability in V region primary sequence (and hence three-dimensional structure and antigen specificity) is the result of processes which alter V region sequence by causing irreversible genetic changes. These changes are programmed during B cell development, and can also be induced in the body in response to environmental signals that activate B cells. Several genetic mechanisms contribute to this variability. Two subpathways of the same mechanism lead to two different mutagenic outcomes, referred to as somatic hypermutation and gene conversion (reviewed (Maizels, 2005)). Somatic hypermutation inserts point mutations. Somatic hypermutation provides the advantage of enabling essentially any mutation to be produced, so a collection of mutated V regions has essentially sampled a large variety of possible mutations. Gene conversion inserts mutations that are "templated" by related but non-identical sequences. Gene conversion provides the advantage of creating a repertoire based on information already stored in the genome, which may be optimized by evolutionary selection.

The modified antigen receptor is the target for selection. Ig is expressed on the cell surface, which permits clonal selection of B cells with desired specificity or affinity in a physiological context or within cultured cells. Cell surface Ig can readily be detected by flow cytometry of cells stained with anti-Ig. Binding of Ig molecules to specific compounds can be detected as interaction with fluorescent derivatives of those compounds, analyzed by flow cytometry; and B cells that bind to specific compounds can also be recovered upon sorting by flow cytometry. B cells that bind to specific compounds can also be selected on solid supports carrying those compounds. Conversely, binding to solid support also permits removal of B cells with unwanted binding specificities. Repetitive cycles of binding and release permit enrichment for high affinity binding.

Mutation and gene targeting occur in the DT40 B cell line. DT40 is a chicken B cell line that proliferates readily in culture. DT40 has been widely documented to carry out constitutive mutagenesis of its heavy and light chain immunoglobulin genes (Reynaud et al., 1987; Thompson and Neiman, 1987; Reynaud et al., 1989). Mutagenesis is targeted to the V regions. Mutations are normally templated by copying related non-functional V gene segments, called "pseudo-V" genes, which are present in a linear array upstream of each functional V region. Templating is evident as tracts of sequence shared between the mutated V target and one of the pseudo-V genes. Genetic alterations of DT40 have been shown to cause a switch from templated mutagenesis to non-templated mutagenesis, which results in somatic hypermutation, by a pathway essentially identical to somatic hypermutation that alters the sequences of V regions in human B cells (Sale et al., 2001). DT40 has also been widely documented to support very efficient homologous recombination, or gene targeting (Buerstedde et al., 2002; Sale, 2004). This enables creation of derivatives in which specific genes or genomic regions have been modified or ablated; or in which one genetic region has been replaced with another.

Due to the limitations and challenges posed by currently available approaches to targeted mutagenesis there is a need in the art for the development of alternative methods and constructs. The present invention fulfills this need, and further provides other related advantages.

SUMMARY OF THE INVENTION

The invention meets these needs and others by providing materials and methods for diversification of target sequences. The invention provides a B cell modified to permit reversible induction of diversification of a target gene. The cell comprises a cis-regulatory element operably linked to a target gene of interest. A factor that modulates diversification can then be fused to a tethering factor that binds to the cis-regulatory element, thereby tethering the diversification factor to the region that controls expression of the target gene. The B cell can be a chicken DT40 B cell or other vertebrate B cell, with a human B cell or a chicken DT40 B cell containing humanized immunoglobulin (Ig) genes (in which human IgH and IgL replace chicken IgH and IgL) preferred for some embodiments.

Typically, the target gene comprises a promoter and a coding region. In one embodiment, the target gene comprises an immunoglobulin (Ig) gene, wherein the Ig gene comprises an Ig gene enhancer and coding region. The Ig gene can be all or part of an IgL and/or IgH gene. The coding region can be native to the Ig gene, or a heterologous gene. In some embodiments, the target gene is or contains a non-Ig target domain for diversification, as well as domains permitting display of the gene product on the B cell surface, including a transmembrane domain and a cytoplasmic tail. The coding region of the target gene in the B cell of the invention need not comprise a complete coding region. In some embodiments, a particular region or domain is targeted for diversification, and the coding region may optionally encode only a portion that includes the region or domain of interest.

The cis-regulatory element provides a landing pad in the region that controls diversification and/or expression of the target gene. This landing pad is a place to which a tethering factor can bind in a sequence-specific manner to this region of the DNA. In a typical embodiment, the cis-regulatory element is a polymerized Lactose operator (LacO). In one embodiment, the element comprises about 80-100 repeats of LacO. In another embodiment, the cis-regulatory element is a single or multimerized tetracycline operator (TetO). A variety of molecules can be used as a cis-regulatory element, so long as the element serves the landing pad function of providing a place to which a tethering factor (a sequence-specific DNA binding protein) can bind to the DNA and bring a diversification factor, fused to the tethering factor, into sufficient proximity of the coding region so that diversification of the coding region is capable of reversible regulation.

A tethering factor is one that binds to the cis-regulatory element in a sequence-specific manner. In the embodiments in which LacO serves as a cis-regulatory element, the Lac repressor, LacI, can serve as the tethering factor, and its binding to the cis-regulatory element, LacO, can be regulated by isopropyl-β-D-thio-galactoside (IPTG). In the absence of IPTG, LacI binds LacO and diversification is accelerated (or otherwise regulated) by the presence of the diversification factor. IPTG can be added in the event that a halt or reduction in activity of the diversification factor is desired. In embodiments in which TetO serves as the cis-regulatory element, TetR can be a suitable tethering factor, and the activity of the diversification factor can be regulated by tetracycline or doxycycline.

In some embodiments, the diversification factor is a transcriptional regulator, a heterochromatin-associated protein, a histone chaperone, a chromatin remodeler, a component of the nuclear pore complex, a gene regulator or a combination thereof. Other molecules that can serve as a diversification factor include, but are not limited to, a DNA repair factor, a DNA replication factor, a resolvase, a helicase, a cell cycle regulator, a ubquitylation factor, a sumoylation factor, or a combination thereof. In one embodiment, the transcriptional regulator is VP16 or E47. A typical heterochromatin-associated protein for use as a diversification factor is HP1. A representative histone chaperone is HIRA.

Also provided is a method of producing a repertoire of polypeptides having variant sequences of a polypeptide of interest via diversification of polynucleotide sequences that encode the polypeptide. Typically, the method comprises culturing the B cell of the invention in conditions that allow expression of the diversification factor, wherein the target gene of the B cell contains the coding region of the polypeptide of interest, thereby permitting diversification of the coding region. The method can further comprise maintaining the culture under conditions that permit proliferation of the B cell until a plurality of variant polypeptides and the desired repertoire is obtained.

In another embodiment, the invention provides a method of producing B cells that produce an optimized polypeptide of interest. The method comprises culturing a B cell of the invention in conditions that allow expression of the diversification factor, wherein the target gene of the B cell contains the coding region of the polypeptide of interest, and wherein the B cell expresses the polypeptide of interest on its surface. The method further comprises selecting cells from the culture that express the polypeptide of interest on the B cell surface by selecting cells that bind a ligand that specifically binds the polypeptide of interest. These steps of culturing and selecting can be repeated until cells are selected that have a desired affinity for the ligand that specifically binds the polypeptide of interest. In embodiments in which the polypeptide of interest is an Ig, such as an IgL, IgH or both, the ligand may be a polypeptide, produced by recombinant or other means, that represents an antigen. The ligand can be bound to or linked to a solid support to facilitate selection, for example, by magnetic-activated cell selection (MACS). In another example, the ligand can be bound to or linked to a fluorescent tag, to allow for or fluorescence-activated cell sorting (FACS).

The methods of the invention can further comprise adding a regulatory molecule to the culture, wherein the regulatory molecule modulates binding of the tethering factor to the cis-regulatory element, thereby modulating diversification of the coding region. In the examples discussed above, IPTG, tetracycline and doxycycline serve as the regulatory molecules. Those skilled in the art are aware of other regulatory molecules that can be used with a particular tethering factor to regulate diversification activity.

The regulatory molecule can modulate the diversification of the coding region in a variety of ways. For example, in some embodiments, the regulatory molecule is added to the culture to effect modulation, and the modulation can result in reducing or halting diversification, or in enhancing or accelerating diversification, depending on whether the particular regulatory molecule is one that increases or decreases binding of the tethering factor to the cis-regulatory element, and on whether that particular change in binding has the effect of increasing or decreasing diversification activity. In other embodiments, the modulation, be it reduction, halt or enhancement or acceleration of the modulation, is effected by removing or eliminating the regulatory molecule from the culture. Likewise, modulation of diversification can be effected by adding a gene to or eliminating a gene from the B cell, or by increasing or diminishing the expression of a gene in the B cell. One skilled in the art can readily appreciate all of the available permutations set forth above, each of which has the effect of altering the level or presence of a regulatory molecule in the B cell, and in turn, altering the tethering of the diversification factor to the cis-regulatory element and thereby altering the diversification activity.

Also provided is a kit that can be used to carry out the methods of the invention. The kit comprises a B cell of the invention and fusion constructs that express the corresponding tethering and diversification factors. For example, the B cell comprises a cis-regulatory element operably linked to a target gene, wherein the target gene comprises a promoter and a coding region. The kit further comprises one or more containers, with one or more fusion constructs stored in the containers. Each fusion construct comprises a polynucleotide that can be expressed in the B cell and that encodes a tethering factor fused to a diversification factor, wherein the tethering factor specifically binds to the cis-regulatory element of the B cell. The B cell can include a plurality of cis-regulatory elements for use with a plurality of fusion constructs.

BRIEF DESCRIPTION OF THE FIGURES

FIG. 4A: Schematic of the rearranged and unrearrranged Igλ loci in the chicken B cell lymphoma line, DT40. Shown are promoter (P), leader (L), variable (V), joining (J) and constant (Cλ) regions; the putative matrix attachment region (M) in the J-C intron; the 3'-enhancer (E-3'); and the most proximal (ΨV1) and distal (ΨV25) of the upstream nonfunctional pseudo-variable regions which are templates for gene conversion. The rearranged and unrearranged alleles can readily be distinguished by PCR, using primers indicated by arrows. FIG. 4B: ChIP analysis of E2A enrichment at the rearranged λR and unrearranged λU loci in DT40 cells, relative to ovalbumin gene control amplicon (Ova). Fold enrichment is shown below. NTC, no template control.

FIG. 5A-F. E2A acts in cis to regulate Igλ gene diversification. FIG. 5A: Schematic of the PolyLacO-tagged rearranged Igλ locus. PolyLacO is integrated between ΨV17-20; other notions as in FIG. 4A. FIG. 5B: Cell cycle profile of DT40 and DT40 PolyLacO-λR cells. FIG. 5C: Accumulation of sIgM-loss variants by DT40 and DT40 PolyLacO-λR cells. Frequencies of sIgM-loss variants in 24 subclones from each line were quantitated by flow cytometry following 6 wk clonal expansion. Frequencies shown were normalized to DT40; mean sIgM-loss frequencies were 0.8% and 0.9%, respectively. FIG. 5D: Cell cycle profile of DT40 PolyLacO-λR GFP-LacI and DT40 PolyLacO-λR E47-LacI cells. FIG. 5E: RT-PCR analysis of expression of Igλ, AID or β-actin mRNAs in DT40 PolyLacO-λR GFP-LacI and DT40 PolyLacO-λR E47-LacI transfectants. Triangles indicate 30, 10, 3 and 1× relative concentrations of cDNA templates. FIG. 5F: Mean sIgM loss of independent clonal DT40 PolyLacO-λR GFP-LacI (n=13) and DT40 PolyLacO-λR E47-LacI (n=19) transfectants, cultured for 3 wk in the absence or presence of 100 μM IPTG. Values were normalized to DT40 PolyLacO-λR GFP-LacI cells cultured without IPTG.

FIG. 6A-B. Nuclear radius correlates with cell cycle. FIG. 6A: Representative images of G1- and G2/M-enriched cells. G1 (left) and G2/M (right) cells were stained with Hoechst 33342 (10 μM; Molecular Probes) then sorted based on DNA content. Bar, 10 μm. FIG. 6B: Representative cell cycle profile of DT40 PolyLacO-λR cells. Mean radii±s.d. are shown as horizontal bars within the representative profile. Dotted vertical lines indicate cut-offs for G1 and G2 used in experimental analyses: G1, r<4 μm; G2, r>5.2 μm.

FIG. 7A-D. E2A localizes to λR in G1 phase of cell cycle. FIG. 7A: Representative image of colocalization of λR and E2A in DT40 PolyLacO-λR GFP-LacI cells. Nuclear perimeter as determined by DAPI staining is outlined by the dashed white line. Bar, 5 μm. FIG. 7B: Fraction of λR/E2A colocalizations occurring in each phase of cell cycle in DT40 PolyLacO-λR GFP-LacI cells. FIG. 7C: Representative image of colocalization of λR and active Pol II (P*-Pol II) in DT40 PolyLacO-λR RFP-LacI cells. Notations as in 7A. FIG. 7D: Fraction of λR/P*-Pol II colocalizations occurring in each phase of cell cycle in DT40 PolyLacO-λR RFP-LacI cells.

FIG. 8A: Western blot assaying Id1 expression in DT40 PolyLacO-λR RFP-LacI (left) and DT40 PolyLacO-λR RFP-LacI Id1 cells (right). Marker polypeptide sizes (kDa) at left. FIG. 8B: Cell cycle profile of DT40 PolyLacO-λR RFP-LacI and DT40 PolyLacO-λR RFP-LacI Id1 cells. FIG. 8C: Mean sIgM loss of independent clonal DT40 PolyLacO-λR RFP-LacI Id1 transfectants (n=6), cultured for 6 wk. Values were normalized to DT40 PolyLacO-λR RFP-LacI cells. FIG. 8D: Id1 expression does not alter Igλ or AID transcript levels. RT-PCR analysis of expression of Igλ, AID or β-actin control mRNA in DT40 PolyLacO-λR REP-Lad and DT40 PolyLacO-λR RFP-LacI Id1 cells. FIG. 8E: Effect of Id1 expression on cell cycle-dependence of λR/E2A colocalizations in DT40 PolyLacO-λR RFP-LacI cells and a derivative stably expressing Id1 (Id1 − and +, respectively). Percent of colocalizations in each stage of cell cycle is shown. FIG. 8F: Effect of Id1 expression on cell cycle-dependence of colocalizations of λR/P*-Pol II colocalizations and in DT40 PolyLacO-λR RFP-LacI cells and a derivative stably expressing Id1. Details as in 8E.

FIG. 9A: Schematic diagram of the rearranged chicken Igλ locus, showing the 25 ΨVλ regions and the rearranged VλR gene (leader, L; variable region, Vλ-Jλ; constant region, Cλ region. FIG. 9B: Summary of a representative chromatin immunoprecipitation experiment, assaying N-terminal acetylation of histones H3 and H4 (AcH3 and AcH4). Sites interrogated were: a region approximately 1 kb upstream of the ΨVλ array (flank); the region between ΨVλ5 and Vλ; ΨVλ1; ΨVλ5; ΨVλ13; ΨVλ18; ΨVλ24; ΨVλ25; and the rearranged VλR and unrearranged Vλu alleles. See Materials and Methods for details. Bars indicate standard deviation.

FIG. 10A: Schematic diagram of the rearranged chicken Igλ locus in DT40, with polymerized lactose operator (PolyLacO) inserted between ΨVλ17-20. Notations as in FIG. 9. FIG. 10B: Fluorescent images of DT40 GFP-LacI transfectants and DT40 PolyLacO-VλR GFP-LacI transfectants cultured in the absence of IPTG (left); or in the presence of 100 μM IPTG overnight (right).

FIG. 11A: Representative fluorescent images of single DT40 PolyLacO-VλR LacI-HP1 transfectants, stained with anti-LacI antibodies (left); DAPI (center); or merged image (right). FIG. 11B: Enrichment of acetylated H3 (AcH3) and H4 (AcH4) at ΨVλ17R in DT40 PolyLacO-VλR GFP-LacI and DT40 PolyLacO-VλR LacI-HP1 transfectants. Following ChIP, duplex PCR was carried out with Ova and ωVλ17R primers. Enrichment is expressed relative to the total DNA input control, ±standard deviation of four separate amplifications of increasing amounts of template DNA. FIG. 11C: Histogram showing enrichment of AcH3 and AcH4 at ΨVλ17R (from panel B) and the pol ε promoter in DT40 PolyLacO-VλR GFP-LacI and DT40 PolyLacO-VλR LacI-HP1 transfectants. Bars indicate standard deviation.

FIG. 12A: Relative enrichment of AcH3 and AcH4 at VλR in DT40 PolyLacO-VλR GFP-LacI and DT40 PolyLacO-VλR LacI-HP1 transfectants. Enrichment values were normalized to the DT40 PolyLacO-VλR GFP-LacI control. Bars indicate standard deviation of four separate amplifications of increasing amounts of template DNA. FIG. 12B: Relative intensity of cell surface IgM (sIgM) expression in DT40 PolyLacO-λR GFP-LacI (GFP-LacI) and DT40 PolyLacO-λR LacI-HP1 (LacI-HP1) transfectants cultured in the presence and absence of 250 μM IPTG. sIgM levels were quantitated by measuring intensity of staining with mouse anti-chicken IgM antibody, and normalized to the level in DT40 PolyLacO-λR GFP-LacI transfectants. Details as in 12A. FIG. 12C: Relative levels of VλR transcripts in DT40 PolyLacO-λR GFP-LacI (GFP-LacI) and DT40 PolyLacO-λR LacI-HP1 (LacI-HP1) transfectants. Transcript levels were quantitated by RT-PCR and normalized to the level in DT40 PolyLacO-λR GFP-LacI transfectants. Details as in 12A.

FIG. 13A: Summary of a chromatin immunoprecipitation experiment, assaying N-terminal acetylation of histone H3 in chromatin from the DT40 PolyLacO-VλR LacI-HP1 cell line cultured for 3 days in the presence and absence of 250 μM IPTG. ChIP enrichment values (see Example 4) were normalized to values obtained from a parallel analysis of chromatin from DT40 PolyLacO-VλR GFP-LacI cells. Bars indicate standard deviation of four separate amplifications of increasing amounts of template DNA. FIG. 13B: Summary of a chromatin immunoprecipitation experiment, assaying N-terminal acetylation of histones H4 in chromatin from the DT40 PolyLacO-VλR LacI-HP1 cell line cultured for 3 days in the presence and absence of 250 μM IPTG. Details as in 13A.

FIG. 14A-E. Nontemplated and Templated Mutation Promoted by Tethered HP1. FIG. 14A: sIgM loss fluctuation assay of panels of independent DT40 PolyLacO-VλR GFP-LacI (n=27) and DT40 PolyLacO-VλR LacI-HP1 (n=16). The figure shows combined data from at least two independent transfectants for each fusion construct. Median diversification rates are shown below. FIG. 14B: Summary of sequence analysis of Vλ regions carrying unique mutations, from DT40 PolyLacO-VλR GFP-LacI (n=78) and DT40 PolyLacO-VλR LacI-HP1 (n=36) transfectants, as analyzed by single cell PCR. Sequences were pooled from two independent transfectants.

Figure 15:
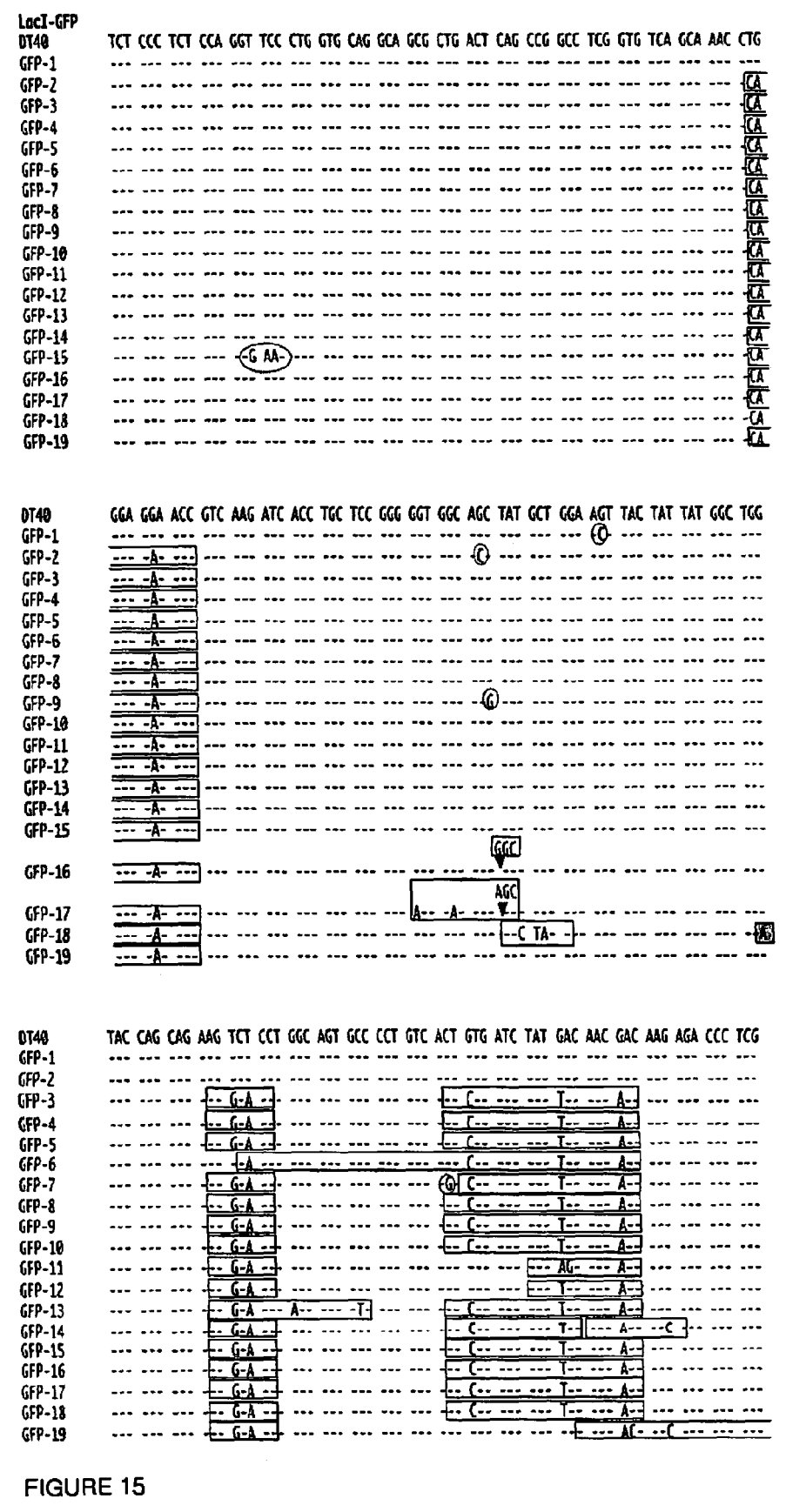

FIG. 15. Sequence Alignment of Mutated DT40 PolyLacO-λR LacI-HP1 Clones. Sequences of 14 unique, mutated VX regions from diversified DT40 PolyLacO-λR LacI-HP1 cells. Blue boxes outline gene conversion tracts; red circles denote point mutations; black dotted boxes indicate nontemplated insertions; orange triangles denote deletions. Parent sequence of DT40 region (SEQ ID NO: 31) is presented, with mutation sites indicated.

FIG. 16A: Schematic diagram of the rearranged chicken IgA locus in DT40, with polymerized lactose operator (PolyLacO) inserted between ΨVλ17-20. Leader, L; rearranged variable region, Vλ-Jλ; constant region, Cλ. FIG. 16B: Western blot analysis of expression of GFP-LacI or GFP-LacI-VP16 in indicated transfectants. Expression was assayed by blotting with anti-LacI antibodies, relative to β-actin control. FIG. 16C: Cell cycle profile of DT40 PolyLacO-λ GFP-LacI and DT40 PolyLacO-λ GFP-LacI-VP16 transfectants. FIG. 16D: Quantitation of RT-PCR comparison of Vλ transcript levels in DT40 PolyLacO-λ GFP-LacI and DT40 PolyLacO-λ GFP-LacI-VP16 transfectant, normalized to DT40 PolyLacO-λ GFP-LacI. FIG. 16E: Fluorescent image of DT40 PolyLacO-λ GFP-LacI-VP16 transfectants. Arrows indicate GFP-LacI-VP16 bound to Igλ. Nuclei were counterstained with DAPI (blue).

FIG. 17A: Enrichment of acetylated H3 (AcH3) at Igλ in DT40 PolyLacO-λ GFP-LacI-VP16 transfectants. Following ChIP, duplex PCR was carried out with Ova and ΨVλ17R primers. Enrichment is expressed relative to the total DNA input control, ±standard deviation of four separate amplifications of increasing amounts of template DNA. FIG. 17B: Enrichment of acetylated H4 (AcH4) at Igλ in DT40 PolyLacO-λ GFP-LacI-VP16 transfectants. Notations as in 17A. FIG. 17C: Median sIgM loss in panels of independent DT40 PolyLacO-λ GFP-LacI-VP16 transfectants, normalized to DT40 PolyLacO-Vλ GFP-LacI transfectants. The figure shows combined data from at least two independent transfectants for each fusion construct. The fold increase relative to control DT40 PolyLacO-Vλ GFP-LacI transfectants is shown below.

FIG. 18A: Schematic diagram of the rearranged chicken Igλ locus in DT40. Notations as in FIG. 16A. FIG. 18B: Summary of a representative chromatin immunoprecipitation experiment, assaying the H3.3 histone variant. Sites interrogated were: a region approximately 1 kb upstream of the ΨVλ array (flank); the region between ΨVλ5 and Vλ; ΨVλ1; ΨVλ5; ΨVλ13; ΨVλ18; ΨVλ24; ΨVλ25; and the rearranged VλR allele. Bars indicate standard deviation.

FIG. 19A-E. Ig gene conversion is accelerated by HIRA tethered to the ΨVλ array. FIG. 19A: Western blot analysis of expression of GFP-LacI or HIRA-LacI in indicated transfectants. Expression was assayed by blotting with anti-LacI antibodies, relative to β-actin control. FIG. 19B: Cell cycle profile of DT40 PolyLacO-λ GFP-LacI and DT40 PolyLacO-λ HIRA-LacI transfectants. FIG. 19C: Quantitation of RT-PCR comparison of VX transcript levels in DT40 PolyLacO-λ GFP-LacI and DT40 PolyLacO-λ HIRA-LacI transfectants, normalized to DT40 PolyLacO-λ GFP-LacI. FIG. 19E: Fluorescent image of DT40 PolyLacO-λ GFP-LacI-VP16 transfectants. Arrows indicate GFP-LacI-VP16 bound to Igλ. Nuclei were counterstained with DAPI (blue).

FIG. 20A: Enrichment of H3.3 (green) and pan H3 (blue) at ΨVλ17R in DT40 PolyLacO-λ, and DT40 PolyLacO-λ HIRA-LacI cells expressing H3.3-FLAG. Results for two independent lines of DT40 PolyLacO-λ HIRA-LacI are shown. Enrichment of DT40 PolyLacO-λ is normalized to a value of "1". Bars are shown±standard deviation of four separate amplifications of increasing amounts of template DNA. FIG. 20B: Flow cytometry of sIgM+ cells in representative populations of DT40 PolyLacO-GFP-LacI cells and DT40 PolyLacO-λHIRA-LacI cells. FIG. 20C: Median sIgM loss in panels of independent DT40 PolyLacO-λHIRA-LacI, and DT40 HIRA transfectants, normalized to DT40 PolyLacO-λ GFP-LacI transfectants. The figure shows combined data from at least two independent transfectants for each fusion construct. The fold increase relative to control DT40 PolyLacO-λ GFP-LacI transfectants is shown below.

FIG. 21A: Southern blot analysis of the PolyLacO region in DT40 PolyLacO-λ GFP-LacI, DT40 PolyLacO-λ GFP-LacI-VP16 and DT40 PolyLacO-λ HIRA-LacI transfectants, following digestion of chromatin with micrococcal nuclease (MNase). No MNase, (–). Numbers at the right denote nucleosome multimers. FIG. 20B: Model of how elevated histone deposition could be responsible for an accentuated "laddering" pattern of chromatin. Arrowheads indicate possible MNase cleavage sites. Dark arrowheads indicate a restricted range of cleavable DNA, and grey arrowheads suggest a large range of cleavable DNA to generate deviations from the predicted ~150 bp cleavage product.

FIG. 23. Sequences of mutated V regions from single DT40 PolyLacO-λ HIRA-LacI cells. Notations as in FIG. 22.

DETAILED DESCRIPTION OF THE INVENTION

Figure 1:
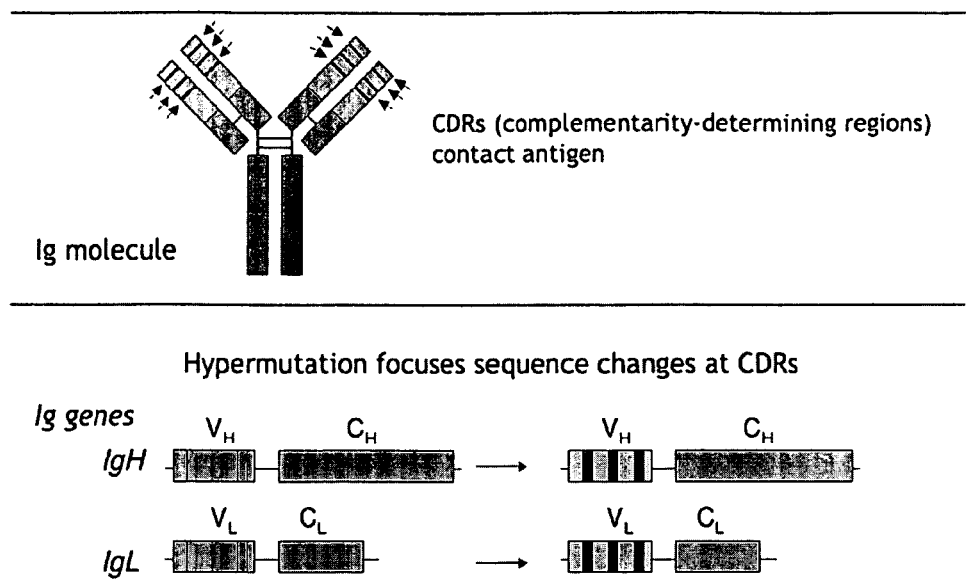
FIG. 1. Schematic illustration of antibody somatic hypermutation. Upper panel: the complementarity-determining regions (CDRs) of an Ig molecule contact antigen. Lower panel: mutations are concentrated at the genomic regions encoding the CDRs.

The present invention is based on the development of B cell lines in which mutagenesis of a target immunoglobulin gene is inducible. Immunoglobulin is expressed on the cell surface, permitting selection for clones that express immunoglobulin molecules with particular specificities, increased affinities, and/or new activities. This can be carried out with immunoglobulin and also non-immunoglobulin genes at the target site.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Peptides of the invention typically comprise at least about 6 amino acids.

As used herein, "diversification" of a target gene means a change or mutation in sequence or structure of the target gene. Diversification includes the biological processes of somatic hypermutation, gene conversion, and class switch recombination, which can result in point mutation, templated mutation DNA deletion and DNA insertion. The diversification factors of the invention can induce, enhance or regulate any of these methods of diversification.

A "mutation" is an alteration of a polynucleotide sequence, characterized either by an alteration in one or more nucleotide bases, or by an insertion of one or more nucleotides into the sequence, or by a deletion of one or more nucleotides from the sequence, or a combination of these.

As used herein, a "cis-regulatory element" is a DNA sequence positioned in a region that controls expression or diversification of a gene. A tethering factor binds in a sequence-specific manner to this region of the DNA. Representative cis-regulatory elements include, but are not limited to, LacO and TetO.

As used herein, a "tethering factor" is a molecule that binds to the cis-regulatory element in a sequence-specific manner. One example of a tethering factor is a "repressor", a protein that is synthesized by a regulator gene and binds to an operator locus, blocking transcription of that operon. Exemplary tethering factors include, but are not limited to, LacI and TetR.

As used herein, a "diversification factor" refers to a molecule that accelerates or regulates diversification or hypermutation. Representative diversification factors include some identified initially as transcriptional regulators (e.g., VP16 or E47), a heterochromatin-associated protein (e.g., HP1), a histone chaperone (HIRA), a chromatin remodeler, a component of the nuclear pore complex (NUP153), a gene regulator or a combination thereof. Other molecules that can serve as a diversification factor include, but are not limited to, a DNA repair factor, a DNA replication factor, a resolvase, a helicase, a cell cycle regulator, a ubquitylation factor, a sumoylation factor, or a combination thereof.

As used herein, "promoter" means a region of DNA, generally upstream (5') of a coding region, which controls at least in part the initiation and level of transcription. Reference herein to a "promoter" is to be taken in its broadest context and includes the transcriptional regulatory sequences of a classical genomic gene, including a TATA box or a non-TATA box promoter, as well as additional regulatory elements (i.e., activating sequences, enhancers and silencers) that alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene, although they may also be many kb away. Promoters may contain additional specific regulatory elements, located more distal to the start site to further enhance expression in a cell, and/or to alter the timing or inducibility of expression of a structural gene to which it is operably connected.

As used herein, "operably connected" or "operably linked" and the like is meant a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame. "Operably linking" a promoter to a transcribable polynucleotide is meant placing the transcribable polynucleotide (e.g., protein encoding polynucleotide or other transcript) under the regulatory control of a promoter, which then controls the transcription and optionally translation of that polynucleotide.

The term "nucleic acid" or "polynucleotide" refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides.

As used herein, "a" or "an" means at least one, unless clearly indicated otherwise.

B Cells

The invention provides a B cell modified to permit reversible induction of diversification of a target gene. The cell comprises a cis-regulatory element operably linked to a target gene of interest. A factor that modulates diversification can then be fused to a tethering factor that binds to the cis-regulatory element, thereby tethering the diversification factor to the region that controls expression of the target gene. The B cell can be a chicken DT40 B cell or other vertebrate B cell, with a human B cell or a chicken DT40 B cell containing humanized immunoglobulin (Ig) genes (in which human IgH and IgL replace chicken IgH and IgL) preferred for some embodiments.

B cells are natural producers of antibodies, making them an attractive cell for production of both improved antibodies and improved non-immunoglobulin proteins and polypeptides. DT40 B cells are an effective starting point for evolving specific and high affinity antibodies by iterative cycles of hypermutation and selection (Cumbers et al., 2002; Seo et al., 2005). DT40 cells have several advantages over other vehicles tested for this purpose. DT40 constitutively diversifies its Ig genes in culture, and targets mutations to the CDRs of the expressed antibody molecules. DT40 proliferates more rapidly than human B cell lines (10-12 hr generation time, compared to 24 hr); clonal populations can be readily isolated because cells are easily cloned by limiting dilution, without addition of special factors or feeder layers; and DT40 carries out efficient homologous gene targeting (Sale, 2004), so specific loci can be replaced at will allowing one to manipulate factors that regulate hypermutation.

The invention provides a novel platform for generating high affinity antibodies. In one embodiment, the vehicle for antibody evolution is a B cell line, DT40, which naturally produces antibodies, and which has been engineered to make immunoglobulin gene hypermutation accelerated and inducible. Like other B cells, DT40 expresses antibodies on the cell surface, allowing convenient clonal selection for high affinity and optimized specificity, by fluorescence or magnetic-activated cell sorting. In the DT40 cell line, hypermutation is carried out by the same pathway that has been perfected over millions of years of vertebrate evolution to Ig gene hypermutation in a physiological context. This highly conserved pathway targets mutations preferentially (though not exclusively) to the complementarity-determining regions (CDRs), the subdomains of the variable (V) regions that make contact with antigen (FIG. 1).

Thus far, the use of DT40 (and other cultured B cell lines) for antibody selection has been limited because the rate of hypermutation is very slow, about 0.1%-1% that of physiological hypermutation. To accelerate hypermutation, key regulatory sites and factors have been manipulated, taking advantage of our current sophisticated understanding of the molecular mechanisms of hypermutation.

Although chicken DT40 B cells offer many advantages, in some embodiments it may be desired to use human B cells. Alternatively, one can employ humanized Ig genes with the chicken DT40 B cells. By humanizing the DT40 immunoglobulin genes, the utility of this platform for therapeutics can be broadened, as the antibodies generated in the DT40 platform could be used directly for treatment.

There is ample documentation of the utility of humanized antibody genes, and a number of validated approaches for humanization, as reviewed recently (Waldmann and Morris, 2006; Almagro and Fransson, 2008). Humanization is effected by substitution of human Ig genes for the chicken Ig genes, and this is readily done in DT40 by taking advantage of the high efficiency of homologous gene targeting. The substitutions are carried out by procedures analogous to those described in the examples below to insert cis-regulatory elements, but using different targeting constructs that are designed to modify distinct parts of the heavy and light chain loci. Substitution could produce DT40 derivatives that generate entirely humanized antibodies, by swapping V(D)J and C regions; or chimeric antibodies (humanized C regions but not V regions). These replacements will not alter the adjacent cis-regulatory elements or affect their ability to accelerate hypermutation. The conserved mechanisms that promote hypermutation will target mutagenesis to the CDRs of humanized sequences. The humanized line can thus be used for accelerated development of human monoclonals in cell culture, providing a dual platform for rapid production of useful antibodies for either therapeutic or diagnostic purposes.

In addition, one can optimize antibody effector function by C region replacement. Antibody-based immunotherapy is a powerful approach for therapy, but this approach thus far been limited in part by availability of specific antibodies with useful effector properties (Hung et al., 2008; Liu et al., 2008). The constant (C) region of an antibody determines effector function. Substitutions of either native or engineered human C regions can be made by homologous gene targeting in the DT40 vehicle to generate antibodies with desired effector function.

Target Genes

Typically, the target gene comprises a promoter and a coding region. The coding region of the target gene in the B cell of the invention can be one that encodes any protein or peptide of interest, and need not comprise a complete coding region. In some embodiments, a particular region or domain is targeted for diversification, and the coding region may optionally encode only a portion that includes the region or domain of interest.

In one embodiment, the target gene comprises an immunoglobulin (Ig) gene, wherein the Ig gene comprises an Ig gene enhancer and coding region. The Ig gene can be all or part of an IgL and/or IgH gene. The coding region can be native to the Ig gene, or a heterologous gene. In some embodiments, the target gene is or contains a non-Ig target domain for diversification, as well as domains permitting display of the gene product on the B cell surface, including a transmembrane domain and a cytoplasmic tail.

Cis-Regulatory Element

The cis-regulatory element provides a landing pad in the region that controls expression of the target gene. This landing pad provides a place to which a tethering factor can bind in a sequence-specific manner to this region of the DNA. A variety of molecules can be used as cis-regulatory elements, so long as the element serves the landing pad function of providing a place to which a tethering factor (a sequence-specific DNA binding protein) can bind to the DNA and bring a diversification factor, fused to the tethering factor, into sufficient proximity of the coding region so that diversification of the coding region is capable of reversible regulation. In a typical embodiment, the cis-regulatory element is a polymerized Lactose operator (LacO). In one embodiment, the element comprises about 80-100 repeats of LacO. In another embodiment, the cis-regulatory element is a tetracycline operator (TetO).

Tethering & Diversification Factors

A tethering factor is one that binds to the cis-regulatory element in a sequence-specific manner. In some embodiments, regulation of diversification is achieved by using a tethering factor characterized by regulatable binding to the cis-regulatory element. In the embodiments in which LacO serves as a cis-regulatory element, the Lac repressor, LacI, can serve as the tethering factor, and its binding to the cis-regulatory element, LacO, can be regulated by isopropyl-β-D-thio-galactoside (IPTG). In the absence of IPTG, LacI binds LacO and diversification is accelerated (or otherwise regulated) by the presence of the diversification factor. IPTG can be added in the event that a halt or reduction in activity of the diversification factor is desired, thereby making the mutagenesis process a reversible one. In embodiments in which TetO serves as the cis-regulatory element, TetR can be a suitable tethering factor, and the activity of the diversification factor can be regulated by tetracycline or doxycycline.

Figure 2:
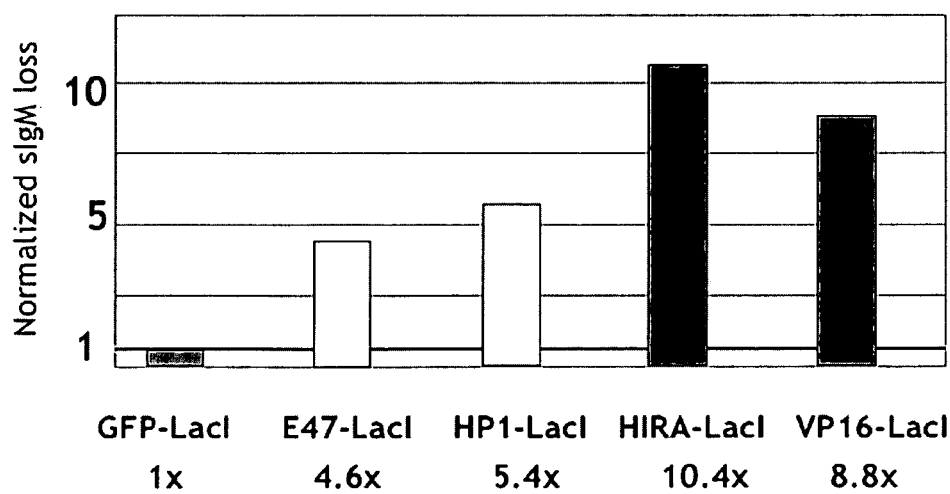
FIG. 2. Bar graph showing the effect of tethered cis-regulators on Ig gene diversification in DT40 PolyLacO λ cells. Clonal diversification rates were compared in the presence and absence of IPTG.

A diversification factor is one that enables modulation of mutagenesis in the B cell. The examples below describe the effects of tethering and releasing several regulatory factors. One, the heterochromatin protein HP1, accelerated hypermutation 5.6-fold (Example 4); another, E47-LacI (E47 is one isoform of the E2A regulator, critical to B cell development), accelerated hypermutation 4.5-fold (Example 3); and two other modifiers of chromatin structure accelerated hypermutation 8.4-fold and 11.0-fold (FIG. 2). In addition, a tethering site has been targeted to the expressed Ig heavy chain locus. Dual regulation of hypermutation at IgH and IgL can accelerate hypermutation from 25- to 100-fold, enabling rapid production of new antibodies.

Diversifying immunoglobulin genes move within the nucleus in the course of cell cycle, and this movement is correlated with and necessary for diversification. Tethering to the nuclear pore by expression of NP153-LacI in DT40 Poly-LacO-λ cells (using methods described in the examples below) accelerates diversification 5.7-fold. This result predicts that other factors that regulate gene position also regulate diversification, including other nuclear pore proteins and other factors that determine or regulate gene position in the nucleus.

Chromatin structure regulates diversification as well. The data in Example 4 show that expression of the heterochromatin protein HP1 fused to LacI accelerates diversification and that this effect is reversible by IPTG. This finding has been extended to the histone chaperone, HIRA.

Regulators of gene expression or function also serve as diversification factors. Example 3 below shows that expression of the regulatory factor E2A (expressed as the E47 isoform, as a LacI fusion) accelerates diversification, and that this effect is reversible by IPTG. The VP16 regulatory domain from herpes virus accelerates diversification, and that this effect is reversible by IPTG.

Deamination also accelerates mutagenesis, but it is not inducible. AID is the B cell-specific DNA deaminase that initiates Ig gene diversification. Example 2 below shows that tethering AID (AID-LacI) in DT40 PolyLacO-λ promotes mutagenesis, but that IPTG does not overcome this effect. Thus, it appears that mutagenic affects are genome-wide, making this factor unsuitable without further modification.

In some embodiments, the diversification factor is a transcriptional regulator, a heterochromatin-associated protein, a histone chaperone, a chromatin remodeler, a component of the nuclear pore complex, a gene regulator or a combination thereof. Other molecules that can serve as a diversification factor include, but are not limited to, a DNA repair factor, a DNA replication factor, a resolvase, a helicase, a cell cycle regulator, a ubquitylation factor, a sumoylation factor, or a combination thereof. In one embodiment, the transcriptional regulator is VP16 or E47. A typical heterochromatin-associated protein for use as a diversification factor is HP1. A representative histone chaperone is HIRA.

TABLE 1

Representative Diversification Factors
Transcriptional activators

| | | | |
|---|---|---|---|
| VP16 | NeuroD | TFIIB | A13, B1, |
| E47 | NPAS | TFIID | B2, B3, |
| E12 | OLIG | TFIIE | B4, B5, B6, |
| Myc | TAL1 | TFIIF | B7, |
| c-Fos | Twist | TFIIH | B8, B9, B13, |
| c-Jun | USF1 | GFI1 | C4, |
| BACH | MAX | HIC | C5, C6, C8, |
| BATF | MITF | HIVEF | C9, |
| BLZF1 | MNT | IKZF | C10, C11, |
| C/EBP | MLX | ILF | C13, D1, D3, |
| CREB | MXI1 | KLF | D4, D8, D9, |
| CREM | SREBP | MTF1 | C10, D11, |
| DBP | AP-2 | MYT1 | D12, D13) |
| DDIT3 | CAR | OSR1 | HOPX |
| GABPA | FXR | Sp1 | MEIS |
| HLF | LXR | Zbtb7 | MEOX2 |
| MAF | PPAR | ZB1 | MNX1 |
| NFE | PXR | HIVEP1 | MSX |
| NRL | RAR | AIRE | NANOG |
| NRF1 | ROR | DIDO1 | NKX |
| XBP1 | Rev-ErbA | GRLF1 | PHF |
| ATOH1 | HNF4 | ING | POU domain |
| AhR | PNR | JARID | proteins |
| AHRR | RXR | JMJD1B | OTX |
| ARNT | NUR | ARX | PDX |
| ASCL1 | GCNF | CDX | PAX |
| BHLHB2 | DAX1 | CRX | E2F (1-5) |
| BMAL | GATA | CUTL1 | FOX |
| CLOCK | ATBF1 | DLX | proteins |
| EPAS1 | CTCF | EMX2 | HSF |
| HAND | E4F1 | EN | ELF |
| HES | EGR | FHL | EGF |
| HEY | ERV3 | ESX1 | ELK |
| HIF | ATBF1 | HHEX | ERF |
| ID | BCL | HLX | ERG |
| LYL1 | CTCF | Homeobox | ETS |
| MXD4 | E4F1 | (A1, A3, A4, | ETV |
| MYCL1 | EGR | A5, | FLI1 |
| MYCN | ERV3 | A7, A9, A10, | MYB |
| MyoD | TFIIA | A11, | MYBL2 |
| NFAT | SRY | RBL2 | NF-κB |
| STAT | SSRP1 | Apetala 2 | NFI |
| Mef2 | CSDA | EREBP | NFY |
| SRF | YBX1 | B3 | Rho/Sigma |
| HNF (1A, | CBF | ARID | R-SMAD |
| 1B) | HMGA | CAP | |
| LEF1 | HBP1 | IFI | |
| SOX | Rb | MLL | |
| | RBL1 | MNDA | |

| Heterochromatin-associated proteins | Histone chaperones | Chromatin remodelers |
|---|---|---|
| HP1 a | Polycomb proteins | Nucleolin |
| HP1b | Trithorax proteins | Rtt106 |
| HP1c | HIRA | NAP1 |
| | ASF1a | NAP2 |
| | ASFb | |
| | CAF1 | |
| | Spt6 | |

| | | | |
|---|---|---|---|
| DNA repair | XRCC2 | HAP1 | CSB |
| BRG1 | DMC1 | APE1 | XPV |
| BAF | RAD52 | DNA | EndoV |
| PBAF | RecA | polymerase | MSH2 |
| BRM | RecB | b | MSH3 |
| Rdh54 | RecC | DNA Ligase | MSH5 |
| XRCC3 | RecD | I | MSH6 |
| FANCD2 | MRE11 | XRCC1 | MLH1 |
| FANCI | RAD50 | PARP | PMS2 |
| CtIP | XRS2/NBS1 | XPA | EXO1 |
| Rad54 | KU70 | XPB | POLH |
| Rad51 | KU80 | XPC | POLI |
| BRCA1 | SAE2 | XPD | REV1 |
| BRCA2 | DNA-PK | XPE | POLQ |
| RAD51B | DNA Ligase | XPF | |
| RAD51C | iV | XPG | |
| RAD51D | UNG | CSA | |

| DNA Replication | Resolvases and Helicases | Cell cycle regulators |
|---|---|---|
| PCNA | RuvC | CHK1 |
| RPA | RusA | CHK2 |
| Smc1 | RuvB | p53 |
| Smc3 | RuvC | p27 |
| Rad21/Mcd1/Scc1 | RecQ | |
| Stromalin/Scc3 | hRECQ5 | |

TABLE 1-continued

| | | | |
|---|---|---|---|
| Scc2 | WRN | | |
| Scc4 | BLM | | |
| Pds5 | Srs2 | | |
| Eco1 | hRECQ1/L | | |
| Rec8 | RTS/hRECQ4 | | |

| Gene | HASPIN | MLL3 | SET1A |
|---|---|---|---|
| Regulation | MLL1 | MLL4 | SET1B |
| CARM1 | MLL2 | MLL5 | SET7/9 |
| ASH1 | JMD2A/JHDM | NSD1 | Sc ESA1 |
| LSD/BHC110 | 3A | SMYD2 | SIRT2 |
| PRMT5 | JMJD2B | SET2 | SIR2 |
| SUV39H1 | JMJD2C/GAS | JHDM1a | SUV4-20H1 |
| SUV39H2 | C1 | JHDM1b | SUV4-20H2 |
| SETDB1/ESE | JMJ2D2D | Sc RTT109 | PR-SET7/8 |
| T | JHDM2a | DOT1 | SET9 |
| EuHMTase/GL | JHDM2b | CKII | Bmi/Ring1A |
| P | AuroraB | PRMT4 | MST1 |
| G9a | CBP/p300 | PRMT5 | RNF20/RNF40 |
| CLL8 | EZH2 | HBO1 | UbcH6 |
| RIZ1 | MSK1 | Sc HAT1 | |
| PCAF | MSK2 | TIP60 | |
| GCN5 | FPR4 | HOB1 | |

| | |
|---|---|
| Nuclear pore complex | |
| Nup153 | |
| Nup98 | |
| CRM1 | |
| other stable and dynamic pore components | |

| Ubiquitylation | IAP | Sumoylation |
|---|---|---|
| E1 | Cdc34 | Ubc9 |
| E2 | Rbx1 | SAE1/Aos1 |
| E3 | NEDD8/Rub1 | SAE2/Uba2 |
| 26S proteasome | SCF/Grr1 | SUMOE2 |
| E6 | SCF/Met30 | PIAS |
| VHL | SCF/Fbw7/hCdc4 | Ulp1 |
| MDM2 | Cue1p | Siz1 |
| BAP1 | Ubc7p | Siz2 |
| BARD1 | Ubc1p | SUMO E1 |
| CBL | CHIP | SUMO E3 |
| SCF/Skp2 | Hsp/c70/90 | Nse2 (Mms21) |
| Skp1 | Parkin | Ulp2 |
| Cul1/Cdc53 | NEDD4-2 | |
| DUB | Csn5 | |

Fusion Constructs

The tethering of a diversification factor to the cis-regulatory element is achieved via fusion of the diversification factor to a tethering factor. Fusion constructs encoding this combination of factors can be present in and expressed by the B cell of the invention, and can also be provided separately, to be added to the B cell at the desired time and upon selection of the desired factors for a particular objective.

Fusion constructs may generally be prepared using standard techniques. For example, DNA sequences encoding the peptide components may be assembled separately, and ligated into an appropriate expression vector. The ligated DNA sequences are operably linked to suitable transcriptional or translational regulatory elements. The 3' end of the DNA sequence encoding one peptide component is ligated, with or without a peptide linker, to the 5' end of a DNA sequence encoding the second peptide component so that the reading frames of the sequences are in phase. This permits translation into a single fusion protein that retains the biological activity of both component peptides.

A peptide linker sequence may be employed to separate the first and the second peptide components by a distance sufficient to ensure that each peptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional regions on the first and second peptides; and (3) the lack of hydrophobic or charged residues that might react with the peptide functional regions. Preferred peptide linker sequences contain Gly, Asn and Ser residues. Other near neutral amino acids, such as Thr and Ala may also be used in the linker sequence.

Methods and Uses of the Invention

The invention provides a method of producing a repertoire of polypeptides having variant sequences of a polypeptide of interest via diversification of polynucleotide sequences that encode the polypeptide. Typically, the method comprises culturing the B cell of the invention in conditions that allow expression of the diversification factor, wherein the target gene of the B cell contains the coding region of the polypeptide of interest, thereby permitting diversification of the coding region. The method can further comprise maintaining the culture under conditions that permit proliferation of the B cell until a plurality of variant polypeptides and the desired repertoire is obtained. Because the B cells express the polypeptides on the external surface, the nature and extent of the repertoire can be determined. The repertoire can then be used for selection of polypeptides having desired properties.

Figure 3:
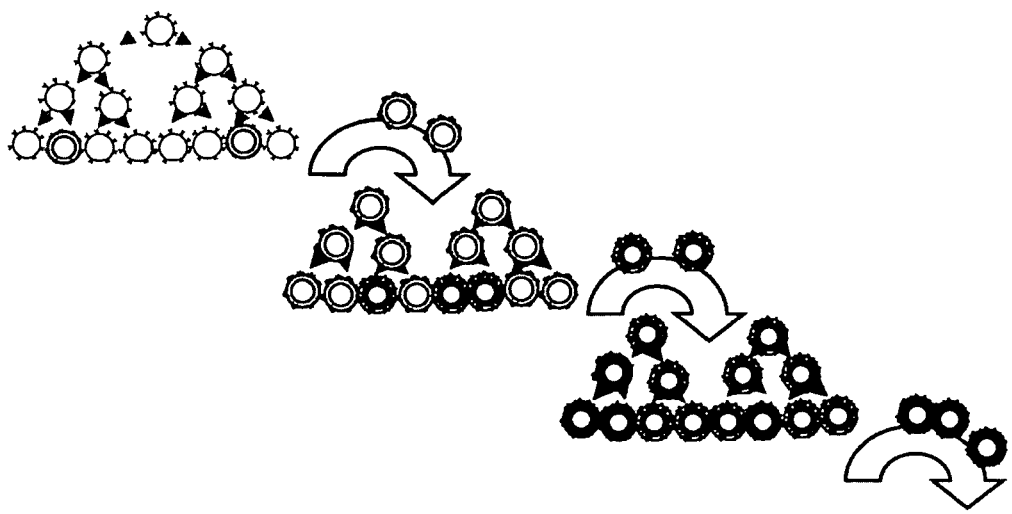
FIG. 3. Schematic illustration of how antibody specificities evolve during expansion of a B cell clone. Antibody is expressed on the cell surface. Selection of a population that initially expresses multiple specificities (top left) successively enriches for a desired specificity (thin double circles, center) and higher affinity (thick circles, bottom right).

In another embodiment, the invention provides a method of producing B cells that produce an optimized polypeptide of interest. The method comprises culturing a B cell of the invention in conditions that allow expression of the diversification factor, wherein the target gene of the B cell contains the coding region of the polypeptide of interest, and wherein the B cell expresses the polypeptide of interest on its surface. The method further comprises selecting cells from the culture that express the polypeptide of interest on the B cell surface by selecting cells that bind a ligand that specifically binds the polypeptide of interest. These steps of culturing and selecting can be repeated until cells are selected that have a desired affinity for the ligand that specifically binds the polypeptide of interest. The evolution of antibody specificities during expansion of a B cell clone is illustrated in FIG. 3. Selection of a population that initially expresses multiple specificities (top left) successively enriches for a desired specificity (center) and higher affinity (bottom right).

In embodiments in which the polypeptide of interest is an Ig, such as an IgL, IgH or both, the ligand may be a polypeptide, produced by recombinant or other means, that represents an antigen. The ligand can be bound to or linked to a solid support to facilitate selection, for example, by magnetic-activated cell selection (MACS). In another example, the ligand can be bound to or linked to a fluorescent tag, to allow for or fluorescence-activated cell sorting (FACS). Those skilled in the art appreciate that other methods of labeling and selecting cells are known and can be used in this method.

The methods of the invention can further comprise adding a regulatory molecule to the culture, wherein the regulatory molecule modulates binding of the tethering factor to the cis-regulatory element, thereby modulating diversification of the coding region. In the examples discussed above, IPTG, tetracycline and doxycycline serve as the regulatory molecules. Those skilled in the art are aware of other regulatory molecules that can be used with a particular tethering factor to regulate diversification activity.

The regulatory molecule can modulate the diversification of the coding region in a variety of ways. For example, in some embodiments, the regulatory molecule is added to the culture to effect modulation, and the modulation can result in reducing or halting diversification, or in enhancing or accelerating diversification, depending on whether the particular regulatory molecule is one that increases or decreases binding of the tethering factor to the cis-regulatory element, and on whether that particular change in binding has the effect of increasing or decreasing diversification activity. In other embodiments, the modulation, be it reduction, halt, enhancement or acceleration of the modulation, is effected by removing or eliminating the regulatory molecule from the culture. Likewise, modulation of diversification can be effected by adding a gene to or eliminating a gene from the B cell, or by increasing or diminishing the expression of a gene in the B cell. One skilled in the art can readily appreciate all of the available permutations set forth above, each of which has the effect of altering the level or presence of a regulatory molecule in the B cell, and in turn, altering the tethering of the diversification factor to the cis-regulatory element and thereby altering the diversification activity.

Additional uses of the methods of the invention include inducible hypermutation of Ig gene targets at Igλ. The DT40 PolyLacO-λ. LacI-HP1 cell line (see Example 4 below) can be used for altering the sequence of any Ig gene downstream of the Vλ pseudo-V array. The genomic structure at the Ig loci has evolved to promote mutagenesis of the V region but not the constant region of an Ig molecule. Altering Ig gene sequence in the context of an Ig locus takes advantage of that to ensure that the product of mutagenesis retains a functional constant region. The ease of gene replacement in DT40 permits useful changes in that gene. For example, the chicken gene (variable and constant region) could be replaced with a human antibody gene (either heavy or light chain), to generate antibodies with therapeutic application. This can also be used to generate therapeutic antibodies for other species. This will provide a rapid system for mutagenesis of either only one chain of a heterodimeric antibody; or for the single chain of single chain antibodies.

Uses of this approach include: hypermutation to generate B cell clones that produce high affinity Igs; hypermutation to alter cross-reactivity of antibodies, while retaining recognition of a specific epitope; hypermutation to identify V region sequences with high affinity for specific compounds. This can be done at only a single Ig locus, or both.

Inducible hypermutation can also be performed at IgH. The IgH locus in DT40 is an efficient site of mutagenesis, just like Igλ. Derivative cell lines, made by parallel techniques, permit mutagenesis at both IgH and Igλ, or at each allele separately. Insertion of PolyLacO at IgH, to create the DT40 PolyLacO-λ PolyLacO-H LacI-HP1 derivative, permits hypermutation at both H and L chain genes. Adding IPTG to the culture medium releases some of the inhibitory effects that diminish templated events and increase nontemplated hypermutation. Thus, by varying the presence and absence of IPTG, one can toggle back and forth between templated and nontemplated mutagenesis of the genes that encode both chains of an antibody.

A derivative can be made that combines regulation with IPTG of Lac Repressor (LacI) at one allele with tetracycline of Tet repressor (TetR) regulation at the other allele. This TetR derivative will permit independent regulation of diversification at the IgH and IgL alleles; and using different mechanisms simultaneously to regulate diversification at the IgL and IgH locus.

The invention also provides a vehicle for selection of T cell receptors. T cell-based immunotherapy has great potential (Blattman and Greenberg, 2004). T cell receptor specificity and affinity is governed by CDR contacts (Chlewicki et al., 2005). Accelerated inducible selection for specificity or high affinity T cell receptors can be carried out in a DT40 Poly-LacO vehicle, which has been modified by substitution of T cell receptors (V regions or entire genes) for the Ig loci.

Production of catalytic Igs is another aspect of the invention. The Ig-related methods of the invention are not simply limited to the production of Igs for binding and recognition, as the target Ig could also be used for catalysis. After development of a stable molecule that mimics the transition state of an enzymatic reaction, DT40 PolyLacO-λ LacI-HP1 cells can be used to evolve an antibody that binds and stabilizes the actual chemical transition state. After identifying clones that produce an Ig capable of binding the intermediate, the system can be used again to screen for catalytic activity of Igs on the real substrate in culture. Once some activity has been demonstrated in this system, optimization of activity can proceed by further evolution of the Ig loci through mutagenesis. Thus, invention does not require animal immunization (a slow step), immortalization by hybridoma technology, and the inefficiency of later having to screen hybridomas for antibodies that demonstrate catalytic activity.

Inducible hypermutation of non-Ig gene targets at Igλ or IgH is another aspect of the invention. The genomic structure at the Ig loci has evolved to promote mutagenesis of 1-1.5 kb downstream of the promoter. This system can be harnessed to mutate short regions of genes. Clonal selection based on surface protein expression can be incorporated by fusion of the region of interest to a portion of a gene expressing elements that mediate surface expression. Exemplary elements for surface expression include a signal peptide, transmembrane domain and cytoplasmic tail from a protein expressed on the B cell surface (Chou et al., 1999; Liao et al., 2001).

The invention can also be used for the production of recognition arrays. The ability to evolve cells harboring receptors with affinities for a large spectrum of antigens allows the development of recognition arrays. Combining this technology with intracellular responses/signaling from receptor stimulation in DT40 (such as measurement of Ca2+ by aequorin (Rider et al., 2003) or use of reporter gene transcription) would create a useful biosensor. Diversified clones would be spotted into arrays or 96 well plates, and exposed to samples. Each sample would yield a "fingerprint" of stimulation. The arrays would permit qualitative comparisons of biological/medical, environmental, and chemical samples. Analysis need not be limited to the analysis of proteins, as is the case for comparative techniques like 2D gels, since all forms of compounds could have antigenic properties. Furthermore, the arrays would lead to the identification of components without knowledge of their presence beforehand.

Kits

For use in the methods described herein, kits are also within the scope of the invention. Such kits can comprise a carrier, package or container that is compartmentalized to receive one or more containers such as vials, tubes, and the like, each of the container(s) comprising one of the separate elements (e.g., cells, constructs) to be used in the method.

Typically, the kit comprises a B cell of the invention and fusion constructs that express the corresponding tethering and diversification factors. For example, the B cell comprises a cis-regulatory element operably linked to a target gene, wherein the target gene comprises a promoter and a coding region. The kit further comprises one or more containers, with one or more fusion constructs stored in the containers. Each fusion construct comprises a polynucleotide that can be expressed in the B cell and that encodes a tethering factor fused to a diversification factor, wherein the tethering factor specifically binds to the cis-regulatory element of the B cell. The B cell can include a plurality of cis-regulatory elements for use with a plurality of fusion constructs.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for use. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1

Mutation and Targeting in the DT40 B Cell Line

This example illustrates an embodiment of the invention, prepared in two steps.

(1) DT40 PolyLacO-λ. We first constructed this derivative of the chicken B cell line DT40 containing a genetic element which allows regulation in cis at the Igλ locus. In DT40 PolyLacO-λ, a polymerized Lactose operator (LacO) is inserted just upstream of the pseudo-VX array at the Igλ light chain locus. This is an extension of a system developed by Straight and Belmont, in which PolyLacO consists of approximately 80 repeats of the 20 bp LacO binding site (Straight et al., 1996; Belmont, 2001). We have shown that this does not affect the normal process of templated mutagenesis. Construction of DT40PolyLacO-λ is described in detail in Example 2 below.

LacO is bound by Lactose repressor (LacI) with very high affinity: $<10^{-12}$ M. This mechanism regulates expression of the operon for metabolism of lactose in *E. coli*, and can also be used in a variety of cellular contexts. We have shown that LacI binds to PolyLacO in DT40 PolyLacO-λ, by generating stable transfectants that express LacI fused to fluorescent protein (GFP, RFP, YFP or CFP), and showing by immunofluorescence microscopy that bound protein can be imaged as a single spot in the nucleus of normally proliferating DT40 PolyLac stably expressing GFP-LacI, RFP-LacI, YFP-LacI or CFP-LacI.

IPTG is a small molecule which causes release of LacI from LacO, both in vitro and in cultured cells. Culture of DT40 PolyLacO-λ GFP-LacI with at little as 10 μM IPTG causes release of GFP-LacI from PolyLacO. Culture with IPTG does not affect cell proliferation.

(2) DT40 PolyLacO-λ LacI-HP1. We next constructed this derivative of DT40 PolyLacO-λ, in which a switch to somatic hypermutation occurs when *Drosophila melanogaster* HP1 (from L. Wallrath, University of Iowa), a modifier of chromatin structure, is tethered to PolyLacO. Tethering was achieved using the very well-characterized pair of cis- and trans-regulators, *E. coli* LacO/LacI. HP1 is a well-characterized non-histone heterochromatin protein that functions in heterochromatic gene silencing and the spreading of heterochromatin, and in *Drosophila* tethered LacI-HP1 has been shown to promote a closed chromatin structure and inactivation of reporter genes neighboring a lacO repeat (Li et al., 2003; Danzer and Wallrath, 2004). We demonstrated that tethering HP1 caused a transition of the donor sequences from an open to nonpermissive state, as measured by ChIP; and caused VX to undergo mutagenesis by somatic hypermutation rather than gene conversion. This is functionally equivalent to deletion of the pseudo-VX array, which has been shown to cause a switch from templated mutagenesis to somatic hypermutation (Arakawa et al., 2004). Further characterization of DT40 PolyLacO-λ. LacI-HP1 is documented in Example 4 below.

(3) DT40 PolyLacO-λ VP16-LacI. We next used the expression plasmid p3'ss-EGFP-VP16 (from A. Belmont; University of Illinois) to tether VP16-LacI to PolyLacO. VP16 is a strong activator of transcription, and it has been demonstrated to recruit histone acetyltransferase complexes (Tumbar et al., 1999). We demonstrated that tethering VP16 created a more permissive chromatin structure as measured by ChIP; and caused Vλ to undergo mutagenesis by a stimulation of gene conversion over wild-type levels.

Example 2

Acceleration of Mutagenesis by Tethering Genes to the Nuclear Pore

We discovered that diversifying immunoglobulin genes move within the nucleus in the course of the cell cycle, that this movement is correlated with the steps in the diversification pathway, and that diversification initiates at the nuclear periphery. Activation Induced Deaminase (AID), the enzyme that initiates diversification, carries a nuclear export signal and is constantly transported out of the nucleus via the nuclear pore, so its concentrations may be higher at the periphery of the nucleus. This suggested that it might be possible to accelerate diversification by increasing gene proximity to the nuclear pore. We showed that this is the case by using a fusion of the nuclear pore protein, Nup153, to Lac repressor (LacI) to tether the IgH locus in DT40PolyLacO to the nuclear pore. We found that this accelerated the clonal diversification rate 5.7-fold. Control experiments showed that tethering to Poly-Lac° was critical to acceleration of mutagenesis. This method is a general one that depends on the AID nuclear export signal and gene localization to promote mutagenesis of a target. Thus this method can be extended to promote mutagenesis of non-Ig genes in B cells, by tethering them to the pore; and further extended to promote mutagenesis of genes in non-B cells, by expressing AID in those cells.

Example 3

E2A Acts in cis in G1 Phase of Cell Cycle to Promote Ig Gene Diversification

This example describes cell cycle-dependent regulation of Ig gene diversification in the nucleus. Rearranged Ig genes undergo diversification in sequence and structure initiated by the DNA deaminase, AID. Ig genes must be transcribed for diversification to occur, but whether there are additional requirements for cis-activation has not been established. This example shows, by chromatin immunoprecipitation, that the regulatory factor E2A associates with the rearranged IgλR gene in the chicken DT40 B cell line, which carries out constitutive Ig gene diversification. By direct imaging of a DT40 derivative in which polymerized lactose operator tags the rearranged λR gene, we show that λR/E2A colocalizations are most prominent in G1 phase of cell cycle. We further show that expression of the E2A antagonist Id1 prevents λR/E2A colocalizations in G1 phase, and impairs diversification but not transcription of λR (hereinbelow, the IgλR gene is sometimes referred to as Igλ or λ). Thus, E2A acts in cis to promote Ig gene diversification, and G1 phase is the critical window for E2A action.

The regulated changes in genomic sequence and structure that take place at the Ig loci reflect both targeting of DNA damage to these genes, and escape from faithful repair. Somatic hypermutation, class switch recombination and gene conversion are all initiated by the B cell-specific enzyme, activation-induced deaminase (AID) (5-8). AID deaminates cytosine to uracil, with clear preference for single-stranded DNA (9-11). Transcription is prerequisite for diversification, which may reflect preference of AID for single-stranded substrates. Uracil in DNA is a common lesion, which can be repaired faithfully by highly conserved and efficient pathways (12). However, the Ig loci can escape from faithful repair and undergo repair by error-prone pathways (13).

E2A, a member of the E family of bHLH proteins, is a critical regulator of many aspects of lymphocyte development (14-17). E proteins dimerize to bind to the E box motif, CANNTG, and their function is antagonized by Id proteins, which heterodimerize with E proteins to prevent DNA binding. E2A is induced in activated murine B cells, where it regulates class switch recombination (18) as well as expression of the gene that encodes AID (19). In chicken B cells, inactivation of the E2A gene impairs IgA gene diversification but not transcription (20, 21); while, conversely, ectopic expression of E47 (one of two functionally equivalent isoforms encoded by E2A) promotes Igλ gene diversification, but does not affect IgA transcript levels (22).

The possibility that E2A might regulate Ig gene diversification by binding to sites in cis was first suggested by evidence that multimerized E-boxes stimulate hypermutation but not transcription of an Ig transgene in mice (23). This possibility has been further supported by the demonstration that multimerized E-boxes can promote Ig gene diversification but not transcription in chicken B cells (24). However, clear resolution of the question of whether E2A acts directly at the Ig genes to promote diversification has been difficult, for several reasons. E-boxes function as sites for E2A-dependent regulation only in specific contexts, so the presence of an E-box does not guarantee E2A function at a site; the loose consensus and frequent occurrence of E-box motifs precludes mutational analysis of each individual site; and at some loci E2A is recruited by protein-protein rather than protein-DNA interaction, so an E-box is not always prerequisite for E2A-dependent regulation (25).

We have now established that E2A acts in cis at the Ig genes to promote diversification, in experiments which take advantage of derivatives of the constitutively diversifying chicken B cell line, DT40, in which the rearranged Igλ allele is tagged with polymerized lactose operator (DT40 PolyLacO-λR). By chromatin immunoprecipitation (ChIP), we show that E2A associates with the rearranged but not unrearranged IgA allele in the parental line, DT40. This example demonstrates that, in DT40 PolyLacO-λR cells, diversification is accelerated upon expression of an E47-LacI fusion protein, which effectively tethers E47 to λR; and that the stimulatory effect of E47-LacI expression is not evident in cells cultured with IPTG, so binding in cis is necessary to promote diversification. By direct imaging of the rearranged λR gene in DT40 PolyLacO-λR GFP-LacI cells, we show that λR/E2A colocalizations predominate in G1 phase; and that expression of the E2A antagonist, Id1, impairs diversification and diminishes λR/E2A colocalizations specifically in G1 phase, but does not affect A transcript levels or localization of λR to active transcription factories. These results show that E2A acts in cis in G1 phase to promote Ig gene diversification.

Materials and Methods

Cell Culture, Transfection, sIgM Loss Assay and Cell Cycle Analysis

The chicken bursal lymphoma line DT40 and its derivative DT40 PolyLacO-$\lambda_R$ were maintained and transfected as described (26, 27). The E47-LacI expression construct was generated by subcloning of E47 cDNA from the S003 E47 plasmid (28) (provided by Cornelis Murre, University of California, San Diego, Calif.) into the p3'SS-GFP-LacI plasmid (provided by Andrew Belmont, University of Illinois, Urbana, Ill.). The Id1 expression construct (29) was provided by Barbara Christy (University of Texas, San Antonio, Tex.). The sIgM-loss assay was carried out as described (26, 30), and results compared using the Mann-Whitney U test with the R software package (http://www.r-project.org). For cell-cycle profiles based on DNA content, $1\times10^6$ exponentially growing cells were suspended in 0.1% Triton X-100, treated with 200 μg/ml RNase A and 50 μg/ml propidium iodide, and analyzed as described (26).

ChIP Analysis

Chromatin was prepared and immunoprecipitated as described (27, 31, 32); using anti-E2A antibody (ab11176; Abcam) or control IgG. Semiquantitative PCR was performed with FastStart Taq DNA polymerase (Roche), using previously described primers for V$\lambda_R$ and V$\lambda_U$ (27); and primers 5'-ATTGCGCATTGTTATCCACA-3' (SEQ ID NO: 1) and 5'-TAAGCCCTGCCAGTTCTCAT-3' (SEQ ID NO: 2) for ovalbumin (Ova). PCR products were quantitated with ImageQuant software (Amersham). Enrichment was calculated as the ratio of the amplicon of interest to the Ova amplicon, normalized to the ratio from control IgG, e.g.: Enrichment V$\lambda_R$=(anti-E2A [V$\lambda_R$/Ova])/(IgG [V$\lambda_R$/Ova]).

RT-PCR and Western Blotting

For RT-PCR assays, AID and b-actin were amplified with primers as described (7); and Igλ transcripts with primers 5'-GTCAGCAAACCCAGGAGAAAC-3' (SEQ ID NO: 3) and 5'-AATCCACAGTCACTGGGCTG-3' (SEQ ID NO: 4). For Western blotting, whole cell lysates (50 μg) from DT40 PolyLacO-$\lambda_R$ RFP-LacI and DT40 PolyLacO-$\lambda_R$ RFP-LacI Id1 were resolved, and Id1 protein was detected with anti-Id1 antibody (JC-FL; Santa Cruz) using FluorChem HD2 (Alpha Innotech).

Fluorescence Microscopy and Image Analysis

To image PolyLacO, DT40 PolyLacO-$I_R$ cells were transfected with the GFP-LacI expression construct, p3'SS-GFP-LacI (from Andrew Belmont, University of Illinois, Urbana, Ill.), which encodes LacI engineered to contain SV40 nuclear localization signals and lacking a sequence necessary for tetramer formation (33); or its derivative, RFP-LacI, in which GFP was replaced with RFP (DsRed-monomer; Clontech). For immunostaining, cells (~$3\times10^5$) were deposited onto glass slides using Cytospin3 (800 rpm, 4 min; Shandon), fixed with 2% paraformaldehyde for 20 min, and stained as described previously (26). Primary antibodies used were: anti-E2A (ab11176, 1:200; Abcam); anti-Pol II C-terminal domain phosphorylated at Ser5 (ab5131, 1:500; Abcam). Alexa Fluor 488- or 594-conjugated anti-IgG (Molecular Probes) was used as secondary antibodies. Fluorescent images were acquired using the DeltaVision microscopy system (Applied Precision) and processed and analyzed with softWoRx (Applied Precision) and Imaris softwares (Bitplane). Fluorescent signals were sometimes partially rather than completely overlapping, which may reflect the considerable distance (~17 kb) between the PolyLacO-tag and the VX region; both configurations were scored as colocalization. Fraction of colocalization was analyzed with Pearson's $\chi^2$ test. Nuclear radii were calculated as the average of at least two independent measurements of diameter, divided by two.

Figure 4A:
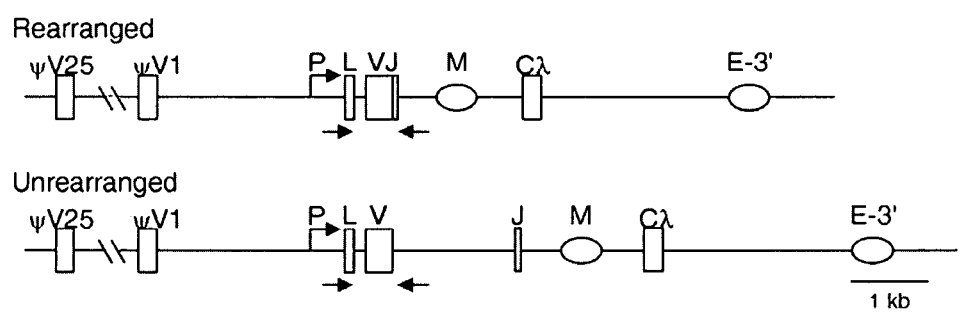
FIG. 4A-B. Demonstration that E2A associates with the rearranged Igλ locus.
Figure 4B:
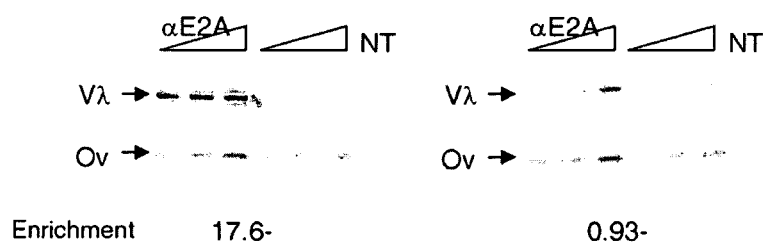

Cell cycle dependence of mean nuclear radius was determined independently for each cell line, and proved to be relatively invariable. Standard values used to correlate nuclear radius to cell cycle were: G1, r<4 µm; G2, r≥5.2 µm.
Results E2A Associates With the Rearranged But Not Unrearranged Igλ Gene Despite the considerable evidence for the importance of E2A in Ig gene diversification, this factor had not been shown to associate directly with the Ig genes. To test association of E2A with Igλ, we used anti-E2A antibodies to immunoprecipitate chromatin from the chicken DT40 B cell line. This line was derived from a bursal lymphoma and carries out constitutive diversification of both Ig heavy and light chain genes by gene conversion. A search of the 11 kb chicken λ light chain locus identified more than 50 matches to the E2A consensus, CANNTG: 17 in the region between Vλ and ΨVλ1, the most proximal of the upstream pseudogenes; 2 in the matrix attachment region (MAR) in the J-C intron; and 6 in the 3' enhancer. In DT40 B cells, the functional allele has undergone VJ recombination early in B cell development, which deletes a 1.8-kb region to join the V and J segments, while the inactive A allele is unrearranged (FIG. 4A), allowing the two alleles to be readily distinguished by PCR. Following chromatin immunoprecipitation (ChIP), recovery of the rearranged and unrearranged λ alleles was assayed relative to a control gene, ovalbumin. This showed that E2A was 17.6-fold enriched at the rearranged VλR allele, but not enriched at the unrearranged VλU allele (FIG. 4B). Thus E2A associates directly with the rearranged VλR allele.

E2A Acts in cis to Regulate Igλ Diversification

To ask if E2A must bind in cis to promote diversification, we took advantage of a derivative of DT40, DT40 PolyLacO-λR, in which polymerized lactose operator has been inserted in the ΨVλ array by homologous gene targeting (FIG. 5A), allowing factors expressed as fusions with lactose repressor (LacI) to be tethered to the rearranged λR allele and released by culture with IPTG (27). Cell cycle distribution and clonal rates of Ig gene conversion were comparable in DT40 PolyLacO-λR and wild-type DT40 (FIG. 5B, C). DT40 PolyLacO-λR cells were stably transfected with a plasmid expressing the E47 isoform of E2A fused to LacI (E47-LacI), or a control plasmid expressing green fluorescent protein fused to LacI (GFP-LacI). Cell cycle distribution was comparable in GFP-LacI and E47-LacI transfectants, although cultures of the latter line contained some sub-G1 (apoptotic) cells (FIG. 5D). Levels of Igλ transcripts were unaltered in the E47-LacI transfectants (FIG. 5E), confirming published results showing that E2A does not regulate Ig gene expression in chicken B cells (21, 22). Levels of AID transcripts were approximately 3-fold higher in the E47-LacI transfectants (FIG. 5E). A similar increase in AID expression in response to ectopic expression of E47 has been observed by others (22).

To ask if E2A regulates diversification directly, via binding to IgA, we cultured independent E47-LacI (n=19) or GFP-LacI (n=13) transfectants in the presence and absence of IPTG, and determined clonal diversification rates using the sIgM loss fluctuation assay (26, 27, 30). This assay scores inactivating mutations regardless of whether they occur by gene conversion, point mutation, deletion or insertion, and thus quantitates initiating events independent of the outcome of mutagenesis. This analysis showed that the clonal rate of diversification was 4.5-fold higher in E47-LacI transfectants relative to GFP-LacI controls (P=0.019, Mann-Whitney U test; FIG. 5F). Moreover, culture with IPTG, which releases E47-LacI from PolyLacO, caused diversification rates to return almost to background levels in DT40 PolyLacO-λR E47-LacI cells, but had no effect on GFP-LacI controls (FIG. 5F). Thus E47-LacI promotes diversification by acting in cis.

E2A Localizes to IgλR in G1 Phase of Cell Cycle

In human B cells, receptor crosslinking in G1 phase of cell cycle can initiate somatic hypermutation, producing identifiable mutations within 90 minutes (34). Thus it was of interest to determine the stage of cell cycle in which E2A acts at Igλ. The rearranged and diversifying λR gene can readily be imaged as a bright dot in DT40 PolyLacO-λR cells expressing GFP-LacI (27). However, when cells were stained with Hoechst 33342 and sorted by DNA content to enrich for cells in G1, S, or G2/M stage, the fraction of cells exhibiting a clear fluorescent signal from the tagged gene diminished from the 90-95% routinely observed in unsorted cells to approximately 45%. As such a loss in signal could bias results, we therefore determined cell cycle stage by a different approach. Analysis of Hoechst 33342-stained and sorted cells showed that nuclear size was significantly smaller in G1 phase than in G2/M phase cells (e.g. FIG. 6A). We therefore asked if nuclear radius (r) could be used to establish the stage of cell cycle, by measuring nuclear radii of G1 cells (n=55) and G2 cells (n=55) from an exponentially growing DT40 PolyLacO-λR population which had been stained with Hoechst 33342 and sorted based on DNA content. Mean nuclear radii of G1 cells was 3.8±0.3 µm; and of G2 cells, 5.4±0.5 µm (FIG. 6B). Comparison of the ratios of G1:S:G2 cells as determined by nuclear radius (3:6:1) and staining (2.7:5.5:1.7) further validated this approach. Thus, G1 cells were identified experimentally as r<4 µm; and G2 cells, r>5.2 µm.

Colocalizations of λR/E2A were readily identified by deconvolution microscopic analysis of DT40 PolyLacO-λR GFP-LacI cells stained with anti-E2A antibodies (e.g. FIG. 7A). λR/E2A colocalizations were evident in 26% of asynchronous cells (n=227). Analysis of the cell cycle distribution of colocalizations showed that 45% of λR/E2A colocalizations occurred in G1 phase, 38% in S phase, and 17% in G2 phase cells (FIG. 7B). Thus, there was an apparent excess of λR/E2A colocalizations in G1 phase (45%) relative to the fraction (25%) of G1 phase cells (P<0.0001, χ2 test).

We also determined the cell cycle-dependence of λR transcription, identifying active transcription factories by staining with antibody to phosphorylated Ser5 in the C-terminal domain of RNA polymerase II (P*-Pol II), a modification characteristic of elongating Pol II molecules (35). In asynchronous cell populations of DT40 PolyLacO-λR RFP-LacI cells, numerous active transcription factories could be identified throughout the nucleus, and λR/P*-Pol II colocalizations were readily observed in 19% of cells (n=392; e.g. FIG. 7C). Analysis of the cell cycle distribution of λR/P*-Pol II colocalizations showed that 21% of colocalizations occurred in G1 phase; 58% in S phase; and 21% in G2 phase cells (FIG. 7D). This is comparable to the cell cycle distribution. Thus, λR is transcribed throughout the cell cycle, but λR/E2A colocalizations predominate in G1 phase.

Figure 8A:
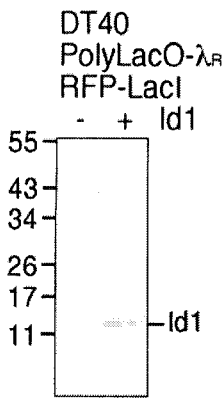
FIG. 8A-F. Id1 expression inhibits λR/E2A colocalizations in G1 phase.
Figure 8B:
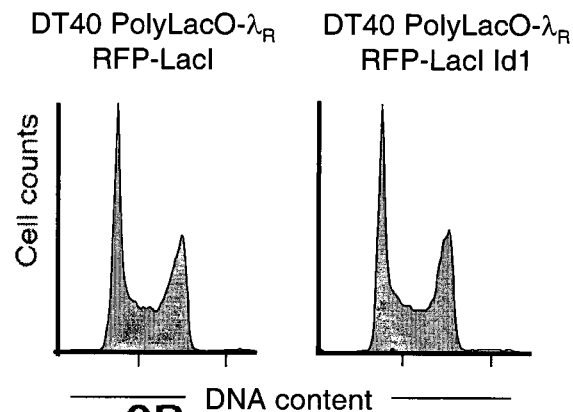
Figure 8C:
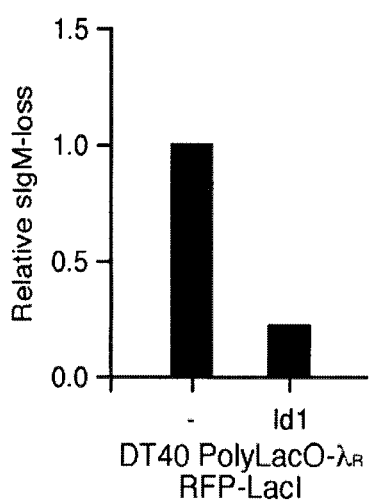
Figure 8D:
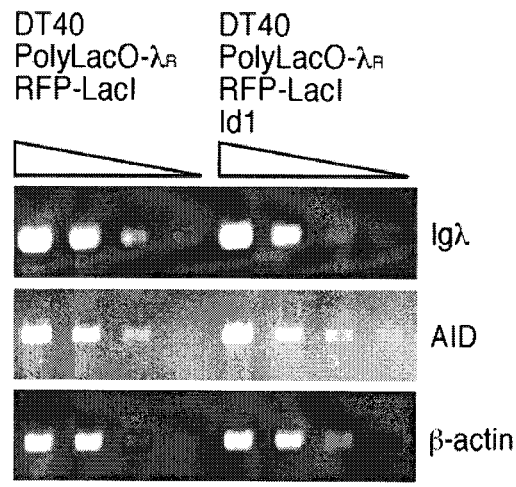

Id1 Expression Inhibits Ig Gene Diversification and λR/E2A Colocalizations in G1 Phase To ask if λR/E2A colocalizations in G1 phase are critical to diversification, we determined the effect of Id expression on these colocalizations. Id antagonizes E2A, and expression in DT40 B cells of Id1 or Id3 has previously been shown to diminish Ig gene diversification (22). We generated stable DT40 PolyLacO-λR RFP-LacI Id1 transfectants, confirmed Id1 expression by Western blotting (FIG. 8A), and showed that Id1 expression did not alter the cell cycle profile (FIG. 8B). We verified that Id1 expression diminished the clonal rate of Ig gene diversification (P<0.001, Mann-Whitney U test; FIG. 8C); but did not affect levels of Igλ or AID transcripts (FIG. 8D). We then compared λR/E2A colocalizations in the Id1-expressing derivative and parental line, by staining with anti-E2A antibodies. λR/E2A colocalizations were evident in 13% of asynchronous DT40 PolyLacO-λR RFP-LacI Id1 cells (n=90), compared to 26% of DT40 PolyLacO-λR RFP-LacI cells (P=0.0030, $\chi^2$ test).

Figure 8E:
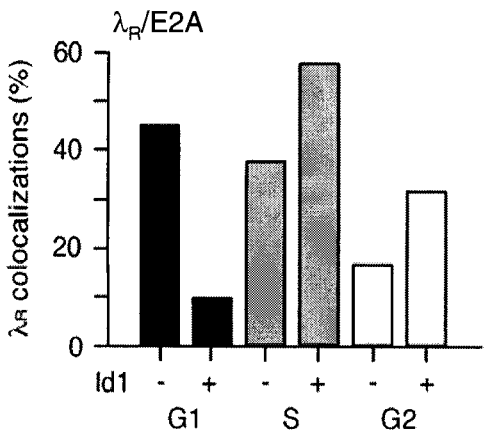
Figure 8F:
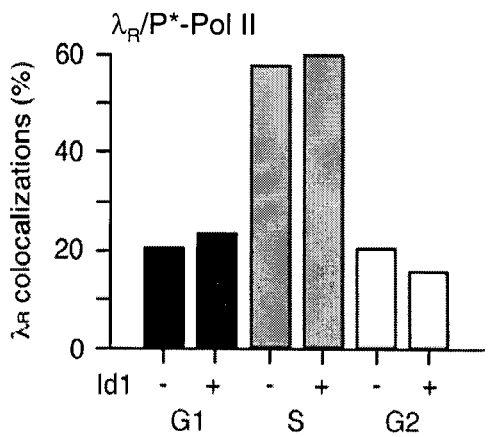

To determine whether Id1 expression affected colocalizations in a specific stage of cell cycle, λR/E2A colocalizations in the Id1 transfectants were quantified with respect to nuclear radius and cell cycle. This showed that, in DT40 PolyLacO-λR RFP-LacI Id1 cells, 10% of colocalizations occurred in G1 phase; 58% in S phase; and 32% in G2 phase cells (FIG. 8E). Thus, Id1 expression caused a significant decrease in the fraction of λR/E2A colocalizations in G1 phase, from 45% in the parental line to 10% in Id1 transfectants (P<0.0001, $\chi^2$ test; FIG. 8E); and 90% of λR/E2A colocalizations in Id1 transfectants occurred after G1 phase of cell cycle. Taken together with diminished diversification evident in Id1 transfectants, this shows that G1 phase is the critical window in which E2A promotes diversification.

λR/P*-Pol II colocalizations were identified in 18% of DT40 PolyLacO-λR RFP-LacI Id1 cells stained with antibodies to active transcription factories (n=290), comparable to the parental line (19%, P=0.80, $\chi^2$ test; FIG. 7D). The cell cycle profile of λR/P*-Pol II colocalizations was also comparable in Id1 transfectants and the parental line (FIG. 8F). The absence of effect of Id1 expression on λR/P*-Pol II colocalizations is consistent with undiminished Igλ transcript levels in DT40 PolyLacO-λR RFP-LacI Id1 transfectants (FIG. 8D). Thus, Id1 expression affects the cell cycle distribution of colocalizations of λR with E2A, but not with P*-Pol II.

Discussion

These results show that E2A must act in cis to promote Ig gene diversification, and that G1 phase is the critical window in which E2A functions in this process. The experiments have examined λ genes tagged with PolyLacO and imaged by binding to GFP-LacI or RFP-LacI. This provides a powerful approach for studying gene diversification. The tagged locus is visible in >90% of fixed cells, enabling analysis of colocalizations with factors involved in diversification.

The ability to tether potential regulators and release by culture with IPTG makes it possible to study the effects of a factor at the Igλ locus independent of its other targets. This is especially useful for a factor like E2A, which functions at the top of a large and complex regulatory hierarchy (36).

The results establish that E2A directly regulates Ig gene diversification by physical association with the Ig loci. ChIP provided clear evidence for association of E2A with the rearranged λR allele in DT40 B cells. That E2A must function in cis was established by showing that the acceleration in diversification resulting from tethering E2A (E47-LacI fusion) to the Igλ allele in DT40 PolyLacO-λR cells was not evident in cells cultured with IPTG, which releases LacI from LacO.

E2A is best-known as a transcriptional regulator, but E2A function in diversification does not reflect transcriptional activation at Igλ, as levels of Igλ transcripts were not altered by ectopic expression of E47. This confirms results of others who have examined the effects of E2A on diversification in chicken and murine B cells (20, 22, 23). In addition, colocalizations of λR with E2A, which are most prominent in G1 phase, distinct from the cell cycle distribution of λR to active transcription factories, which is comparable to cell cycle distribution, suggesting that λR is transcribed throughout the cell cycle. The independence of E2A function in diversification and transcription is further supported by the contrasting effects of Id1 expression on colocalizations of the rearranged λR with E2A and active transcription factories. Id1 expression diminished diversification, and also diminished colocalizations of λR with E2A. In contrast, Id1 expression did not affect the number or cell cycle distribution of localization of λR to active transcription factories. That E2A is not required to recruit λR to transcription factories is consistent with the absence of effect of Id1 expression on Igλ transcription.

E2A does regulate AID expression, and this indirectly stimulates Ig gene diversification. The AID gene was shown to be a target of transcriptional regulation by E2A in murine B cells (19); and we and others (22) have shown that ectopic expression of E2A increases AID transcript levels in DT40 chicken B cells. This may contribute to or account for the modest acceleration in diversification evident in IPTG-cultured DT40 PolyLacO-λR E47-LacI cells. While E2A ablation has been reported not to diminish AID transcript levels in chicken B cells (21), factors redundant with E2A might ensure a minimum level of AID expression in the absence of E2A.

The results identify G1 phase as the critical window in which E2A functions at Igλ. We observed an excess of λR/E2A colocalizations in G1 phase, relative to other stages of cell cycle; and showed that Id1 expression specifically diminishes colocalizations in G1 phase, and decreases the diversification rate. Id proteins heterodimerize with E proteins to inhibit DNA binding (14). That colocalizations during G1 were specifically affected by Id1 expression may be indicative of distinct modes of E2A association with Igλ during cell cycle. In S and G2 phases, E2A may be recruited via interactions with other proteins, rather than by direct binding to DNA.

Additional lines of evidence support the view that diversification is initiated in G1 phase. Somatic hypermutation in the human BL2 cell line can be induced by in vitro stimulation that takes place only during G1 phase, and point mutations first become evident within 90 minutes of stimulation, when cells are still in G1 (34). In murine B cells activated for class switch recombination, IgH colocalizations with NBS1 or γ-H2AX, participants in the switch recombination pathway, are prominent in G1 phase (37); and DNA breaks at the S regions can be detected in G1 phase (38). DNA breaks have also been identified in later stages of cell cycle in hypermutating human B cell lines (39), but these proved to be AID-independent (40).

E2A may function in G1 phase to prepare a locus for events that occur later in cell cycle, or even during a subsequent cell cycle. E2A has been recently implicated in maintenance of histone H4 acetylation (21), and it is possible that E2A functions to establish a local chromatin environment favorable to AID attack or effective diversification in daughter cells.

References

1. Maizels, N. 2005. *Annu Rev Genet* 39: 23-46.
2. Martomo, S. A., and P. J. Gearhart. 2006. *Curr Opin Immunol* 18: 243-248.
3. Di Noia, J. M., and M. S. Neuberger. 2007. *Annu Rev Biochem* 76: 1-22.
4. Teng, G., and F. N. Papavasiliou. 2007. *Annu Rev Genet* 41: 107-120.
5. Muramatsu, M., et al. 2000. *Cell* 102: 553-563.
6. Revy, P., et al. 2000. *Cell* 102: 565-575.
7. Arakawa, H., et al. 2002. *Science* 295: 1301-1306.
8. Harris, R. S., et al 2002. *Curr Biol* 12: 435-438.
9. Bransteitter, R., et al. 2003. *Proc Natl Acad Sci U S A* 100: 4102-4107.
10. Chaudhuri, J., et al. 2003. *Nature* 422: 726-730.

11. Ramiro, A. R., et al. 2003. *Nat Immunol* 4: 452-456.
12. Barnes, D. E., and T. Lindahl. 2004. *Annu Rev Genet* 38: 445-476.
13. Liu, M., et al. 2008. *Nature* 451: 841-845.
14. Murre, C. 2005. *Nat Immunol* 6: 1079-1086.
15. Hagman, J., and K. Lukin. 2006. *Curr Opin Immunol* 18: 127-134.
16. Murre, C. 2007. *Adv Exp Med Biol* 596: 1-7.
17. Nutt, S. L., and B. L. Kee. 2007. *Immunity* 26: 715-725.
18. Quong, M. W., et al. 1999. *Embo J* 18: 6307-6318.
19. Sayegh, C. E., et al. 2003. *Nat Immunol* 4: 586-593.
20. Schoetz, U., et al. 2006. *J Immunol* 177: 395-400.
21. Kitao, H., et al. 2008. *Int Immunol* 20: 277-284.
22. Conlon, T. M., and K. B. Meyer. 2006. *Eur J Immunol* 36: 139-148.
23. Michael, N., et al. 2003. *Immunity* 19: 235-242.
24. Kothapalli, N., et al. 2008. *J Immunol* 180: 2019-2023.
25. Lazorchak, A. S., et al. 2006. *Mol Cell Biol* 26: 810-821.
26. Yabuki, M., et al. 2005. *Nat Immunol* 16: 730-736.
27. Cummings, W. J., et al. 2007. *PLoS Biol* 5: e246.
28. Engel, I., and C. Murre. 1999. *Proc Natl Acad Sci U S A* 96: 996-1001.
29. Bounpheng, M. A., et al. 1999. *Faseb J* 13: 2257-2264.
30. Sale, J. E., et al. 2001. *Nature* 412: 921-926.
31. Larson, E. D., et al. 2005. *Curr Biol* 15: 470-474.
32. Larson, E. D., et al. 2005. *Mol Cell* 20: 367-375.
33. Belmont, A. S., and A. F. Straight. 1998. *Trends Cell Biol* 8: 121-124.
34. Faili, A., et al. 2002. *Nat Immunol* 3: 815-821.
35. Palancade, B., and O. Bensaude. 2003. *Eur J Biochem* 270: 3859-3870.
36. Schwartz, R., et al. 2006. *Proc Natl Acad Sci U S A* 103: 9976-9981.
37. Petersen, S., et al. 2001. *Nature* 414: 660-665.
38. Schrader, C. E., et al. 2007. *J Immunol* 179: 6064-6071.
39. Papavasiliou, F. N., and D. G. Schatz. 2000. *Nature* 408: 216-221.
40. Papavasiliou, F. N., and D. G. Schatz. 2002. *J Exp Med* 195: 1193-1198.

Example 4

Chromatin Structure Regulates Gene Conversion

This example illustrates how chromatin structure contributes to the use of homologous sequences as donors for repair using the chicken B cell line DT40 as a model. In DT40, immunoglobulin genes undergo regulated sequence diversification by gene conversion templated by pseudogene donors. We have found that the VX pseudogene array is characterized by histone modifications associated with active chromatin. We have directly demonstrated the importance of chromatin structure for gene conversion, using a regulatable experimental system in which the heterochromatin protein, HP1, expressed as a fusion to Lac repressor, is tethered to polymerized lactose operators integrated within the pseudo-Vλ donor array. Tethered HP1 diminished histone acetylation within the pseudo-Vλ array, and altered the outcome of Vλ diversification, so that nontemplated mutations rather than templated mutations predominated. Thus, chromatin structure regulates homology-directed repair. These results suggest that histone modifications may contribute to maintaining genomic stability by preventing recombination between repetitive sequences.

This example uses the following abbreviations: AcH3, acetylated histone H3; AcH4, acetylated histone H4; AID, activation-induced deaminase; DSB, double-strand break; GFP, green fluorescent protein; Ig, immunoglobulin; MRN, MRE11/RAD50/NBS1; NHEJ, nonhomologous end-joining; V, variable; UNG, Uracil DNA glycosylase; AP, abasic; PolyLacO, polymerized lactose operator; ChIP, chromatin immunoprecipitation; Ova, ovalbumin; LOH, Loss of heterozygosity.

Materials and Methods

Chromatin immunoprecipitation (ChIP). ChIP was carried out as previously described [48,89]. For all experiments at least two chromatin preparations from at least two independent stably-transfected lines were analyzed. Figures present one representative experiment in which results from analysis of four separate amplifications were used to calculate a standard deviation. Four separate amplifications of serial dilutions of template DNA were carried out, to establish that the measured product intensities were within the linear range. Enrichment of the experimental amplicon was normalized to enrichment of an internal control amplicon from the ovalbumin (Ova) gene, amplified in the same tube by duplex PCR; and enrichment upon ChIP with specific antibodies was normalized to parallel experiments in which ChIP was carried out with total input DNA controls. Inclusion of the Ova internal control amplicon enabled us to normalize for IP efficiency, background carryover, and differences in gel loading. Enrichment=[(ΨVλ/Ova)Ab]/[(ΨVλ/Ova)Input]. As an additional control, the ratio of the experimental and control amplicons in the total input control was compared to a control ChIP with polyspecific IgG; in all cases, enrichment in input and IgG controls were essentially equal. Data are presented for representative experiments; standard deviations were calculated from four separate amplifications of serial dilutions of template DNA.

Antibodies used were: anti-AcH3 (06-599), anti-AcH4 (06-866), and dimethylated H3(K4) (07-030) from Upstate (Lake Placid, N.Y.). PCR primers for ChIP were:

```
Vλ_R:
            (SEQ ID NOS: 5-28, respectively)
5'-GCCGTCACTGATTGCCGTTTTCTCCCCTC-3'
and

5'-CGAGACGAGGTCAGCGACTCACCTAGGAC-3';

region between ψVλ1 and Vλ:
5'-CTGTGGCCTGTCAGTGCTTA-3'
and

5'-GCAGGGAACCACAAGAACAT-3';

ψVλ1:
5'-GGGACTTGTGTCACCAGGAT-3'
and

5'-CGCAGTCACATGTGGAATATC-3';

ψVλ5:
5'-GAGCCCCATTTTCTCTCCTC-3'
and

5'-GAGATGTGCAGCAACAAGGA-3';

ψVλ13:
5'-CCCTCTCCCTATGCAGGTTC-3'
and

5'-CCCCTATCACCATACCAGGA-3';

ψVλ18:
5'-CCATTTTCTCCCCTCTCTCC-3'
and

5'-TCACCCTACAGCTTCAGTGC-3';
```

-continued

ψVλ24:
5'-CCATTTTCTCCCCTCTCTCC-3'
and

5'-CAGCCCATCACTCCCTCTTA-3';

ψVλ25:
5'-TCTGTTGGTTTCAGCACAGC-3'
and

5'-GCAGTTCTGTGGGATGAGGT-3';

ψVλ upstream flank:
5'-GGCTCCTGTAGCTGATCCTG-3'
and

5'-GTTCTTTGCTCTTCGGTTGC-3';

ψVλ17 at the PolyLacO-targeted allele:
5'-TAGATAGGGATAACAGGGTAATAGC-3'
and

5'-AGGGCTGTACCTCAGTTTCAC-3';

OVA:
5'-ATTGCGCATTGTTATCCACA-3'
and

5'-TAAGCCCTGCCAGTTCTCAT-3';

polε:
5'-GGGCTGGCTCATCAACAT-3'
and

5'-CTGGGTGGCCACATAGAAGT-3'.

Constructs, Transfection and Cell Culture.

The LacI-HP1 expression plasmid was created by substituting LacI-HP1a from a construct provided by L. Walirath (University of Iowa, Iowa City) for AID in pAIDPuro (from H. Arakawa; Munich, Germany), to position LacI-HP1 downstream of the chicken β-actin promoter. The GFP-LacI expression plasmid (p3'ss-EGFP-LacI) was provided by A. Belmont (University of Illinois, Urbana). Cell culture and transfection were carried out as previously described [47]. DT40 PolyLacO-$λ_R$ was generated by homologous gene targeting, using a construct carrying approximately 3.8 kb of polymerized lactose operator (PolyLacO) flanked by arms designed for targeting the region between ΨVλ17-ΨVλ20, 17 kb upstream of the transcribed V$λ_R$. In brief, homologous integrants were identified by PCR, and the selectable marker deleted by Cre expression. The DT40 bursal lymphoma derives from B cell in which only one Igλ allele is rearranged, and in which the two parental chromomes are distinguished by a polymorphism near ΨVλ17. This enabled us to determine whether the rearranged or unrearranged allele had been targeted by PCR. Control experiments established that cell cycle distribution was comparable in DT40 PolyLacO-$λ_R$, DT40 PolyLacO-$λ_R$ GFP-LacI and DT40 PolyLacO-$λ_R$ LacI-HP1 cells; and that culture of cells with up to 500 μM IPTG for 7 days did not affect proliferation rate or chromatin modifications at ΨVλ17$_R$ in DT40 PolyLacO-$λ_R$ GFP-LacI control cells. Oligonucleotides for Vλ sequence analysis have been described [47].

Fluorescence Imaging.

For fluorescence imaging, cells (2×10$^5$) were cytospun onto glass slides and fixed with 2% paraformaldehyde for 20 min, permeabilized with 0.1% NP-40 for 15 min, and stained as previously described [90]. Primary staining was with an anti-LacI monoclonal antibody (1:500 dilution; Upstate); and the secondary antibody was donkey anti-mouse IgG Alexa Fluor 594 (1:2000; Molecular Probes, Eugene, Oreg.). To visualize the nucleus, cells were stained with DAPI (Sigma, Saint Louis, Mo.). Fluorescent images were acquired using the DeltaVision microscopy system (Applied Precision) and processed with softWoRx software (Applied Precision).

RT-PCR.

RNA was harvested from cells using TRIzol Reagent (Invitrogen) and purified with a PreAnalytiX column (Qiagen). VA transcripts were amplified following dilution of the template (1:1300); and β-actin was amplified from an undiluted sample. The primers for amplification of Vλ were 5'-GTCAGCAAACCCAGGAGAAAC-3' (SEQ ID NO: 29) and 5'-AATCCACAGTCACTGGGCTG-3' (SEQ ID NO: 30). The primers for amplification of β-actin have been described [36].

Quantitation of sIgM Loss Variants and Sequence Analysis.

The sIgM loss variant assay, which measures the accumulated sIgM-loss variants resulting from frameshift or nonsense mutations in mutated V regions, was used to quantitate Ig V region diversification [47,50]. In brief, sIgM$^+$ cells were isolated by flow cytometry followed by limiting dilution cloning, and expanded for 4 weeks. To quantitate the fraction of sIgM$^-$ cells, approximately 1×10$^6$ cells were stained with anti-chicken IgM-RPE (Southern Biotechnology Associates, Birmingham, Ala.), and analyzed on a FACScan with CellQuest software (BD Biosciences).

Single-cell PCR and sequence analysis were performed as described [47]. In brief, sIgM$^-$ cells were sorted, aliquoted to single wells, VA regions amplified and sequenced, and their sequences compared to the ΨVλ donors to determine if mutations were templated or nontemplated. The criterion for a templated mutation was that nine consecutive bases must be an exact match in donor and recipient. Sequences derived from two independently transfected lines. Only unique sequences were included for classification of the mutations.

Results

Permissive Chromatin Structure at Vλ and ΨVλ Donor Templates

In DT40 B cells, the functional Vλ gene at one Igλ allele is rearranged and expressed, and the other is unrearranged and not expressed. We characterized chromatin structure at the rearranged (V$λ_R$) and unrearranged (V$λ_U$) alleles and the ΨVλ array by chromatin immunoprecipitation (ChIP). ChIP was carried out with antibodies specific for lysine acetylation at the N-termini of histones H3 and H4. Recovered DNA was amplified in duplex PCR reactions; recovery normalized to an amplicon from the ovalbumin (Ova) gene, which is not expressed in B cells; and enrichment normalized to a total DNA input control (see Materials and Methods for details). The distinct genomic structure of V$λ_R$ and V$λ_U$ permit them to be distinguished by PCR with specific primers. ChIP demonstrated considerable enrichment of acetylated histones H3 and H4 (AcH3 and AcH4) at the rearranged V$λ_R$ gene. In a typical experiment, AcH3 was enriched more than 80-fold at V$λ_R$, and AcH4 more than 30-fold (FIG. 9B). In contrast, at the unrearranged V$λ_U$ allele, the levels of AcH3 and AcH4 were much lower than at V$λ_R$ (16-fold and 7-fold lower, respectively); and only a few fold enriched relative to input DNA.

Chromatin structure within the ΨVλ array was assayed by amplification with primers which interrogated seven sites, including a region between ΨVλ1 and the Vλ gene, ΨVλ1, ΨVλ5, ΨVλ13, ΨVλ18, ΨVλ24, ΨVλ25, and the upstream flanking region. (Due to a paucity of polymorphisms, the ΨVλ arrays at the two Igλ alleles in DT40 cannot be readily distinguished by PCR.) Strikingly, we observed considerable enrichment of AcH3 and AcH4 throughout the ΨVλ array (FIG. 9B). Enrichment was not proportional to distance from the transcribed Vλ$_R$ gene, as sites distant from Vλ$_R$ did not consistently display lower levels of enrichment than proximal sites (FIG. 9B). Thus, enrichment of acetylated histones within the ΨVλ array does not simply represent a graded spreading of chromatin modification from the transcribed Vλ$_R$ gene to sites upstream. The non-uniform chromatin structure of the locus suggests the presence of cis-elements that regulate chromatin structure at the ΨVλ array.

Figure 10A:
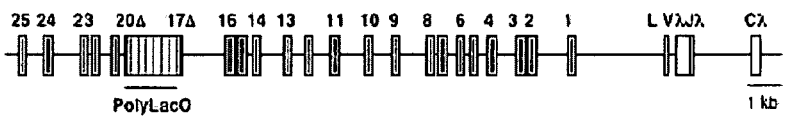
FIG. 10A-B. Reversible Tethering of GFP-LacI to the ΨVλ Array in DT40 PolyLacO-λR.

Reversible Tethering of LacI Fusion Proteins to the ΨVλ Array in DT40 PolyLacO-λ$_R$ Local modification of chromatin structure can be achieved by tethering regulators to DNA binding sites as appropriate fusion proteins. This strategy has, for example, been used to show that the heterochromatin protein HP1a, expressed as a fusion with lactose repressor (LacI-HP1), promotes a closed chromatin structure and inactivation of reporter genes neighboring a LacO repeat in *Drosophila* [61,62]; and to show that tethering of the vertebrate G9a histone methyltransferase to a GAL4 binding site within V(D)J minigene reporter impairs nonhomologous-mediated recombination of that construct [63]. The cell line, DT40 PolyLacO-λ$_R$, which is a DT40 derivative in which polymerized lactose operator (PolyLacO) has been inserted by homologous gene targeting between ΨVλ17-ΨVλ20, 17 kb upstream of the transcribed Vλ$_R$ (FIG. 10A). The PolyLacO insert is 3.8 kb in length and comprised of approximately 100 copies of a 20-mer operator [64]. Using this cell line, it is possible to assay the effects of tethered regulatory factors on homologous recombination in a physiological process within an endogenous locus, avoiding the need for a transgene reporter. Control experiments have shown that the PolyLacO tag does not affect cell proliferation, cell cycle, or Ig gene diversification.

Figure 10B:
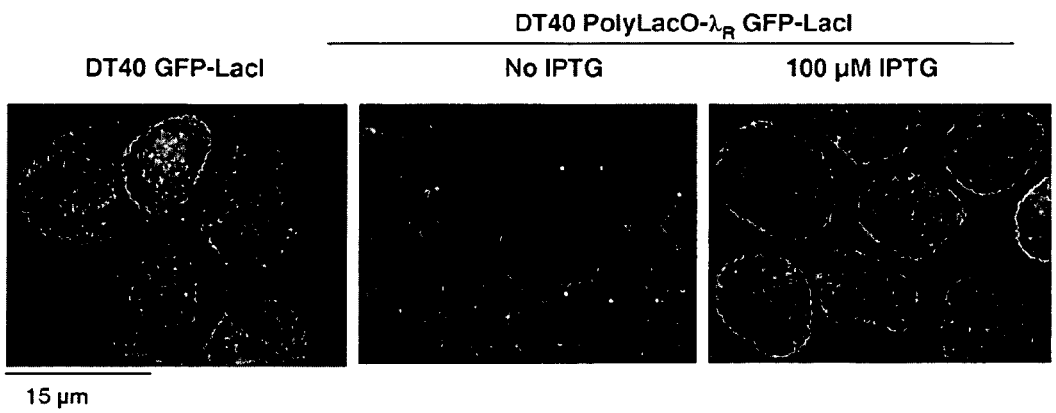

In DT40 PolyLacO-λ$_R$ GFP-LacI, which stably expresses enhanced green fluorescent protein fused to lactose repressor (GFP-LacI), the tagged λ$_R$ allele can be directly imaged by fluorescence microscopy and appears as a distinct dot in each cell (FIG. 10B, left). Tethering is reversible, as bright dots are not evident following overnight culture with 100 μM IPTG, which prevents LacI from binding to LacO (FIG. 10B, right).

Tethered HP1 Diminishes Modifications Characteristic of Active Chromatin at ΨVλ

Figure 11A:
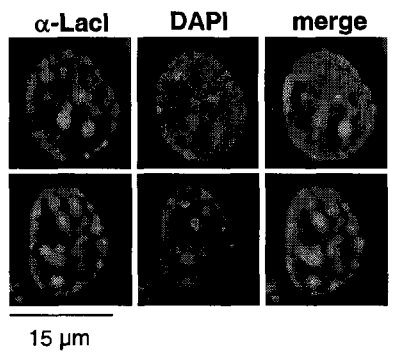
FIG. 11A-C. Tethered HP1 Diminishes Modifications Characteristic of Active Chromatin.

To manipulate chromatin structure at the ΨVλ array, we generated stable transfectants of DT40 PolyLacO-λ$_R$ which express the *Drosophila melanogaster* HP1 protein fused to LacI (LacI-HP1). HP1 is a non-histone heterochromatin protein that functions in heterochromatic gene silencing, the spreading of heterochromatin and histone deacetylation [58-60]. Tethered HP1 has been shown to promote a closed chromatin structure at adjacent genes [61,62, 66-68]. Staining DT40 PolyLacO-λ$_R$ LacI-HP1 transfectants with anti-LacI antibodies showed that LacI-HP1 colocalized with DAPI dense-regions corresponding to pericentric heterochromatin (FIG. 11A), behaving as a functional marker of heterochromatin [65].

Figure 11B:
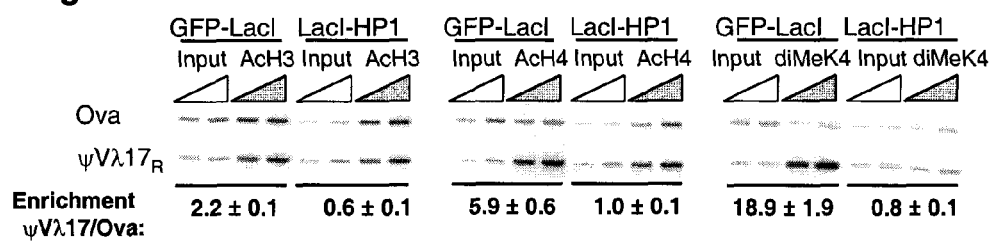

To ask if tethered LacI-HP1 altered chromatin structure, we assayed chromatin modifications at ΨVλ17. This is the only site in the ΨVλ array at which the rearranged and unrearranged alleles can be distinguished by use of specific PCR primers, due to a sequence polymorphism created during construction of DT40 PolyLacO. Following ChIP, DNA was amplified with PCR primers specific for the targeted rearranged allele (ΨVλ17$_R$). Enrichment of ΨVλ17$_R$ was compared to the nonexpressed ovalbumin gene (Ova) as an internal control; and normalized to the ΨVλ17$_R$:Ova enrichment ratio in total input DNA (see Material and Methods). AcH3 and AcH4 were enriched at ΨVλ17$_R$ in DT40 PolyLacO-λ$_R$ GFP-LacI controls 2.2-fold and 5.9-fold, respectively (FIG. 11B, C). These levels of enrichment are comparable to those documented in DT40 (FIG. 9B). (Note that analysis of modification at ΨVλ in the survey of the parental DT40 line necessarily includes both alleles, which may underestimate activating modifications at the rearranged allele. In contrast, analysis of modifications at ΨVλ17$_R$ interrogates only the active allele.) AcH3 and AcH4 were not enriched at ΨVλ17$_R$ in DT40 PolyLacO-λ$_R$ LacI-HP1 transfectants (0.6 and 1.0-fold, respectively; FIG. 11B, C), consistent with HP1-mediated silencing. HP1 can effect silencing by recruitment of a histone methyltransferase which modifies lysine 9 of histone H3 [66-68], but may also promote silencing independently of this modification [61]. ChIP using antibodies against either di- and tri-methylated H3 (K9) did not reveal clear enrichment of the H3 K9-Me modification (data not shown). Methylation of lysine 4 (diMeK4) of histone H3 is associated with transcription and generally exhibits an overlapping distribution with acetylation [69,70]. Assays of diMeK4(H3) at ΨVλ17$_R$ demonstrated that this modification was 18.9-fold enriched in DT40 PolyLacO-λ$_R$ GFP-LacI cells, but at background levels in DT40 PolyLacO-λ$_R$ LacI-H P1 cells (FIG. 11B, C).

Figure 11C:
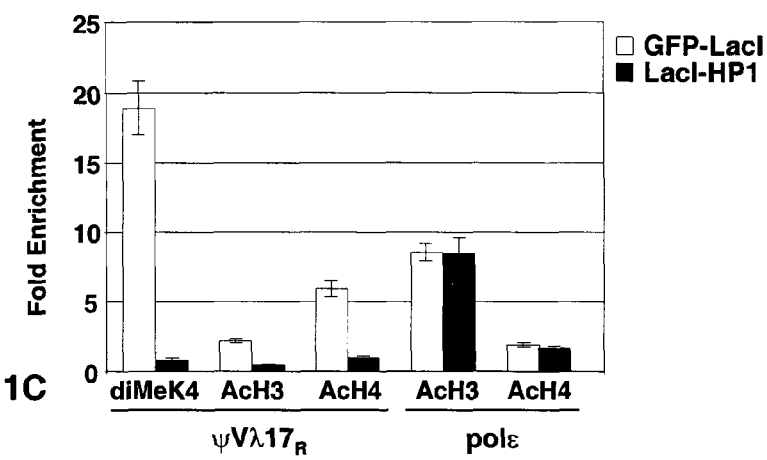

HP1 promotes maintenance and spreading of heterochromatin [66]. To verify that changes in chromatin structure promoted by tethered HP1 did not spread throughout the chromosome, we examined another site near the λ light chain locus on chromosome 15, the gene encoding the catalytic subunit of DNA polε. DNA polε is ubiquitously expressed and essential for chromosomal replication in eukaryotes [71], and it is encoded by a gene mapping approximately 2.1 Mb from Igλ. We found no difference in enrichment of AcH3 at the polε promoter region in the DT40 PolyLacO-λ$_R$ LacI-HP1 transfectants relative to DT40 PolyLacO-λ$_R$ GFP-LacI controls (polε/Ova enrichment 8.5-fold and 8.4-fold, respectively; FIG. 3C). Similarly, there was no difference in AcH4 at the polε promoter in the DT40 PolyLacO-λ$_R$ LacI-HP1 transfectants relative to DT40 PolyLacO-λ$_R$ GFP-LacI controls (polε/Ova enrichment 1.9-fold and 1.7-fold, respectively; FIG. 11C). Thus, tethering of LacI-HP1 at ΨVλ caused local modifications in chromatin structure, diminishing the AcH3, AcH4 and diMeK4(H3) modifications characteristic of open chromatin at ΨVλ17$_R$, and causing chromatin to adopt a less permissive state.

Tethered HP1 Does Not Affect Vλ Gene Expression

Figure 12A:
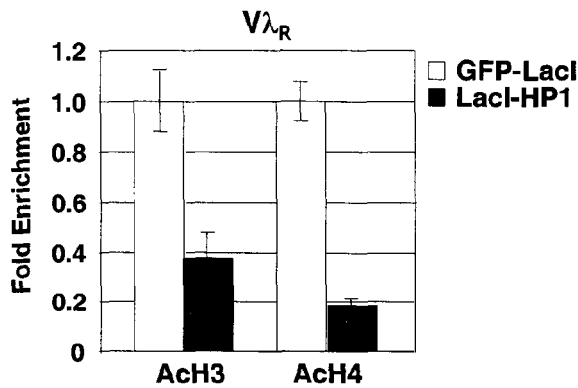
FIG. 12A-C. Tethered HP1 Does Not Affect IgA Expression.
Figure 12B:
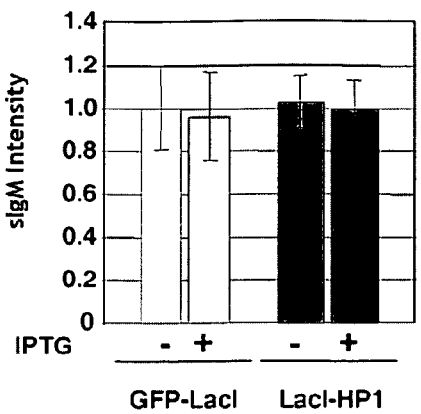
Figure 12C:
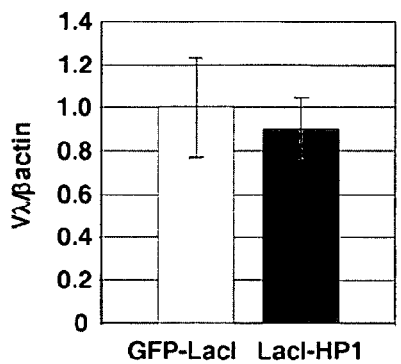

We asked how tethered HP1 affected AcH3 and AcH4 levels at the expressed Vλ$_R$ by comparing these modifications in DT40 PolyLacO-λ$_R$ LacI-HP1 cells and the DT40 PolyLacO-λ$_R$ GFP-LacI control transfectants (FIG. 12A). Tethered HP1 diminished AcH3 and AcH4 levels to approximately 40% and 20% of the control levels, respectively. To ask if this affected gene expression, we assayed both surface IgM (sIgM) expression and Vλ transcript levels. Staining cells with mouse anti-chicken IgM showed that sIgM expression was comparable in DT40 PolyLacO-λ$_R$ GFP-LacI and DT40 PolyLacO-λ$_R$ LacI-HP1 lines, cultured in either the presence or absence of IPTG (FIG. 12B). Vλ transcript levels were assayed by quantitative RT-PCR of RNA harvested from DT40 PolyLacO-λ$_R$ GFP-LacI and D140 PolyLacO-λ$_R$ LacI-HP1 cells, and normalized to β-actin as a control (FIG. 12C). No significant difference was observed between VA transcript levels in the two cell lines, demonstrating that transcription is not affected by tethering of HP1 within the ΨVλ array. Thus tethered LacI-HP1 did not affect expression of the downstream Ig gene, although it did diminish AcH3 and AcH4 levels at Vλ$_R$. The very high AcH3 and AcH4 levels characteristic of Vλ (FIG. 9B, FIG. 12A) are therefore not essential to maintain high levels of gene expression.

Tethered HP1 Alters Local Chromatin Structure

Figure 9A:
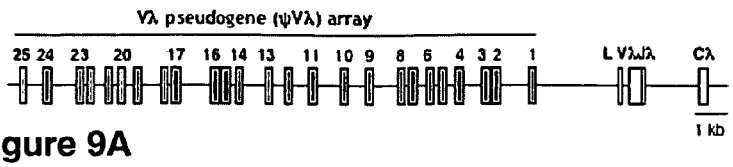
FIG. 9A-B. Chromatin Modification at the DT40 Igλ Locus.
Figure 9B:
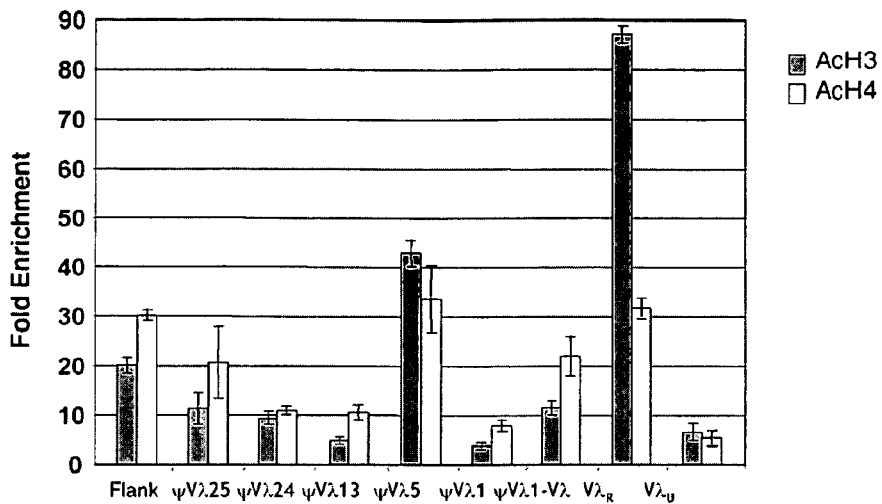
Figure 13A:
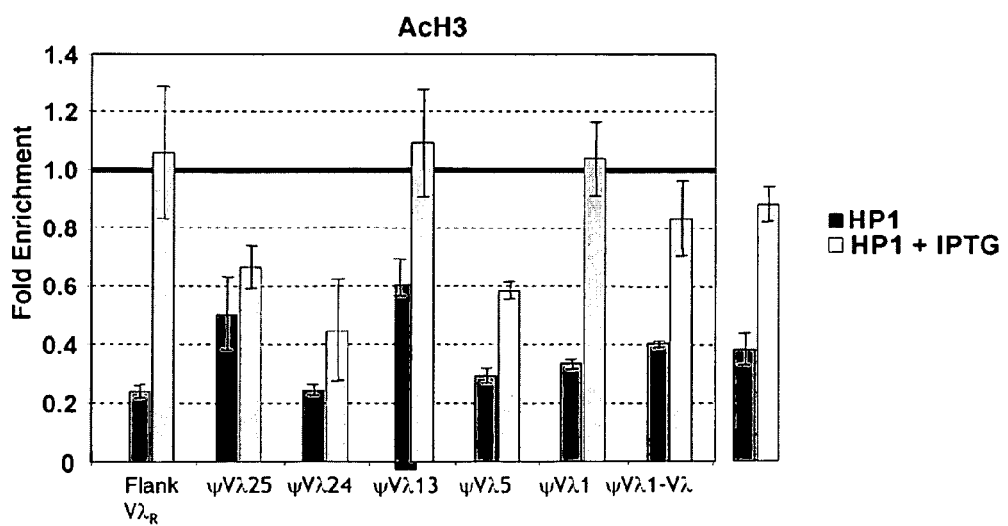
FIG. 13A-B. Tethered HP1 Decreases Histone Acetylation throughout the ΨVλ Array.

To assess how extensive the chromatin effects of LacI-HP1 were, we examined AcH3 and AcH4 levels throughout the Igλ light chain locus at the same amplicons examined in FIG. 9, including one in the flank, six in the ΨVλ array, as well as at the expressed Vλ. Levels of modification were determined by comparing ΨVλ17$_R$:Ova ratios of immunoprecipitated and input conditions, as in FIG. 11B. AcH3 modifications at the sites surveyed ranged from 24% to 63% of the levels at the same sites in the controls (FIG. 13A, dark bars); and the average level of H3 acetylation across all of the sites was 38% of the PolyLacO-λ$_R$ GFP-LacI control. Culture of DT40 PolyLacO-λ$_R$ LacI-HP1 transfectants for three days with 250 µM IPTG increased acetylation of H3 at all eight sites surveyed (FIG. 13A, compare dark and light bars). The effects of IPTG culture were somewhat variable, but at most sites IPTG culture restored levels of AcH3 to at least 45% of the level in the DT40 PolyLacO-λ$_R$ GFP-LacI control cells; with an average of over 80%. Thus, the chromatin modifications at ΨVλ17$_R$ in DT40 PolyLacO-λ$_R$ LacI-HP1 cells resulted directly from tethered LacI-HP1, and were largely reversible.

Figure 13B:
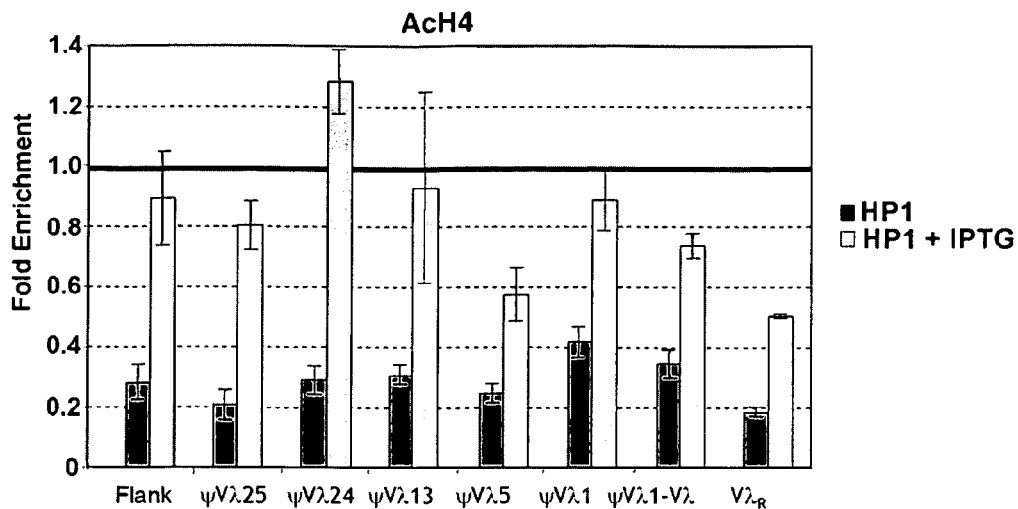

H4 acetylation was surveyed at the same eight sites (FIG. 13B, dark bars). AcH4 modifications were found to range from 18% to 42% of control levels; and the average level was 29% of the control cell line. Culture with IPTG for three days increased acetylation of H4 at all eight sites surveyed (FIG. 13B, compare dark and light bars), restoring levels of H4 acetylation to at least 57% of the level in the DT40 PolyLacO-λ$_R$ GFP-LacI control cells; with an average of over 80%. Moreover, IPTG can at least partially reverse the effects of LacI-HP1.

These results show that the observed chromatin modifications in the ΨVλ array are due to tethering of HP1. Moreover, the fact that these modifications are reversible shows that an active mechanism reverses histone modifications imposed by tethering chromatin modification factors at ΨVλ.

Tethered HP1 Impairs Templated Mutagenesis.

Figure 14A:
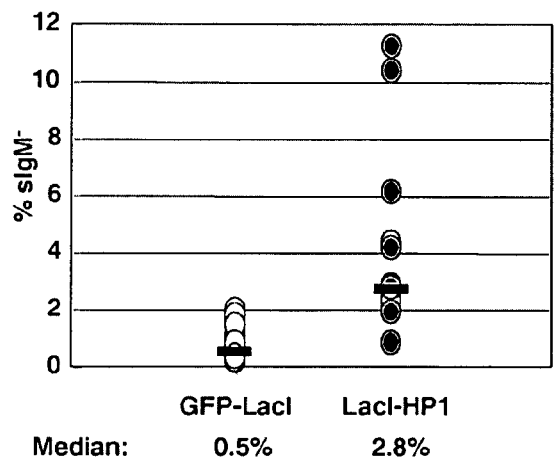

The ability to manipulate chromatin structure at ΨVλ by tethering LacI-HP1 (FIGS. 11-13) enabled us to directly ask whether and how chromatin structure influences Ig gene conversion. We used the sIgM loss variant assay to determine if tethered LacI-HP1 affected the clonal rate of sequence diversification of the rearranged Vλ$_R$ gene. This fluctuation assay measures the fraction of variant cells which no longer express structurally intact sIgM, and thus scores mutation events resulting from either gene conversion or point mutagenesis [47,50]. Independent clonal derivatives of DT40 PolyLacO-λ$_R$ GFP-LacI and DT40 PolyLacO-λ$_R$ LacI-HP1 were established by limiting dilution cloning of sIgM cells, and the fraction of sIgM$^-$ cells in each population determined by flow cytometry of cells cultured for 4 weeks, and then stained with anti-IgM antibody. The median sIgM loss rate was 0.5% for DT40 PolyLacO-λ$_R$ GFP-LacI cells and 2.8% for DT40 PolyLacO-λ$_R$ LacI-HP1 cells (FIG. 14A). This corresponds to 5.6-fold acceleration of clonal diversification rates in LacI-HP1 transfectants relative to GFP-LacI controls.

Ig gene diversification in chicken B cells occurs predominantly by gene conversion (templated mutation); but if gene conversion is impaired, for example by the absence of essential factors, repair can create a significant fraction of nontemplated mutations [50-55]. This is typically accompanied by an increase in the clonal diversification rate, because the ΨVλ templates for gene conversion are about 80% identical to the rearranged gene, and a significant fraction of DNA lesions that are repaired by gene conversion do not undergo any alteration of sequence; in contrast, repair by a mutagenic polymerase is more likely to alter DNA sequence. To determine how tethering of HP1 accelerated diversification, we sorted single sIgM$^-$ cells from the DT40 PolyLacO-λ$_R$ GFP-LacI and DT40 PolyLacO-λ$_R$ LacI-HP1 transfectants, amplified expressed Vλ regions by single-cell PCR, and sequenced these regions. Sequence changes were categorized as templated if they were within a tract containing two or more mutations and the tract was an exact match to at least 9 bp of a donor ΨVλ sequence; and as ambiguous if they consisted of only a single base change, but did match at least 9 bp of a donor ΨVλ sequence. Nontemplated events, consisting of point mutations, deletions, and insertions, were also scored. In the control DT40 PolyLacO-λ$_R$ GFP-LacI transfectants, 54 templated events and 2 ambiguous events were documented among 70 unique mutations; thus most events (77%) were templated, and a small fraction of events (20%) were point mutations (FIG. 14B, left; FIG. 15). Strikingly, in DT40 PolyLacO-λ$_R$ LacI-HP1 cells, point mutations predominated (59%), accompanied by deletions (8%) and insertions (14%); while only 1 clearly templated event and 6 ambiguous events were documented among 36 unique mutations (FIG. 14B, right; FIG. 15). Thus only 3% of mutations were clearly templated, and even including the ambiguous class of potentially templated mutations, templating could account for no more than 19% of mutation. Statistical comparisons showed that the difference between the fraction of clearly templated mutations in DT40 PolyLacO-λ$_R$ GFP-LacI control cells and DT40 PolyLacO-λ$_R$ LacI-HP1 transfectants (77% compared to 3%) was highly significant (P=7.1×10$^{-7}$; Fisher's exact test). The difference in the fraction of ambiguous, potentially templated mutations in the control cells (3%) and HP1 transfectants (17%) is also significant (P=0.05; Fisher's exact test). This suggests that some mutations in this category may arise as a result of limitations on the length of a gene conversion tract imposed by nonpermissive donor chromatin. Thus, tethering of HP1 accelerated clonal rates of mutagenesis by impairing templated mutation.

Discussion

Gene conversion at the chicken Ig loci uses an array of upstream ΨV donors as templates for homology-directed repair of lesions targeted to the rearranged and transcribed V genes. This example shows that, in chicken B cells carrying out active Ig gene conversion, chromatin within the donor ΨVλ array is characterized by enrichment of acetylated H3 and H4, modifications that correlate with an open chromatin structure. We directly demonstrated the importance of permissive chromatin structure for Ig gene conversion by showing that tethering the heterochromatin protein HP1 to the ΨVλ donor array caused local changes in chromatin structure, diminishing the AcH3, AcH4 and diMeK4(H3) modifications characteristic of open chromatin. Although these changes were not accompanied by the Me-K9 (H3) modification characteristic of closed chromatin, they caused the region to adopt a state less permissive for gene conversion. Tethering of HP1 was accompanied by a dramatic shift in the Ig Vλ mutation spectrum, so that templated mutations were in the minority and point mutations predominated. Importantly, this effect on mutagenesis was correlated with a change in chromatin structure and not changes in expression of the locus. Thus, chromatin structure can dictate whether gene conversion occurs at a endogenously generated DNA lesion.

The Mechanism of Gene Conversion within a Complex Chromatin Landscape

Gene conversion at VA results from priming of new DNA synthesis at the 3' end of a break using a ΨVλ region as template. Gene conversion requires synapsis between the donor and recipient DNA, as well as access to the donor by factors that carry out homology-directed repair. The elevated levels of H3 and H4 acetylation characteristic of the ΨVλ array in wild type DT40 are evidence of a relaxed chromatin structure, which would increase the accessibility of the ΨVλ genes to trans-acting factors and also create a three-dimensional architecture that is favorable for sequence synapsis.

HP1 tethered within the ΨVλ donor array impaired gene conversion at the rearranged Vλ$_R$, without affecting VA gene expression. Chromatin changes caused by tethered HP1 may impair gene conversion by impeding access of repair factors and the invading strand to the donor template. Tethered HP1 may also contribute to larger chromosomal architecture that affects the mechanics of DNA repair pathways, such as looping necessary to juxtapose donor and recipient sequences. The point mutations that accumulated in LacI-HP1 transfectants are typical of thwarted recombinational repair, and are characteristic of cells lacking either trans-acting factors essential for recombination [49-55] or some or all of the ΨV donor array [56]. HP1 regulates chromatin structure and heterochromatic gene silencing in two ways, by partnering with a histone methyltransferase [66] and by recruiting histone deacetylases [60]. Tethered HP1 caused modifications characteristic of a nonpermissive chromatin structure within ΨVλ.

Histone acetylation has been documented at actively transcribed mammalian Ig genes undergoing somatic hypermutation and class switch recombination, but whether hyperacetylation contributes to targeting of diversification has yet to be resolved [72-76]. A connection between histone acetylation and gene conversion was suggested by experiments showing that treatment of DT40 cells with the histone deacetylase inhibitor, trichostatin A, promotes genomewide histone deacetylation accompanied by increased gene conversion at Vλ$_{R[}$77]. However, the interpretation of those results is complicated by the fact that the effects of trichostatin A are genomewide, and not specific. The DT40 PolyLacO-λ$_R$ cell line permits local manipulation of chromatin structure, avoiding that complication. Moreover, we were able to demonstrate that the effects of tethering a LacI-H P1 fusion protein were largely reversed upon culture with IPTG, so an active mechanism must determine chromatin modification at ΨVλ.

For studies of homologous recombination, the DT40 Poly-LacO-λ$_R$ B cell line has the further advantage that Ig gene conversion is a physiological process within an endogenous locus, avoiding the need for a transgene reporter.

Chromatin Structure, Genome Stability, Aging and Gene Therapy

The importance of chromatin structure to the outcome of homologous recombination has implications for understanding mechanisms that normally maintain genomic stability. There are vast numbers of repetitive elements distributed throughout the vertebrate genome, and recombination between these elements can lead to genomic instability [78]. In the human genome, there are approximately one million Alu elements, and recombination between Alu elements can cause duplications leading to tumorigenesis and genetic disease [79,80]. Histones carrying repressive modifications are enriched at repetitive elements [81]. These modifications undoubtedly maintain transcriptional repression; our results suggest they may also contribute to suppression of recombination.

Loss of heterozygosity (LOH) occurs as a result of unequal mitotic recombination between homologs at allelic sites. The mechanism of LOH is of particular interest, because it contributes to loss of tumor suppressor gene function leading to tumorigenesis [82]. Recent experiments have demonstrated an age-dependent increase in LOH in *S. cerevisiae* [83] and in reporter genes in *Drosophila* germ cells [84]; and an increase in homologous recombination in mouse pancreatic cells [85]. Mechanisms proposed to explain age-associated LOH include elevated rates of DNA damage, changes in the cell cycle distribution, and inactivation of homology-independent repair pathways with aging. The results suggest another possibility, that relaxation of chromatin structure may accompany aging and promote a genome-wide increase in homologous recombination in aging cells. This possibility is supported by recent analysis of *Drosophila* [86], as well as by recent evidence that the mutation in lamin A responsible for Hutchinson-Gilford Progeria Syndrome leads to a genomewide loss of H3 methylation [87].

The finding that chromatin structure regulates homologous recombination also has practical ramifications. Considerable current effort is directed toward developing strategies that harness a cell's capacity for homology-dependent repair to promote gene therapy, by providing an intact donor gene to replace a deficient target gene [88]. The results suggest that permissive structure at the donor will be an important design parameter in developing donor genes for therapeutic applications.

References

1. West S C (2003). Nat Rev Mol Cell Biol 4: 435-445.
2. Lee G S, et al. (2004). Cell 117: 171-184.
3. Essers J, Houtsmuller A B, Kanaar R (2006). Methods Enzymol 408: 463-485.
4. Wyman C, Kanaar R (2006). Annu Rev Genet 40: 363-383.
5. Weinstock D M, Richardson C A, Elliott B, Jasin M (2006). DNA Repair (Amst) 5: 1065-1074.
6. Sugawara N, Haber J E (2006). Methods Enzymol 408: 416-429.
7. Brugmans L, Kanaar R, Essers J (2007). Mutat Res 614: 95-108.
8. Gaiter P M, Vidanes G M, Toczyski D P (2005). Trends Biochem Sci 30: 63-66.
9. Rodrigue A, et al. (2006). Embo J 25: 222-231.
10. Haber J E (2000). Trends Genet 16: 259-264.
11. Rooney S, Chaudhuri J, Alt F W (2004). Immunol Rev 200: 115-131.
12. Caldecott K W (2003). DNA Repair (Amst) 2: 955-969.
13. Sung J S, Demple B (2006). Febs J 273: 1620-1629.
14. Rogakou E P, et al. (1998). J Biol Chem 273: 5858-5868.
15. Burma S, et al. (2001). J Biol Chem 276: 42462-42467.
16. Ward I M, Chen J (2001). J Biol Chem 276: 47759-47762.
17. Rogakou E P, et al. (1999). J Cell Biol 146: 905-916.
18. Unal E, et al. (2004). Mol Cell 16: 991-1002.
19. Paull T T, et al. (2000). Curr Biol 10: 886-895.
20. van Attikum H, et al. (2004). Cell 119: 777-788.
21. Morrison A J, et al. (2004). Cell 119: 767-775.
22. Downs J A, et al. (2004). Mol Cell 16: 979-990.
23. Jazayeri A, McAinsh A D, Jackson S P (2004). Proc Natl Acad Sci U S A 101: 1644-1649.
24. Tamburini B A, Tyler J K (2005). Mol Cell Biol 25: 4903-4913.
25. Schildkraut E, Miller C A, Nickoloff J A (2006). Mol Cell Biol 26: 3098-3105.
26. Arakawa H, Buerstedde J M (2004). Dev Dyn 229: 458-464.
27. Maizels N (2005). Annu Rev Genet 39: 23-46.
28. Thompson C B, Neiman P E (1987). Cell 48: 369-378.
29. Reynaud C A, et al. (1987). Cell 48: 379-388.
30. Reynaud C A, et al. (1989). Cell 59: 171-183.

31. Buerstedde J M, et al. (2002). Nucleic Acids Res 30: 230-231.
32. Yamazoe M, Sonoda E, Hochegger H, Takeda S (2004). DNA Repair (Amst) 3: 1175-1185.
33. Sale J E (2004). DNA Repair (Amst) 3: 693-702.
34. Muramatsu M, et al. (2000). Cell 102: 553-563.
35. Revy P, Muto T, Levy Y, Geissmann F, Plebani A, et al. (2000). Cell 102: 565-575.
36. Arakawa H, Hauschild J, Buerstedde J M (2002). Science 295: 1301-1306.
37. Harris R S, Sale J E, Petersen-Mahrt S K, Neuberger M S (2002). Curr Biol 12: 435-438.
38. Petersen-Mahrt S K, Harris R S, Neuberger M S (2002). Nature 418: 99-103.
39. Bransteitter R, et al. (2003). Proc Natl Acad Sci U S A 100: 4102-4107.
40. Chaudhuri J, Tian M, Khuong C, Chua K, Pinaud E, et al. (2003). Nature 422: 726-730.
41. Ramiro A R, Stavropoulos P, Jankovic M, Nussenzweig M C (2003). Nat Immunol 4: 452-456.
42. Di Noia J, Neuberger M S (2002). Nature 419: 43-48.
43. Rada C, et al. (2002). Curr Biol 12: 1748-1755.
44. Imai K, et al. (2003). Nat Immunol 4: 1023-1028.
45. Di Noia J M, Neuberger M S (2004). Eur J Immunol 34: 504-508.
46. Saribasak H, et al. (2006). J Immunol 176: 365-371.
47. Yabuki M, Fujii M M, Maizels N (2005). Nat Immunol 6: 730-736.
48. Larson E D, Cummings W J, Bednarski D W, Maizels N (2005). Mol Cell 20: 367-375.
49. Takata M, et al. (2000). Mol Cell Biol 20: 6476-6482.
50. Sale J E, et al. (2001). Nature 412: 921-926.
51. Niedzwiedz W, et al. (2004). Mol Cell 15: 607-620.
52. Hatanaka A, et al. (2005). Mol Cell Biol 25: 1124-1134.
53. Yamamoto K, Hirano S, Ishiai M, Morishima K, et al. (2005). Mol Cell Biol 25: 34-43.
54. McIlwraith M, et al. (2005). Mol Cell 20: 783-792.
55. Kawamoto T, Araki K, Sonoda E, Yamashita Y M, et al. (2005). Mol Cell 20: 793-799.
56. Arakawa H, Saribasak H, Buerstedde J M (2004). PLoS Biol 2: E179.
57. McCormack W T, Thompson C B (1990). Genes Dev 4: 548-558.
58. James T C, Eissenberg J C, Craig C, Dietrich V, et al. (1989). Eur J Cell Biol 50: 170-180.
59. Eissenberg J C, et al. (1990). Proc Natl Acad Sci U S A 87: 9923-9927.
60. Nielsen A L, et al. (1999). Embo J 18: 6385-6395.
61. Li Y, Danzer J R, Alvarez P, Belmont A S, Wallrath L L (2003). Development 130: 1817-1824.
62. Danzer J R, Wallrath L L (2004). Development 131: 3571-3580.
63. Osipovich O, Milley R, Meade A, Tachibana M, et al. (2004). Nat Immunol 5: 309-316.
64. Robinett C C, Straight A, Li G, Willhelm C, et al. (1996). J Cell Biol 135: 1685-1700.
65. Verschure P J, et al. (2005). Mol Cell Biol 25: 4552-4564.
66. Bannister A J, et al. (2001). Nature 410: 120-124.
67. Jacobs S A, Taverna S D, Zhang Y, et al. (2001). Embo J 20: 5232-5241.
68. Lachner M, O'Carroll D, Rea S, et al. (2001). Nature 410: 116-120.
69. Strahl B D, Ohba R, Cook R G, Allis C D (1999). Proc Natl Acad Sci U S A 96: 14967-14972.
70. Litt M D, Simpson M, Gaszner M, Allis C D, Felsenfeld G (2001). Science 293: 2453-2455.
71. Araki H, Ropp P A, Johnson A L, Johnston L H, et al. (1992). Embo J 11: 733-740.
72. Nambu Y, Sugai M, Gonda H, Lee C G, Katakai T, et al. (2003). Science 302: 2137-2140.
73. Woo C J, Martin A, Scharff M D (2003). Immunity 19: 479-489.
74. Li Z, Luo Z, Scharff M D (2004). Proc Natl Acad Sci U S A 101: 15428-15433.
75. Odegard V H, Kim S T, Anderson S M, et al. (2005). Immunity 23: 101-110.
76. Wang L, Whang N, Wuerffel R, Kenter A (2006). J Exp Med 203: 215-226.
77. Seo H, Masuoka M, Murofushi H, et al. (2005). Nat Biotechnol 23: 731-735.
78. Stankiewicz P, Lupski J R (2002). Trends Genet 18: 74-82.
79. Batzer M A, Deininger P L (2002). Nat Rev Genet 3: 370-379.
80. Aplan P D (2006). Trends Genet 22: 46-55.
81. Martens J H, O'Sullivan R J, et al. (2005). Embo J 24: 800-812.
82. Tycko B (2003). Ann N Y Acad Sci 983: 43-54.
83. McMurray M A, Gottschling D E (2003). Science 301: 1908-1911.
84. Preston C R, Flores C, Engels W R (2006). Curr Biol 16: 2009-2015.
85. Wiktor-Brown D M, Hendricks C A, et al. (2006). Proc Natl Acad Sci U S A 103: 11862-11867.
86. Peng J C, Karpen G H (2007). Nat Cell Biol 9: 25-35.
87. Shumaker D K, Dechat T, et al. (2006). Proc Natl Acad Sci U S A 103: 8703-8708.
88. Porteus M H, Connelly J P, Pruett S M (2006). PLoS Genet 2: e133.
89. Larson E D, Duquette M L, Cummings W J, et al. (2005). Curr Biol 15: 470-474.
90. Liu Y, Maizels N (2000). EMBO Reports 1: 85-90.

Example 5

Gene Conversion Accelerated by Distinct Modifications of Chromatin

This example demonstrates that the efficiency of repair is determined by chromatin structure of the donor. The analysis takes advantage of a cis-regulatory site (polymerized lactose operators, PolyLacO) inserted just upstream of the transcribed and diversifying VA gene in the chicken DT40 B cell line. The data show that tethering either the activator, VP16, or the histone chaperone, HIRA, alters local chromatin structure and accelerates gene conversion approximately 10-fold. While these two factors have comparable functional outcomes, they have distinct effects on chromatin structure. VP16 tethering increases local levels of acetylated histones H3 and H4; while HIRA tethering increases nucleosome density. Thus, comparable functional outcomes can be achieved by distinct chromatin modifications.

Materials and Methods

Chromatin Immunoprecipitation (ChIP).

ChIP was carried out as previously described (Cummings et al., 2007). For all experiments at least two chromatin preparations from at least two independent stably-transfected lines were analyzed. Figures present one representative experiment in which results from analysis of four separate amplifications were used to calculate a standard deviation. Four separate amplifications of serial dilutions of template DNA were carried out, to establish that the measured product intensities were within the linear range. Enrichment of the experimental amplicon was normalized to enrichment of an internal control amplicon from the ovalbumin (Ova) gene, amplified in the same tube by duplex PCR; and enrichment upon ChIP with specific antibodies was normalized to parallel experiments in which ChIP was carried out with total input DNA controls. Inclusion of the Ova internal control amplicon enabled us to normalize for IP efficiency, background carryover, and differences in gel loading. Enrichment=[(ΨVλ/Ova)Ab]/[ΨVλ/Ova)Input]. As an additional control, the ratio of the experimental and control amplicons in the total input control was compared to a control ChIP with polyspecific IgG; in all cases, enrichment in input and IgG controls were essentially equal. Data are presented for representative experiments; standard deviations were calculated from four separate amplifications of serial dilutions of template DNA.

Antibodies used were: anti H3 CT-pan, anti-AcH3 (06-599), anti-AcH4 (06-866), and dimethylated H3(K4) (07-030) from Upstate (Lake Placid, N.Y.).

PCR primers for ChIP were:

```
Vλ_R:
             (SEQ ID NOS: 5-28, respectively).
5'-GCCGTCACTGATTGCCGTTTTCTCCCCTC-3'
and

5'-CGAGACGAGGTCAGCGACTCACCTAGGAC-3';

promoter region between ψVλ1 and Vλ:
5'-CTGTGGCCTGTCAGTGCTTA-3'
and

5'-GCAGGGAACCACAAGAACAT-3';

ψVλ1:
5'-GGGACTTGTGTCACCAGGAT-3'
and

5'-CGCAGTCACATGTGGAATATC-3';

ψVλ5:
5'-GAGCCCCATTTTCTCTCCTC-3'
and

5'-GAGATGTGCAGCAACAAGGA-3';

ψVλ13:
5'-CCCTCTCCCTATGCAGGTTC-3'
and

5'-CCCCTATCACCATACCAGGA-3';

ψVλ18:
5'-CCATTTTCTCCCCTCTCTCC-3'
and

5'-TCACCCTACAGCTTCAGTGC-3';

ψVλ24:
5'-CCATTTTCTCCCCTCTCTCC-3'
and

5'-CAGCCCATCACTCCCTCTTA-3';

ψVλ25:
5'-TCTGTTGGTTTCAGCACAGC-3'
and

5'-GCAGTTCTGTGGGATGAGGT-3';

ψVλ upstream flank:
5'-GGCTCCTGTAGCTGATCCTG-3'
and

5'-GTTCTTTGCTCTTCGGTTGC-3';

ψVλ17 at the PolyLacO-targeted allele:
5'-TAGATAGGGATAACAGGGTAATAGC-3'
and

5'-AGGGCTGTACCTCAGTTTCAC-3';

OVA:
5'-ATTGCGCATTGTTATCCACA-3'
and

5'-TAAGCCCTGCCAGTTCTCAT-3';

polε:
5'-GGGCTGGCTCATCAACAT-3'
and

5'-CTGGGTGGCCACATAGAAGT-3'.
```

MNase Digestion and Southern Blotting.

Nuclei were prepared and digests were performed with 0, 3, 7, 15, 30, and 60 units of MNase as described (Prioleau et al., 1999). Following MNase digestion, DNA was extracted three times with phenol:chloroform:isoamyl alcohol, and precipitated with ethanol. Twenty micrograms of DNA were loaded on a gel, resolved by electrophoresis, and transferred for Southern hybridization. The lacO probe was labeled by random priming, using as template a fragment approximately 500 bp in length containing polyLacO repeats.

Fluorescence Imaging.

For fluorescence imaging, cells ($2 \times 10^5$) were cytospun onto glass slides and fixed with 2% paraformaldehyde for 15 min. To visualize the nucleus, cells were stained with DAPI (Sigma, Saint Louis, Mo.). Fluorescent images were acquired using the DeltaVision microscopy system (Applied Precision) and processed with softWoRx software (Applied Precision).

RT-PCR.

RNA was harvested from cells using TRIzol Reagent (Invitrogen). Vλ and β-actin transcripts were amplified following dilution of the template. The primers for amplification of Vλ were 5'-GTCAGCAAACCCAGGAGAAAC-3' (SEQ ID NO: 3) and 5'-AATCCACAGTCACTGGGCTG-3' (SEQ ID NO: 4). The primers for amplification of β-actin have been described (Arakawa et al., 2002).

Quantitation of sIgM Loss Variants and Sequence Analysis.

The sIgM loss variant assay, which measures the accumulated sIgM-loss variants resulting from frameshift or nonsense mutations in mutated V regions, was used to quantitate Ig V region diversification (Sale et al., 2001; Yabuki et al., 2005; Cummings et al., 2007). In brief, sIgM⁺ cells were isolated by flow cytometry followed by limiting dilution cloning, and expanded for 4 weeks. To quantitate the fraction of sIgM⁻ cells, approximately $1 \times 10^6$ cells were stained with anti-chicken IgM-RPE (Southern Biotechnology Associates, Birmingham, Ala.), and analyzed on a FACScan with CellQuest software (BD Biosciences).

Single-cell PCR and sequence analysis were performed as described (Yabuki et al., 2005; Cummings et al., 2007). In brief, sIgM⁻ cells were sorted, aliquoted to single wells, Vλ regions amplified and sequenced, and their sequences compared to the ΨVλ donors to determine if mutations were templated or nontemplated. The criterion for a templated mutation was that nine consecutive bases must be an exact match in donor and recipient. Sequences derived from two independently transfected lines. Only unique sequences were included for classification of the mutations.

Results
Tethered VP16 Accelerates Gene Conversion

Figure 16A:
FIG. 16A-E. Ig gene conversion is accelerated by VP16 tethered to the ΨVλ array.

If repressive donor chromatin structure impairs gene conversion, activating modifications might promote gene conversion. To test this possibility, we took advantage of the DT40 PolyLacO-λ cell line constructed by our laboratory. In this cell line, polymerized lactose operator (PolyLacO) has been inserted into the ΨVλ array between ΨVλ17-ΨVλ20, 17 kb upstream of the expressed Vλ gene (FIG. 16A; Example 4). This allows us to assay the effects of tethered regulatory factors expressed as fusions with lactose repressor. Control experiments have shown that the PolyLacO tag does not affect cell proliferation, cell cycle profile, or Ig gene diversification.

Figure 16B:
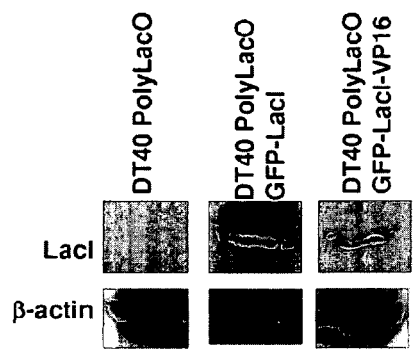
Figure 16C:
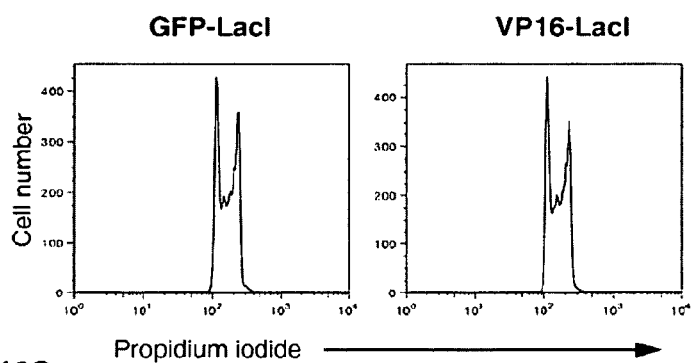
Figure 16D:
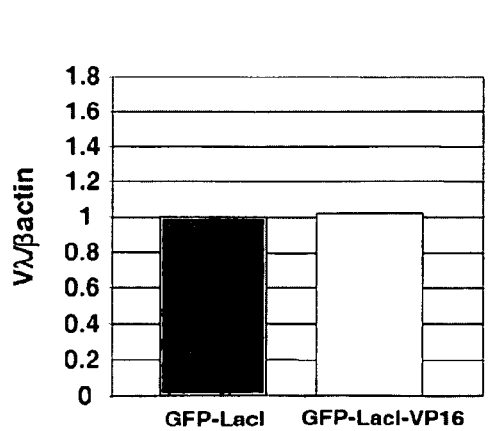
Figure 16E:
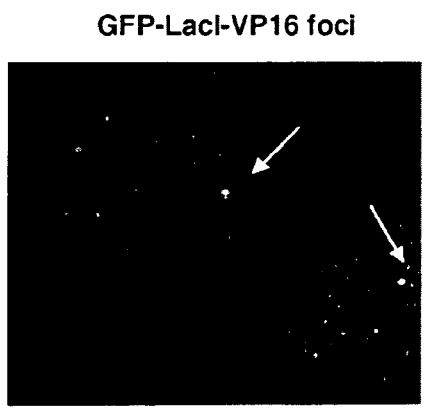

Loss of histone acetylation within the ΨVλ donors correlates with diminished gene conversion at Vλ (Example 4). We therefore tested the effect of VP16, a potent transactivator derived from herpesvirus, which has been associated with the relaxation of chromatin and recruitment of histone acetyltransferases (Tumbar et al., 1999; Carpenter et al., 2005). We generated DT40 PolyLacO-$λ_R$ transfectants stably expressing GFP-LacI-VP16. Western blotting confirmed protein expression (FIG. 16B). Cell cycle profile (FIG. 16C) and levels of λ transcription (FIG. 16D) were unaltered relative to control DT40 PolyLacO-λ GFP-LacI transfectants. Fluorescent imaging of the DT40 PolyLacO-λ GFP-LacI-VP16 transfectants showed a single green spot within the nucleus, evidence of GFP-LacI-VP16 expression and binding to PolyLacO (FIG. 16E).

Figure 17A:
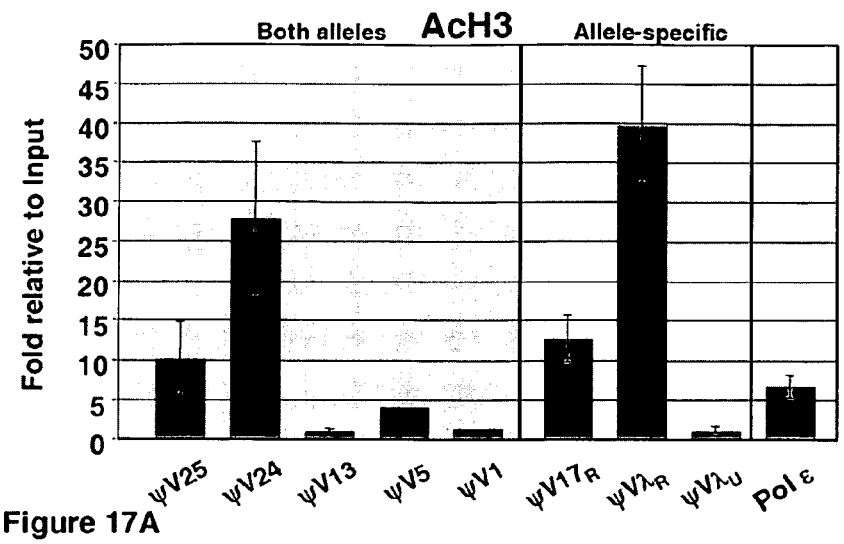
FIG. 17A-C. AcH3 and AcH4 levels are increased and Ig gene conversion is accelerated by VP16 tethered to the ΨVλ array.

We assayed histone acetylation in PolyLacO-λ GFP-LacI-VP16 and control DT40 PolyLacO-λ GFP-LacI cells. The ΨVλ array was assayed by amplification with primers specific for seven sites, including the promoter region between ΨVλ1 and the Vλ gene (Vλpro), ΨVλ1, ΨVλ5, ΨVλ13, ΨVλ24, ΨVλ25. (Due to the absence of polymorphisms, the ΨVλ arrays at the two IgAλ alleles in DT40 cannot be readily distinguished by PCR.). Additionally, we assayed chromatin modifications at: (1) ΨVλ17, which due to a sequence polymorphism created during construction of DT40 PolyLacO-λ, is the only site in the ΨVλ array at which the rearranged and unrearranged alleles can be distinguished by use of specific PCR primers, (2) the rearranged allele of Vλ ($Vλ_R$), (3) the unrearranged allele of Vλ ($Vλ_U$), and (4) the Pol ϵ gene, an intrachromosomal control. Amplification of ωVλ sites was performed in duplex with the nonexpressed ovalbumin gene (Ova). Thus, Ova functions as an internal control, and the ΨVλ:Ova enrichment ratio from immunoprecipitations was normalized to ΨVλ:Ova ratio from total input DNA (see Material and Methods). Tethered VP16 increased both AcH3 (FIG. 17A) and AcH4 (FIG. 17B) levels in DT40 PolyLacO-λGFP-LacI-VP16 transfectants relative to control DT40 PolyLacO-λ GFP-LacI cells.

We used the sIgM loss variant assay to ask if tethering VP16 altered the clonal rate of Vλ sequence diversification. This fluctuation assay measures the fraction of variant cells that no longer express structurally intact sIgM, and thus scores mutation events resulting from gene conversion, point mutation, insertion or deletion (Sale et al., 2001; Yabuki et al., 2005). While gene conversion is the predominant pathway of Ig gene diversification in chicken B cells, if gene conversion is impaired (for example by the absence of essential recombination factors (Sale et al., 2001; Niedzwiedz et al., 2004; Hatanaka et al., 2005; Kawamoto et al., 2005; Mcllwraith et al., 2005; Yamamoto et al., 2005), other repair outcomes, particularly point mutations, will predominate. Thus diversification is monitored best by this loss of function assay, rather than an sIgM– to sIgM+ gain of function assay, which scores only gene conversion (Saribasak et al., 2006).

Figure 17B:
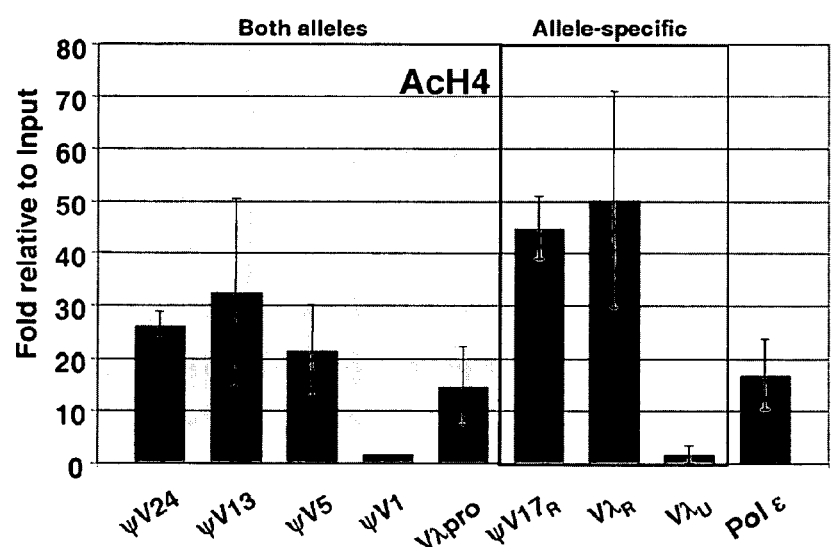
Figure 17C:
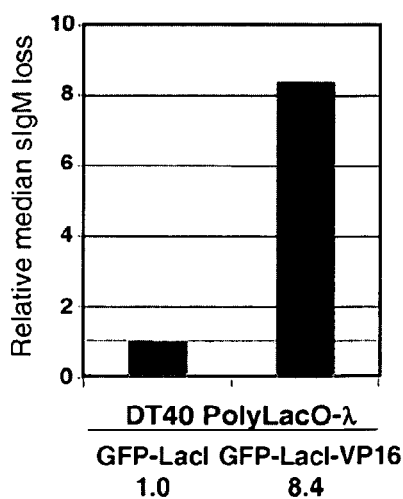
Figure 22:
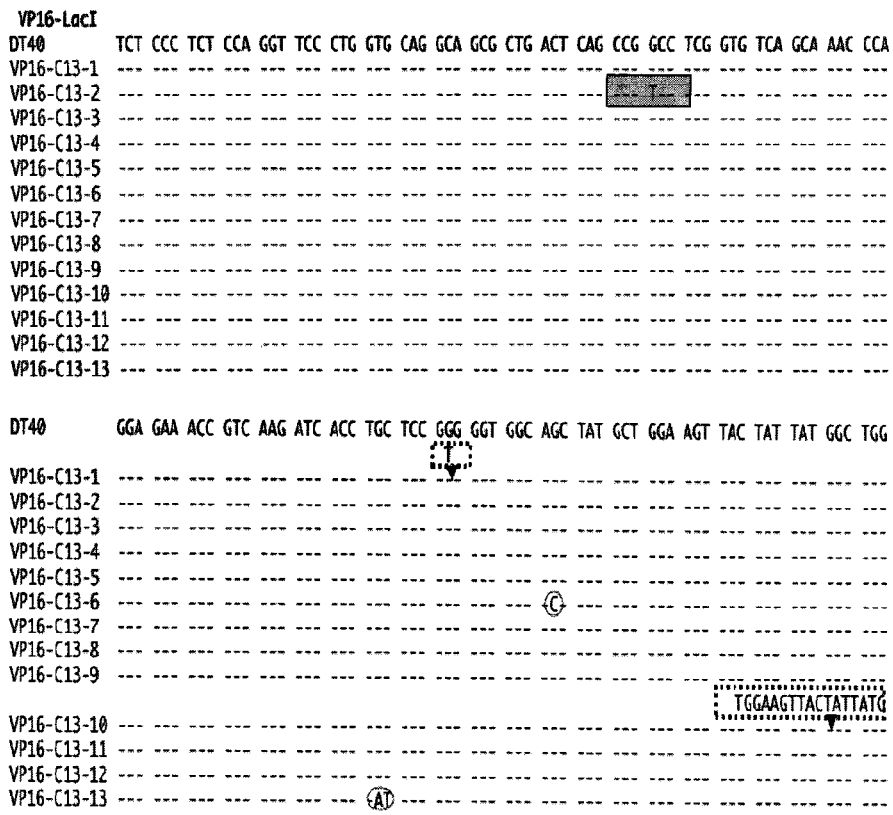
FIG. 22. Sequences of mutated V regions from single DT40 PolyLacO-λ GFP-LacI-VP16 cells. V regions were amplified from single sIgM– cells and then sequenced. Clear blue boxes outline long-tract gene conversion events; blue-shaded boxes outline short-tract gene conversion events; red circles denote point mutations; black dotted boxes indicate insertions; carats denote deletions.

Independent clonal derivatives of DT40 PolyLacO-λ GFP-LacI and DT40 PolyLacO-λ GFP-LacI-VP16 transfectants were established by limiting dilution cloning of sIgM+ cells, and following 4 weeks of culture the fraction of sIgM– cells in each population determined by flow cytometry of cells stained with anti-IgM antibody. Comparison of median percentages of sIgM– cells showed that DT40 PolyLacO-λ GFP-LacI-VP16 transfectants exhibited an 8.4-fold increase in diversification relative to DT40 PolyLacO-λ GFP-LacI control cells (FIG. 17B). Sequence analysis of Vλ regions amplified by single cell PCR showed that most diversification was by gene conversion in both control cells and cells in which VP16 was tethered at Igλ (FIG. 22).

Histone H3.3 is Enriched at the ΨVλ Donor Genes

Not only histone modifications but also localized changes in the histone composition of nucleosomes can contribute to regulation of chromatin structure. One histone variant associated with chromatin activation and deposited independently of replication is H3.3. Histone H3.3 is the principal H3-like variant to contain activation-associated posttranslational modifications (McKittrick et al., 2004; Henikoff, 2008), so it was of interest to ask if H3.3 was enriched at the ΨVλ array. To distinguish H3 from H3.3 by ChIP, we generated a DT40 derivative which stably expresses FLAG-tagged H3.3 (H3.3-FLAG).

Figure 18A:
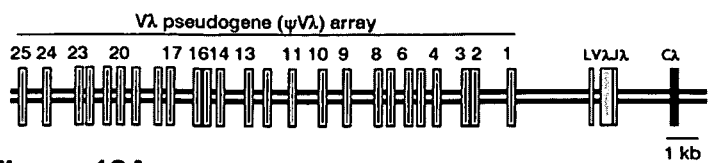
FIG. 18A-B. The H3.3 histone variant is enriched at the DT40 Igλ locus.
Figure 18B:
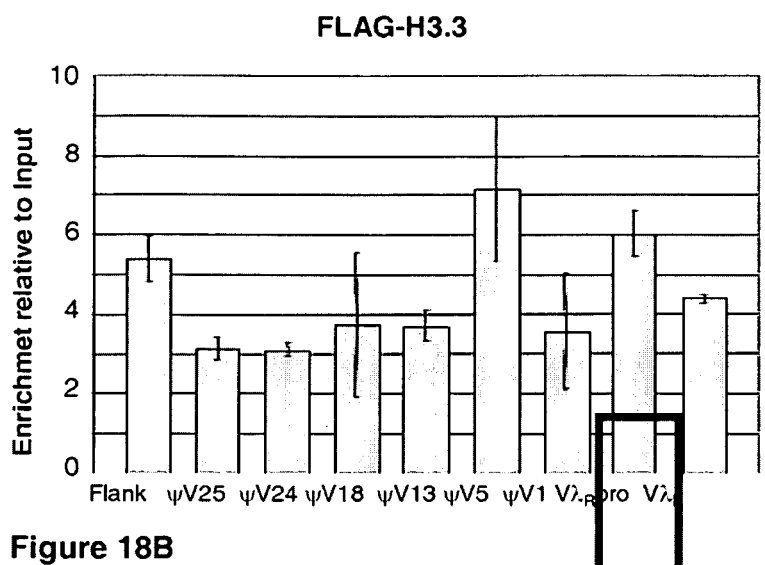

Characterization of H3.3 deposition by ChIP with an anti-FLAG antibody demonstrated enrichment of the H3.3 variant at the expressed $Vλ_R$ gene. Chromatin structure within the ΨVλ array was assayed by amplification of sites upstream of the rearranged and expressed Vλ gene including ΨVλ1, ΨVλ5, ΨVλ13, ΨVλ24, ΨVλ25, $ΨVλ17_R$, $Vλ_R$ (FIG. 18A), as well as the rearranged allele, $Vλ_U$; and at another gene on the same chromosome as Igλ, Pol ϵ. In a typical experiment, H3.3 was enriched more than 4-fold relative to input DNA at $Vλ_R$; but, strikingly, we observed considerable enrichment of H3.3 throughout the ΨVλ array, with greatest enrichment at ΨVλ5 and Vλpro (FIG. 18B). Enrichment of H3.3 within the ΨVλ array does not simply represent a graded spreading of the variant from the transcribed $Vλ_R$ gene to sites upstream, as proximal sites did not consistently display higher levels of enrichment than distal sites. The non-uniform chromatin structure of the locus suggests the presence of cis-elements, particularly in the ΨVλ5 region, that may regulate expression and/or diversification of the locus.

Tethered HIRA Causes a Local Increase in Histone Deposition

HIRA is a histone chaperone, and one of its functions is to assemble nucleosomes containing the histone variant, H3.3 (Ray-Gallet et al., 2002; Tagami et al., 2004). Enrichment of H3.3 at the ωVλ array thus suggested that tethering HIRA might accelerate Ig gene diversification, analogous to the effect of tethered VP16. To test this, we generated stable DT40 PolyLacO-λ HIRA-LacI transfectants, verified comparable levels protein expression by Western blotting (FIG. 19A), and showed that tethering did not affect cell cycle profile (FIG. 19B) or λ transcript levels (FIG. 19C). ChIP assays of AcH3 and AcH4 levels showed no difference between cells in which HIRA or GFP was tethered at Igλ.

Figure 20A:
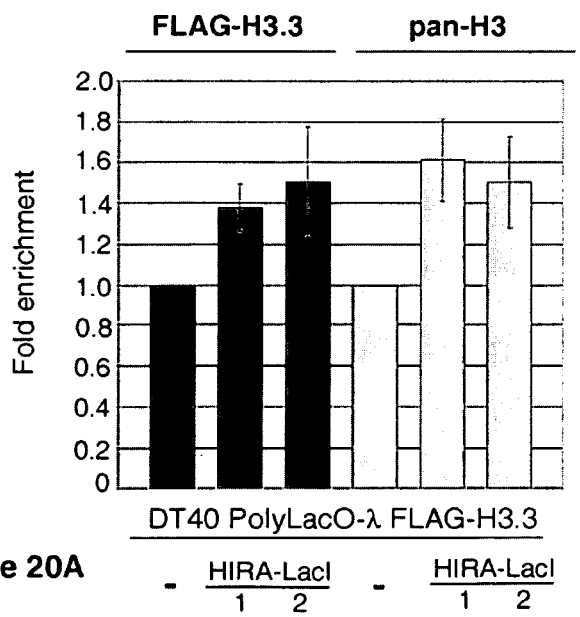
FIG. 20A-C. The H3.3 histone variant is enriched and gene conversion accelerated by HIRA tethering in DT40 PolyLacO-λ.

To ask if tethered HIRA increased H3.3 levels, we generated DT40 PolyLacO-λ FLAG-H3.3 HIRA-LacI transfectants, and then determined enrichment of FLAG-H3.3 at $ωVλ17_R$, where a polymorphism enables analysis of the tethered Igλ only. Those experiments showed a modest (1.4-fold) enrichment of FLAG-H3.3 in each of two independently HIRA-LacI transfectants FIG. 20A), relative to a control line.

Moreover, a comparable enrichment was evident when pan-H3 antibodies were used for ChIP (which detect H3 and other variants, including H3.3). Thus, HIRA appeared to cause a net enrichment of histones, including H3.3, and thus affected nucleosome density at ΨVλ.

Tethered HIRA Promotes Ig Gene Conversion

Figure 20B:
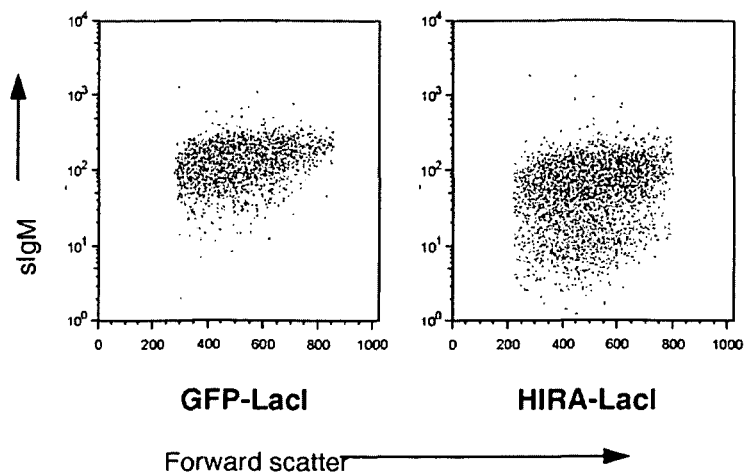
Figure 20C:
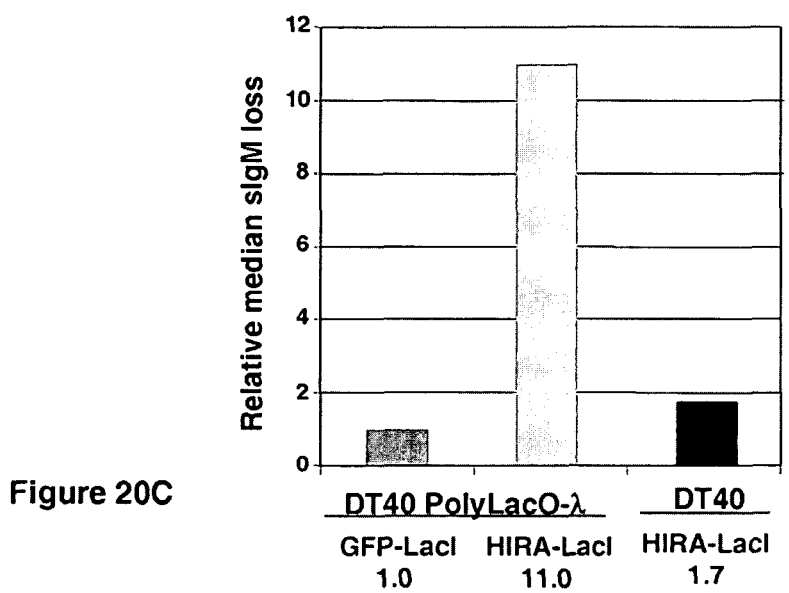
Figure 23:
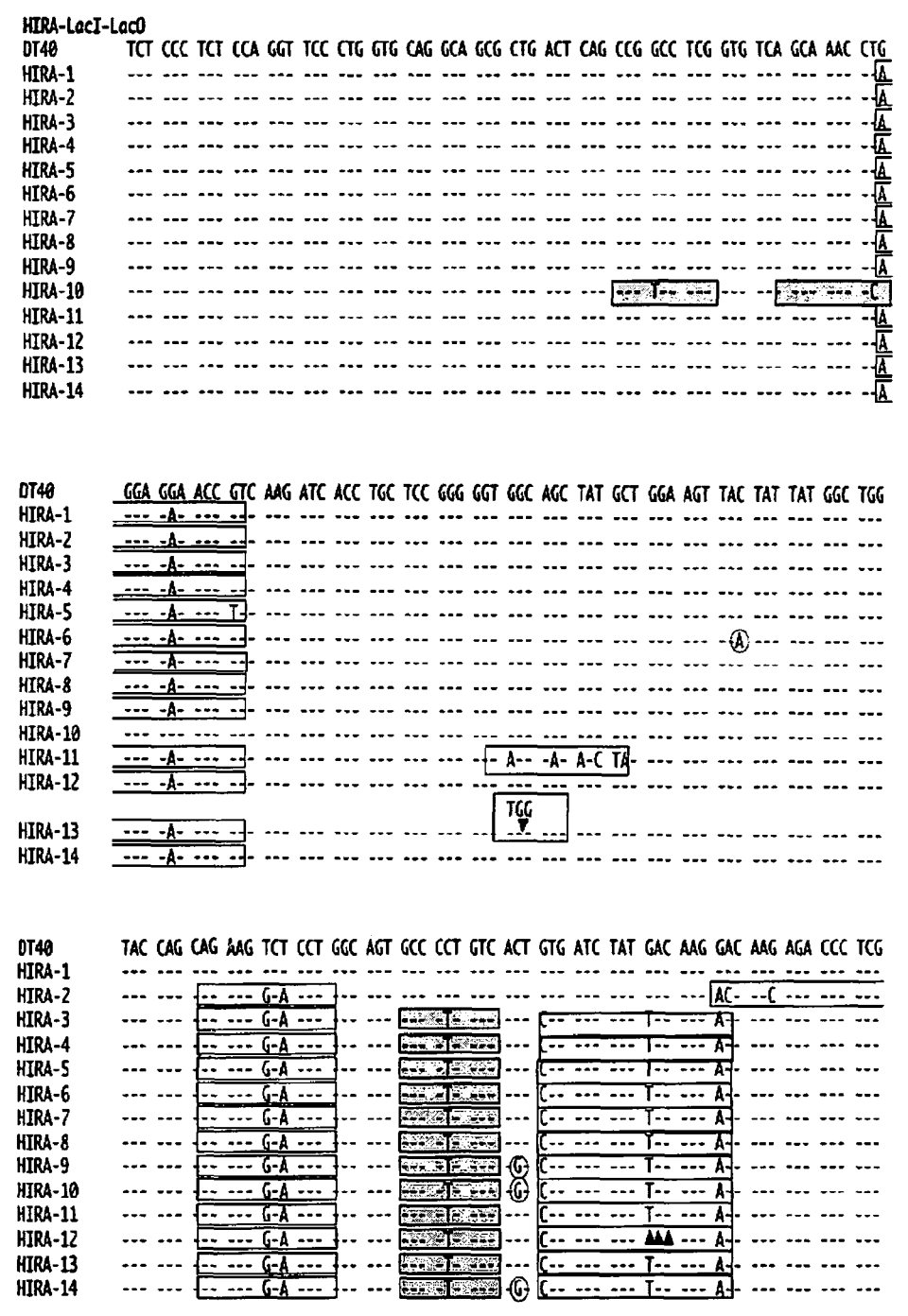

To ask if tethered HIRA affects the clonal rate of Ig gene diversification, we established independent clonal derivatives of DT40 PolyLacO-λ HIRA-LacI transfectants by limiting dilution cloning of sIgM+ cells, and following 4 weeks of culture the fraction of sIgM− cells in each population was determined. The fraction of sIgM− cells was clearly greater in the HIRA-LacI transfectants than in control cells (e.g. FIG. 20B). Comparison of median percentages of sIgM− cells showed that DT40 PolyLacO-λ HIRA-LacI cells exhibited an 11-fold increase in diversification relative to DT40 PolyLacO-λ GFP-LacI control cells (FIG. 20C). This did not simply reflect overexpression of HIRA, as only a modest acceleration in diversification (1.7-fold) was evident in transfectants of DT40 stably expressing HIRA (FIG. 20C). Sequence analysis of Vλ regions amplified by single cell PCR showed that most diversification was by gene conversion in control cells and in cells in which HIRA was tethered at Igλ (FIG. 23).

The Fraction of Short-tract Templated Mutations is Increased by Tethered VP16 or HIRA Tethered VP16 and HIRA accelerated the clonal rate of gene diversification comparably (8.4-fold and 11-fold, respectively), and gene conversion predominated in both. To establish whether subtle differences might distinguish mutational spectra, independent mutational events in the DT40 PolyLacO-λ HIRA-LacI and DT40 PolyLacO-λ GFP-LacI-VP16 transfectants were compared with DT40 PolyLacO-λ GFP-LacI control transfectants. Sequence changes were categorized as gene conversion if they were within a tract which was an exact match to at least 9 bp of a donor ΨVλ sequence, and contained one, two or more single base changes from the germline sequence. Events containing a single base difference and two or more differences were tallied separately as "short" and "long" tract gene conversion, because some mutations in the former class could in principle arise from point mutations which coincidentally matched ωVλ donor sequences. Nontemplated events, consisting of point mutations, deletions, and insertions, were also scored.

In DT40 PolyLacO-λ GFP-LacI-VP16 transfectants, 74% of events were templated, but a significant fraction of templated events (39%, or 29% of all mutation events) were short tract rather than long-tract gene conversion (Table 1, FIG. 22). There was also a significant fractions of insertions (13% compared to 0%). Gene conversion events similarly predominated (87%) among the events analyzed in from DT40 PolyLacO-λ$_R$ HIRA-LacI cells (Table 1, FIG. 23). Most gene conversion events were long-tract, but a significant minority (24%, or 21% of all mutation events) were short tract gene conversion. The remainder of events were point mutations (11%) and insertions (2%). We previously characterized mutagenic events in control DT40 PolyLacO-λ GFP-LacI transfectants, and found that most mutations were due to long-tract gene conversion events (77%), while a small fraction (3%) were either short tract conversion events or point mutations that coincidentally matched a donor sequence (Example 4; summarized in Table 1). The remaining mutations (20%) failed to correspond to any of the pseudogene donors and were, therefore, clear point mutations.

TABLE 1

Effect of tethered HP1 and VP16 on gene conversion.
Summary of sequences of Vλ regions carrying unique mutations from DT40 PolyLacO-λ GFP-LacI (n = 71; (Example 4), DT40 PolyLacO-λ GFP-LacI-VP16 (n = 31), and DT40 PolyLacO-λ HIRA-LacI (n = 137) transfectants. Data derived from at least two independent transfections.

| Gene Conversion | GFP-LacI | GFP-LacI-VP16 | HIRA-LacI |
|---|---|---|---|
| Long (2 or more nt) | 77% | 45% | 66% |
| Short (1 nt) | 3% | 29% | 21% |
| Total | 80% | 74% | 87% |
| Point mutation | 20% | 13% | 11% |
| Insertion | 0 | 13% | 2% |

Thus, acceleration of diversification by tethered VP16 and HIRA is due to increased levels of templated mutation. In both cases, most templated tracts contained two or more mutations; but about one-third of tracts contained only a single mutation. In contrast, essentially all gene conversion events in the GFP-LacI control cells contained at least two mutations. This suggests that the changes in donor chromatin structure may not only accelerate gene conversion but also limit the extent of gene conversion tracts; or that accelerated gene conversion may titrate factors that contribute to extending the length of conversion tracts.

Tethered HIRA Increases Nucleosome Density

Figure 21B:
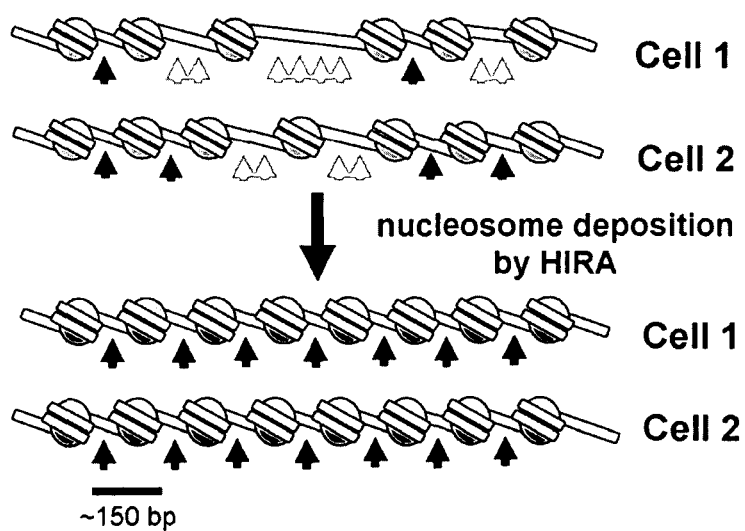
FIG. 21A-B. Distinct chromatin effects of tethered HIRA and VP16.
Figure 21A:
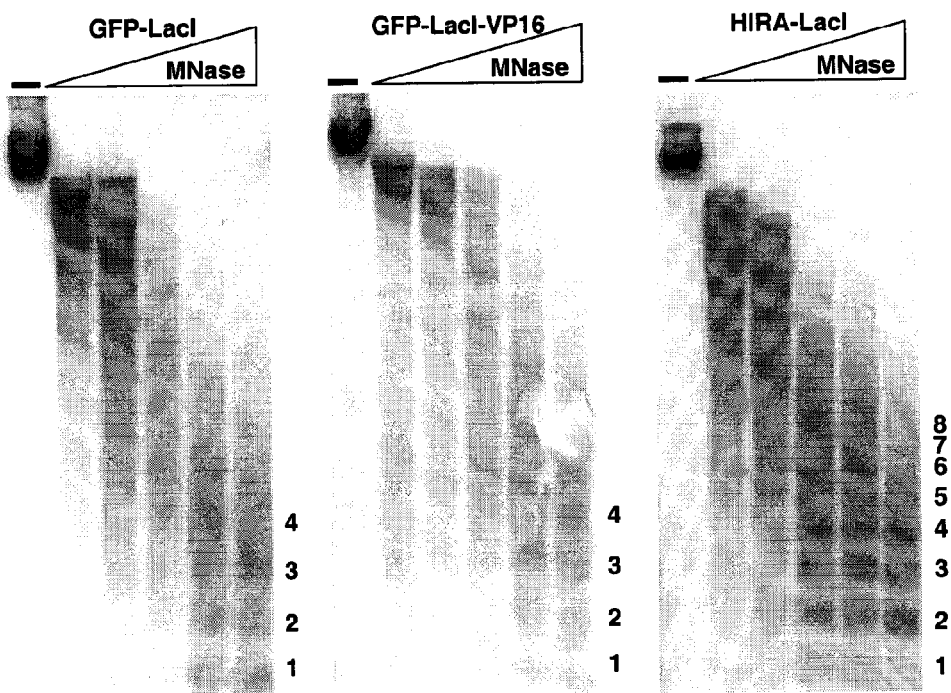

The results above show that tethered VP16 and HIRA had comparable effects on the outcome of Ig gene diversification, although each had different local effects: VP16 increased AcH3 and AcH4, while HIRA increased H3.3 and overall histone loading. To establish how loading of these different factors might affect chromatin, we probed chromatin structure using micrococcal nuclease (MNase). Nuclei were harvested, treated with varied amounts of MNase, genomic DNA purified, resolved and blotted, and then probed with labeled DNA homologous to the LacO repeats. The MNase digestion pattern of DT40 PolyLacO-λ GFP-LacI and DT40 PolyLacO-λ GFP-LacI-VP16 cells appeared comparable by this assay (FIG. 21). Digestion with high levels of MNase produced a clear limit product. This is the region of DNA (about 150 bp) that contacts the nucleosome, and is thereby protected from MNase. Spacing between individual nucleosomes can vary, causing slight variation in sizes of nucleosome multimers produced upon partial digestion, and producing the characteristically blurred bands migrating more slowly in the gel.

In contrast, MNase digestion of chromatin from DT40 PolyLacO HIRA-LacI cells revealed a different pattern: distinctive laddering was observed, not found in the control (FIG. 21, right). The sharply defined series of digestion products spanned from the 1-mers produced upon limit digestion up to 8-mers and beyond; while the ladder became blurred at sizes larger than 4-mers in the control and VP16-expressing cells. This suggests that tethering the histone chaperone HIRA increased the uniformity of linker size. That would occur if local nucleosome density were increased, consistent with the known role of HIRA as a histone chaperone, as well as with the evidence that tethering HIRA increased local enrichment of H3.3 and H3 (FIG. 18C).

Discussion

This example has shown that gene conversion can be accelerated by changes in chromatin structure, and that there are at least two different means to this end. Gene conversion was accelerated by an order of magnitude upon tethering either the activator, VP16, or the histone chaperone, HIRA, at the ΨVλ array in the chicken DT40 B cell line. Tethering VP16 increased levels of AcH3 and AcH4; while tethering HIRA did not affect those chromatin marks, but increased nucleosome density, in part by loading H3.3. The fact that different changes in the state of chromatin are similarly enabling for homologous recombination shows that the cell has available redundant pathways for regulating uses of DNA in recombination.

The effect of tethering VP16 and HIRA on Ig gene diversification is distinct from that of tethering the heterochromatin protein HP1. Tethering HP1 caused a nearly 3-fold increase in point mutations, accompanied by a decrease in templated mutations (Example 4). These differences show that donor chromatin structure may be either activated or repressed for homology-directed DNA repair, with consequences on the repair outcome.

Currently, allelic homology-directed repair is thought to predominate in S phase, and to depend on sister chromatids for templates. The potential for local alterations of chromatin structure to activate regions for homology-directed repair suggests that regulation may be more complex, and require not only the presence of a homologous donor but also chromatin structure that is conducive to repair.

Tethering of HIRA or VP16 accelerated clonal diversification rates by promoting templated mutation. In both cases, an increase was evident in the fraction of templated mutations in which only a single templated base change was evident in the mutation tract. While these "short tract" mutations comprised only 29% and 21% of total mutations in VP16 and HIR1 transfectants, respectively, this category of mutations was essentially absent (3%) in GFP-LacI transfectants.

Short gene conversion tracts could arise if factors necessary to promote long tract gene conversion are not sufficiently abundant to support the increase in gene in cells in which either VP16 or HIRA is tethered to PolyLacO. Alternatively, the increase in mutations in this category could reflect changes in chromatin structure caused by tethering these factors, which could affect both nucleosome position and linker length.

Nucleosome density is increased upon tethering HIRA. This density increase is likely to reflect diminished linker length. If linker regions are preferred templates for gene conversion, shortening of those regions in the HIRA transfectants may contribute to decreased gene conversion tract length. Shortening of nucleosome length may, alternatively, re-phase nucleosomes so that, although chromatin is active for recombination, the nonhomologous regions between the ΨV become less accessible.

The role of HIRA at the pseudogenes is a novel example of how histone loading affects DNA repair. The role of HIRA at the untranscribed pseudogenes is particularly interesting as many studies have found transcription required for de novo H3.3 deposition (Ahmad and Henikoff, 2002a; Ahmad and Henikoff, 2002b; Janicki et al., 2004; Wirbelauer et al., 2005). The results now suggest that transcription is not prerequisite to H3.3 loading.

These results increase our understanding of the constraints exerted by chromatin constraints on recombination. In addition, they provide insight into the necessary chromatinization of molecules used for gene targeting and/or gene therapy.

References

Ahmad, K., and Henikoff, S. (2002a). Proc Natl Acad Sci U S A 99 Suppl 4: 16477-16484.
Ahmad, K., and Henikoff, S. (2002b). Mol Cell 9: 1191-1200.
Arakawa, H., et al., (2002). Science 295: 1301-1306.
Brown, D. T. (2001). Genome Biol 2: REVIEWS0006.
Carpenter, A. E., et al. (2005) . . . Mol Cell Biol 25: 958-968.
Cummings, W. J., et al. (2007). See Example 4.
Hatanaka, A., et al. (2005) . . . Mol Cell Biol 25: 1124-1134.
Henikoff, S. (2008) . . . Nat Rev Genet 9: 15-26.
Janicki, S. M., et al. (2004) . . . Cell 116: 683-698.
Kawamoto, T., et al. (2005) . . . Mol Cell 20: 793-799.
Kidd, J. M., et at (2008) . . . Nature 453: 56-64.
Lupski, J. R. (2007). Nat Genet 39: S43-47.
Mcllwraith, M. J., et al. (2005) . . . Mol Cell 20: 783-792.
McKittrick, E., et al. (2004) . . . Proc Natl Acad Sci U S A 101: 1525-1530.
Neely, K. E., et al. (2002) . . . Mol Cell Biol 22: 1615-1625.
Niedzwiedz, W., et al. (2004) . . . Mol Cell 15: 607-620.
Prioleau, M. N., et al. (1999) . . . Embo J 18: 4035-4048.
Ray-Gallet, D., et al. (2002) . . . Mol Cell 9: 1091-1100.
Rodrigue, A., et al. (2006) . . . Embo J 25: 222-231.
Sale, J. E., et al. (2001) . . . Nature 412: 921-926.
Saribasak, H., et al. (2006) . . . J Immunol 176: 365-371.
Seo, H., et al. (2005) . . . Nat Biotechnol 23: 731-735.
Tagami, H., (2004) . . . Cell 116: 51-61.
Tumbar, T., et al. (1999) . . . J Cell Biol 145: 1341-1354.
West, S. C. (2003) . . . Nat Rev Mot Cell Bid 4: 435-445.
Wirbelauer, C., et al. (2005) . . . Genes Dev 19: 1761-1766.
Yabuki, M., et al. (2005) . . . Nat Immunol 6: 730-736.
Yamamoto, K., et. al. (2005) . . . Mol Cell Biol 25: 34-43.

Example 6

Generation of Diagnostic Antibodies to Mesothelin and HE4

This example illustrates how one can use the invention to develop antibodies against mesothelin and HE4, well-validated ovarian cancer biomarkers. The antibodies identified will be valuable new diagnostic reagents, adding useful redundancy to clinical tests. This example further validates the utility of DT40 PolyLacO as a platform for selection of diagnostic antibodies that recognize other biomarkers.

DT40 PolyLacO as a vehicle for antibody development: identification of new antibodies against two ovarian cancer biomarkers, mesothelin (Scholler et al., 1999; Frierson et al., 2003) and HE4 (Hellstrom et al., 2003).

Mesothelin is an epithelial differentiation marker highly expressed on cancer cells of many origins, including ovarian cancer (Robinson et al., 2003). HE4 (aka WFDC2) is a member of the whey-acidic protein (WAP) family, members of which are secreted at high levels and associated with cancer, although function is not understood (Bouchard et al., 2006). We have obtained recombinant mesothelin and HE4. These proteins are expressed in yeast as biotin fusions, which facilitates binding to streptavidin-coupled beads or plates for selection or ELISA assays (Scholler et al., 2006; Bergan et at., 2007). We have also obtained single-chain antibodies (scFv) against mesothelin and HE4 (Scholler et al., 2008), which provide a standard for initial comparison of affinities of newly identified antibodies.

To identify high affinity antibodies to mesothelin and HE4, iterative hypermutation and clonal selection for recognition of each recombinant antigen is performed. Clones are expanded under conditions that accelerate hypermutation; selected for clones that bind mesothelin or HE4 with high affinity by magnetic activated cell sorting; and antibody affinity of supernatants is assayed by ELISA assay. Populations producing high affinity antibodies are further selected to enhance affinity and specificity (FIG. 3).

Selection can be initiated on three populations of $10^8$ cells each (corresponding to 100 ml of culture). Each population can be derived from a single cell isolated by limiting dilution, and then cultured under conditions that accelerate hypermutation. To minimize enrichment of "sticky" cells, which bind beads alone, prior for enrichment for a desired specificity each population is first cleared with biotin-bound beads. Enrichment for a desired specificity is achieved conveniently by magnetic activated cell sorting (MACS). Using MACS, it is possible to enrich very quickly from very large sample sizes ($10^8$ cells), consistently achieving 100-fold enrichment of populations comprising <0.1% of the starting sample (Volna et al., 2007). The selected population is expanded and reselected using the same protocol.

Based on results of others (e.g. Cumbers et al., 2002) we predict that cells producing antibodies specific for each "antigen" will be recovered at or before round 2-3 of iterative hypermutation and selection (2-3 weeks), and probably earlier. One can test antibody affinity of cell pools by ELISA assay; and when affinity is in the 1-10 nM range, limiting dilution cloning is performed, and clones that make high affinity antibody identified. Limiting dilution cloning is carried out in medium containing IPTG, which releases repressor from operator to decelerate hypermutation. Antibody produced from these clonal populations will be further characterized, as described below.

Three criteria can be used to establish that this approach has succeeded:

1. Affinity and Specificity.

Efficacy of antibody development is validated by demonstrating that antibody affinity increases in the course of selection. Antibody affinities are first measured by ELISA assays of dilutions of supernatant of cells cultured for 48 hr, in the presence of IPTG, to minimize further hypermutation, in IgM-depleted medium, to minimize background in the ELISA. To ensure that antibodies recognize the antigen and not the recombinant scaffold in which it is displayed, reactivity is tested with biotin and streptavidin. A side-by-side comparison of anti-mesothelin and anti-HE4 antibodies against both recombinant antigens serves as a test of cross-reactivity. Affinities are compared to control scFv antibodies directed to mesothelin or HE4. Following establishment of high affinity clonal populations, Kd will be determined quantitatively by surface plasmon resonance by Biacore.

2. Targeting of Mutagenesis.

The cellular mechanism that hypermutates antibody genes in the course of clonal selection concentrates mutations in the CDRs, the subdomains of the V regions that contact antigen. We predict that high affinity clones isolated by accelerated hypermutation and selection will similarly concentrate mutations in the CDRs. To test this, one can use single-cell PCR to amplify the VH and VL regions of individual B cells following affinity selection, sequence the VH and VL regions, and compare these sequences with those of the unselected population.

3. Maintenance of Specificity and Affinity upon Culture with IPTG.

The power of this platform for antibody production depends in part on the ability to limit hypermutation when a high affinity clone has been generated. To test this, one can culture clonal populations in the presence and absence of IPTG, and compare average affinities of expanded cultures by flow cytometry of cells bound to fluorescent-tagged mesothelin or HE4. Affinities are predicted to remain constant in cultures containing IPTG, but to increase or decrease in cultures lacking IPTG. Thus, the distribution of fluorescence signal will be broader in the IPTG-containing cultures.

References

Bergan, L., et al. (2007). Cancer Lett 255, 263-274.
Bouchard, D., et al. (2006). Lancet Oncol 7, 167-174.
Cumbers, S. J., et al. (2002). Nat Biotechnol 20, 1129-1134.
Frierson, H. F., Jr., et al. (2003). Hum Pathol 34, 605-609.
Hellstrom, I., et al. (2003). Cancer Res 63, 3695-3700.
Hung, C. F., et al. (2008). Immunol Rev 222, 43-69.
Liu, X. Y., et al. (2008). Immunol Rev 222, 9-27.
Robinson, B. W., et al. (2003). Lancet 362, 1612-1616.
Sale, J. E. (2004). DNA Repair (Amst) 3, 693-702.
Scholler, N., et al. (1999). Proc Natl Acad Sci U S A 96, 11531-11536.
Scholler, N., et al. (2006). J Immunol Methods 317, 132-143.
Scholler, N., et al. (2008). Clin Cancer Res 14, 2647-2655.
Seo, H., et al. (2005). Nat Biotechnol 23, 731-735.
Volna, P., et al. (2007). Nucleic Acids Res 35, 2748-2758.

Throughout this application various publications are referenced. The disclosures of these publications in their entireties are hereby incorporated by reference into this application in order to describe more fully the state of the art to which this invention pertains.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A B cell modified to reversibly induce accelerated diversification of a target gene, the B cell comprising:
   (a) a cis-regulatory element operably linked to a target gene, wherein the target gene comprises a promoter and a coding region;
   (b) a fusion construct that encodes a tethering factor fused to a diversification factor, wherein the tethering factor specifically binds to the cis-regulatory element of (a) and the diversification factor reversibly induces accelerated diversification of the coding region in the target gene.

2. The B cell of claim 1, which is a DT40 chicken B cell.

3. The B cell of claim 1, which is a human B cell.

4. The B cell of claim 1, wherein the cis-regulatory element is a polymerized Lactose operator (LacO) and the tethering factor is a lactose repressor (LacI).

5. The B cell of claim 1, wherein the cis-regulatory element is a tetracycline operator (TetO) and the tethering factor is tetracycline repressor (TetR).

6. The B cell of claim 1, wherein the diversification factor is a transcriptional regulator, a heterochromatin-associated protein, a histone chaperone, a chromatin remodeler, a component of the nuclear pore complex, a gene regulator or a combination thereof.

7. The B cell of claim 1, wherein the diversification factor is a DNA repair factor, a DNA replication factor, a resolvase, a helicase, a cell cycle regulator, a ubquitylation factor, a sumoylation factor, or a combination thereof.

8. The B cell of claim 6, wherein the transcriptional regulator is VP16 or E47.

9. The B cell of claim 6, wherein the heterochromatin-associated protein is HP1.

10. The B cell of claim 6, wherein the histone chaperone is HIRA.

11. The B cell of claim 1, wherein the target gene is a human Ig gene.

12. The B cell of claim 1, wherein the target gene is an IgL gene.

13. The B cell of claim 1, wherein the target gene is an IgH gene.

14. The B cell of claim 1, wherein the target gene comprises a heterologous coding region and regions encoding a transmembrane domain and a cytoplasmic tail sufficient to effect display of the target gene product on the B cell surface.

15. A kit comprising:
   (a) a B cell comprising a cis-regulatory element operably linked to a target gene, wherein the target gene comprises a promoter and a coding region; and
   (b) one or more containers; and
   (c) one or more fusion constructs stored in a container of (b), wherein each fusion construct is expressable in the B cell and encodes a tethering factor fused to a diversification factor, wherein the tethering factor specifically binds to the cis-regulatory element of the B cell of (a) and the diversification factor reversibly induces accelerated diversification of the coding region in the target gene.

16. The kit of claim 15, wherein the B cell is a DT40 chicken B cell.

17. The kit of claim 15, wherein the B cell is a human B cell.

18. The kit of claim 15, wherein the cis-regulatory element is a polymerized Lactose operator (LacO) and the tethering factor is a lactose repressor (LacI).

19. The kit of claim 15, wherein the cis-regulatory element is a tetracycline operator (TetO) and the tethering factor is tetracycline repressor (TetR).

20. The kit of claim 15, wherein the diversification factor is a transcriptional regulator, a heterochromatin-associated protein, a histone chaperone, a chromatin remodeler, a component of the nuclear pore complex, a gene regulator or a combination thereof.

21. The kit of claim 15, wherein the diversification factor is a DNA repair factor, a DNA replication factor, a resolvase, a helicase, a cell cycle regulator, a ubquitylation factor, a sumoylation factor, or a combination thereof.

22. The kit of claim 20, wherein the transcriptional regulator is VP16 or E47.

23. The kit of claim 20, wherein the heterochromatin-associated protein is HP1.

24. The kit of claim 20, wherein the histone chaperone is HIRA.

25. The kit of claim 15, wherein the target gene is a human Ig gene.

26. The kit of claim 15, wherein the target gene is an IgL gene.

27. The kit of claim 15, wherein the target gene is an IgH gene.

28. The kit of claim 15, wherein the target gene comprises a heterologous coding region and regions encoding a transmembrane domain and a cytoplasmic tail sufficient to effect display of the target gene product on the B cell surface.

29. The B cell of claim 1, wherein the accelerated diversification of the coding region in the target gene is reversibly induced when the B cell is cultured under conditions that allow expression of the tethering factor fused to the diversification factor.

30. The B cell of claim 1, wherein the accelerated diversification of the coding region in the target gene is reversibly induced when the B cell is cultured in the presence of a regulatory molecule, wherein the regulatory molecule modulates binding of the tethering factor to the cis-regulatory element, thereby modulating accelerated diversification of the coding region in the target gene.

31. The kit of claim 15, wherein the kit further comprises a regulatory molecule stored in container (b), wherein the regulatory molecule modulates binding of the tethering factor to the cis-regulatory element, thereby modulating accelerated diversification of the coding region in the target gene.

* * * * *

UNITED STATES PATENT AND TRADEMARK OFFICE
CERTIFICATE OF CORRECTION

| | | |
|---|---|---|
| PATENT NO. | : 8,679,845 B2 | Page 1 of 1 |
| APPLICATION NO. | : 12/598031 | |
| DATED | : March 25, 2014 | |
| INVENTOR(S) | : Nancy Maizels et al. | |

It is certified that error appears in the above-identified patent and that said Letters Patent is hereby corrected as shown below:

In The Specification

Figure 14B:
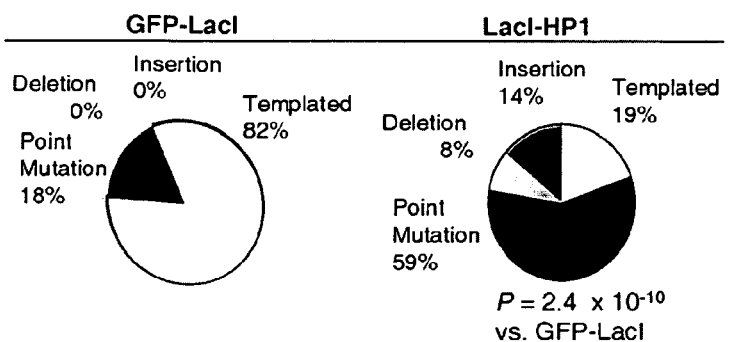

Column 7, line 36, "FIG. 14A-E" should read -- FIG. 14A-B --.

Figure 19A:
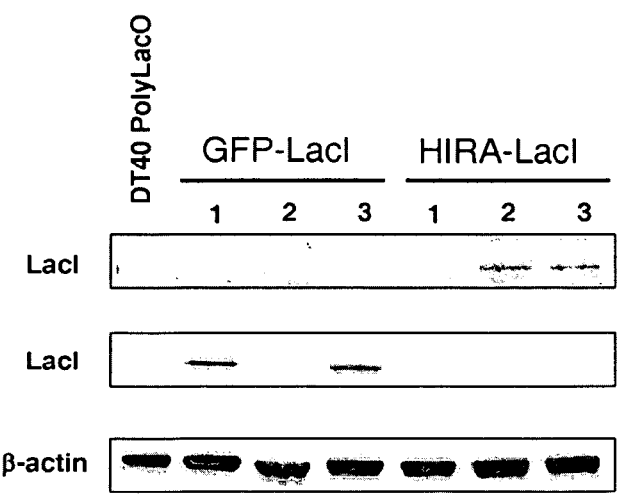
Figure 19B:
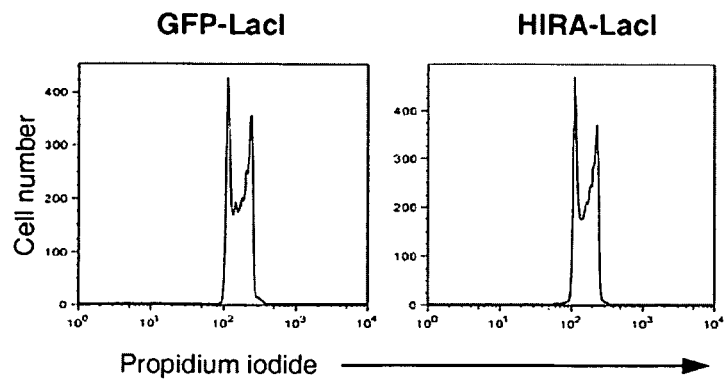
Figure 19C:
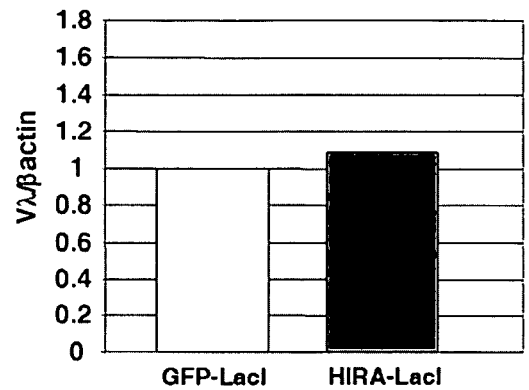

Column 8, line 33, "FIG. 19A-E" should read -- FIG. 19A-C --; lines 42-45, delete the sentences "FIG. 19E: Fluorescent image of DT40 PolyLacO-λ GFP-LacI-VP16 transfectants. Arrows indicate GFP-LacI-VP16 bound to Igλ. Nuclei were counterstained with DAPI (blue).".

Signed and Sealed this
Twenty-seventh Day of January, 2015

Michelle K. Lee
*Deputy Director of the United States Patent and Trademark Office*